(12) United States Patent
Cummings et al.

(10) Patent No.: US 7,563,784 B2
(45) Date of Patent: Jul. 21, 2009

(54) PROTEASE INHIBITORS

(75) Inventors: Maxwell D. Cummings, Strafford, PA (US); Robert W. Marquis, Jr., Wayne, PA (US); Yu Ru, Wayne, PA (US); Scott K. Thompson, Phoenixville, PA (US); Daniel F. Veber, Ambler, PA (US); Dennis S. Yamashita, Wayne, PA (US)

(73) Assignee: SmithKline Beecham Corporation, King of Prussia, PA (US)

( * ) Notice: Subject to any disclaimer, the term of this patent is extended or adjusted under 35 U.S.C. 154(b) by 340 days.

(21) Appl. No.: 11/410,558

(22) Filed: Apr. 25, 2006

(65) Prior Publication Data

US 2006/0194787 A1 Aug. 31, 2006

Related U.S. Application Data

(63) Continuation of application No. 10/239,343, filed as application No. PCT/US01/07094 on Mar. 7, 2001, now Pat. No. 7,071,184.

(60) Provisional application No. 60/191,000, filed on Mar. 21, 2000, provisional application No. 60/206,341, filed on May 23, 2000, provisional application No. 60/211,759, filed on Jun. 14, 2000, provisional application No. 60/217,445, filed on Jul. 10, 2000.

(51) Int. Cl.
*A61P 19/08* (2006.01)
*A61P 19/10* (2006.01)
*A61K 31/55* (2006.01)
*C07D 401/00* (2006.01)
*C07D 403/00* (2006.01)
*C07D 413/00* (2006.01)

(52) U.S. Cl. ............................ 514/211.03; 514/217.03; 514/217.04; 514/217.05; 514/217.06; 514/217.07; 514/217.08; 514/217.09; 514/217.1; 514/217.11; 540/525; 540/596; 540/597; 540/598; 540/599; 540/601; 540/602; 540/603; 540/604; 540/605

(58) Field of Classification Search ............ 514/211.03, 514/217.03, 217.04, 217.05, 217.06, 217.07, 514/217.08, 217.09, 217.1, 217.11; 540/525, 540/596, 597, 598, 599, 601, 602, 603, 604
See application file for complete search history.

(56) References Cited

U.S. PATENT DOCUMENTS

| 4,038,247 | A | 7/1977 | Muller et al. |
| 4,447,419 | A | 5/1984 | Quadro |
| 4,518,528 | A | 5/1985 | Rasnick |
| 4,638,010 | A | 1/1987 | Weller, III et al. |
| 4,749,792 | A | 6/1988 | Natarajan et al. |
| 4,994,471 | A | 2/1991 | Lalinde et al. |
| 5,057,525 | A | 10/1991 | Van Daele |
| 5,142,056 | A | 8/1992 | Kempe et al. |
| 5,206,251 | A | 4/1993 | Khanna et al. |
| 5,216,168 | A | 6/1993 | Khanna et al. |
| 5,374,637 | A | 12/1994 | Van Daele |
| 5,395,824 | A | 3/1995 | Higuchi et al. |
| 5,422,359 | A | 6/1995 | Ando et al. |
| 5,424,325 | A | 6/1995 | Ando et al. |
| 5,501,969 | A | 3/1996 | Hastings et al. |
| 5,523,313 | A | 6/1996 | Nunami et al. |
| 5,585,387 | A | 12/1996 | Lu et al. |
| 5,668,128 | A | 9/1997 | Tsubotani et al. |
| 5,830,850 | A | 11/1998 | Gelb et al. |
| 5,861,298 | A | 1/1999 | DeBouck et al. |
| 5,902,882 | A | 5/1999 | Matzinger et al. |
| 5,948,669 | A | 9/1999 | Field et al. |
| 5,998,470 | A | 12/1999 | Halbert et al. |
| 6,057,362 | A | 5/2000 | Yamashita |
| 6,232,342 | B1 | 5/2001 | Carr et al. |
| 6,274,336 | B1 | 8/2001 | Abdel-Meguid et al. |
| 6,284,777 | B1 | 9/2001 | Halbert et al. |
| 6,331,542 | B1 | 12/2001 | Carr et al. |
| 6,369,077 | B1 | 4/2002 | Marquis, Jr. et al. |
| 6,534,498 | B1 * | 3/2003 | Marquis et al. ........ 514/217.07 |

(Continued)

FOREIGN PATENT DOCUMENTS

AU          8667002          7/1987

(Continued)

OTHER PUBLICATIONS

Baggio, et al.; From Poor Substrates to Good Inhibitors: Design of Inhibitors for Serine and Thiol Proteases; Biochem; 1996; 35/11; 3351-3353.

(Continued)

*Primary Examiner*—Brenda L Coleman
(74) *Attorney, Agent, or Firm*—Linda E. Hall; Alan Scrivner; Charles Kinzig

(57) ABSTRACT

The present invention provides $C_{1-6}$alkyl-4-amino-azepan-3-one protease inhibitors and pharmaceutically acceptable salts, hydrates and solvates thereof which inhibit proteases, including cathepsin K, pharmaceutical compositions of such compounds, novel intermediates of such compounds, and methods for treating diseases of excessive bone loss or cartilage or matrix degradation, including osteoporosis; gingival disease including gingivitis and periodontitis; arthritis, more specifically, osteoarthritis and rheumatoid arthritis; Paget's disease; hypercalcemia of malignancy; and metabolic bone disease; and parasitic diseases, including malaria, by administering to a patient in need thereof one or more compounds of the present invention.

7 Claims, No Drawings

U.S. PATENT DOCUMENTS

| | | | |
|---|---|---|---|
| 6,566,373 | B2 | 5/2003 | Gribble et al. |
| 6,583,137 | B1 | 6/2003 | Marquis, Jr. et al. |
| 7,071,184 | B2 * | 7/2006 | Cummings et al. ..... 514/217.04 |
| 2003/0044399 | A1 | 3/2003 | Thompson et al. |
| 2004/0034013 | A1 | 2/2004 | Cummings, Jr. et al. |
| 2004/0229863 | A1 | 11/2004 | Cummings, Jr. et al. |

FOREIGN PATENT DOCUMENTS

| | | |
|---|---|---|
| CA | 2033497 | 1/1991 |
| EP | 0237082 A | 9/1987 |
| EP | 0525420 A1 | 2/1993 |
| EP | 0543310 | 5/1993 |
| EP | 0603873 | 12/1993 |
| EP | 0611756 | 2/1994 |
| EP | 0623592 | 11/1994 |
| EP | 0504938 | 3/1998 |
| JP | 2570686 | 1/1997 |
| WO | WO9204371 | 3/1992 |
| WO | WO9400095 | 1/1994 |
| WO | WO9505192 | 2/1994 |
| WO | WO9404172 | 3/1994 |
| WO | WO9423033 | 10/1994 |
| WO | WO9524182 A | 10/1994 |
| WO | WO9613523 | 5/1996 |
| WO | WO9640737 | 12/1996 |
| WO | WO9716177 | 5/1997 |
| WO | WO9716433 | 5/1997 |
| WO | WO9747642 | 12/1997 |
| WO | WO9747643 | 12/1997 |
| WO | WO9749668 | 12/1997 |
| WO | WO9805336 | 2/1998 |
| WO | WO9808802 | 3/1998 |
| WO | WO9812211 | 3/1998 |
| WO | WO9846582 | 10/1998 |
| WO | WO9848799 | 11/1998 |
| WO | WO9849152 | 11/1998 |
| WO | WO9850342 | 11/1998 |
| WO | WO9911637 | 3/1999 |
| WO | WO9953039 | 10/1999 |
| WO | WO9959526 | 11/1999 |
| WO | WO9959570 | 11/1999 |
| WO | WO9964399 | 12/1999 |
| WO | WO9966925 | 12/1999 |
| WO | WO0009653 | 2/2000 |
| WO | WO0029408 | 5/2000 |
| WO | WO0038687 | 7/2000 |
| WO | WO0039115 | 7/2000 |
| WO | WO0049011 | 8/2000 |
| WO | WO0054769 | 9/2000 |
| WO | WO0058296 | 10/2000 |
| WO | WO0107436 | 2/2001 |
| WO | WO0134153 | 5/2001 |
| WO | WO0134154 | 5/2001 |
| WO | WO0134155 | 5/2001 |
| WO | WO0134156 | 5/2001 |
| WO | WO0134157 | 5/2001 |
| WO | WO0134158 | 5/2001 |
| WO | WO0134159 | 5/2001 |
| WO | WO0134160 | 5/2001 |
| WO | WO0134565 | 5/2001 |
| WO | WO0134566 | 5/2001 |
| WO | WO0134599 | 5/2001 |
| WO | WO0170232 | 9/2001 |
| WO | WO0217924 | 3/2002 |
| WO | WO02092563 | 11/2002 |
| WO | WO03026770 | 4/2003 |
| WO | WO03045909 | 6/2003 |
| WO | WO03053331 | 7/2003 |
| WO | WO03097593 | 11/2003 |
| WO | WO03099844 | 12/2003 |
| WO | WO03103574 | 12/2003 |
| WO | WO03104257 | 12/2003 |
| WO | WO2004017911 | 3/2004 |
| WO | WO2005013909 | 2/2005 |
| WO | WO2005034838 | 4/2005 |
| ZA | 829141 | 8/1983 |
| ZA | 839532 | 6/1985 |
| ZA | 873821 | 11/1987 |

OTHER PUBLICATIONS

Elmore, et al; "A New Method for Determining the Absolute Molarity of Solutions of Trypsin and Chymotrypsin . . . "; Biochem J; 1968; 107; 103-107.

Barker, et al.; "The Reaction of an a-Aza-Amino Acid Derivative with Chymotrypsin and Its Use as a Ligand . . . "; Biochem J.; 1974; 139; 555-563.

Delaisse, et al; "In Vivo and In Vitro Evidence for the Involvement of Cysteine Proteinases in Bon Resorption"; Biochemical and Biophysical Research Communications; 1984; 125/2; 441-447.

Inaoka, et al; "Molecular Cloning of Human cDNA for Cathepsin K: Novel Cysteine Proteinase Predominately Expressed in Bone"; Biochemical and Biophysical Research Communications; 1995; 206/1; 89-96.

Auger, et al; "Solid-State 13C NMR Study of a Transglutaminase-Inhibitor Adduct"; Biochemistry; 1993; 32/15; 3930-3934.

Bromme, et al; Biochem. J; 1996; 315; 85-89.

Delaisse, et al; "Inhibition of bone resorption in culture by inhibitors of thiol proteinases"; Biochem. J.; 1980; 192; 365-368.

Barrett, et al; "L-trans-Epoxysuccinyl-leucylamido(4-guanidino)butane(E-64) and its analogues . . . "; Biochem. J.; 1982; 201; 189-198.

Grinde; "Selective Inhibition of Lysomal Protein Degradation By the Thiol Proteinase . . . "; Biochem. J. Biophys. Acta.; 1982; 701; 328-333.

Greenlee, et al; "Azapeptides: A New Class of Angiotensin-Converting Enzyme Inhibitiors"; Biochem. & Biophys. Research Communications; 1984; 122/2; 791-797.

Graybill, et al.; Bioorganic & Medicinal Chemistry Letters; 1992; 2/11; 1375-1380.

Castelhano, et al.l; "Synthesis, Chemistry and Absolute Configuration of Novel Transglutaminase Inhibitors Containing a 3-Halo-4,5-dihydroisoxazole"; Bioorg. Chem; 1988; 16/3; 335-340.

Delaise, et al; "The Effects of Inhibitors of Cysteine-Proteinases and Collagenase on the Resorptive Activity of Isolated Osteoclasts"; Bone; 8; 305-313; 1987.

Kawada, et al; "Polymer Compositions"; Chemical Abstracts; 1971; 83.

Database WPIDS on STN,; 1984; AN85-029005, JP 59225172A; Abstract; Derwent Publications LTD.

Calabretta, et al.; "Peptidyl and azapeptidyl methylketones as substrate analog inhibitors of papain and cathepsin B"; Eur. J. Med. Chem.; 1995; 30; 931-941.

Shi, et al.; Molecular cloning of human cathepsin O, a novel endoproteinase and homologue of rabbit OC2; FEBS Ltrs.; 1995; 357; 129-134.

Danheiser; Genetic Engineering News; 1995; 15/17; 1-1 and 35-36.

Sridevi, et al; "Some reactions and rearrangements of isoxazol-3-carbonyl azides and hydrazides"; Indian J. of Chem; 1990; 29B/2; 182-183.

Hill, et al.; "Inhibition of Bone Resorption by Selective Inactivators of Cysteine Proteinases"; J of Cellular Biochemistry; 1994; 56; 118-130.

McGrath, et al.; J of Med Chem; 1992; 35/23; 4279-4283.

Palmer, et al; J of Med Chem; 1995; 38/17; 3193-3196.

McConnell, et al.l; "Inhibition Studies of Some Serine and Thiol Proteinases by New Leupeptin Analogues"; J of Med Chem; 1993; 36; 1084-1089.

Bossard, et al; Journal of Bio. Chem.; 1996; 271/21; 12517-12524.

Everts, et al.; Degradation of Collagen in the Bone-Resorbing Compartment Underlying the Osteoclast Involves Both Cysteine-Proteinases and Matrix Metalloproteinases; Journal of Cellular Physiology; 1992; 150; 221-231.

Yamashita, et al; "Structure and Design of Potent and Selective Cathepsin K Inhibitors"; J. Amer. Chem. Soc.; 1997; 119; 11351-11352.

Han, et al.; Azatides: "Solution and Liquid Phase Syntheses of a New Peptidomimetic"; J. Amer. Chem. Soc.; 1986; 118/11; 2539-2544.

Tezuka, et al.; "Molecular Cloning of a Possible Cysteine Proteinase Predominatly Expressed in Osteoclasts"; J. Biolog. Chem.; 1994; 269/2; 1106-1109.

Powers, et al; "Reaction of Azapeptides with Human Leukocyte Elastase and Pricine Pancreatic Elastase"; J. Biol. Chem; 1984; 259/7; 4288-4294.

Gupton, et al.; "Reaction of Azapeptides with Chymotrypsin-like Enzymes"; J. Biol. Chem.; 1984; 259/7; 4279-4287.

McConnell, et al.; "New Leupeptin Analogues: Synthesis and Inhibition Data"; J. Med. Chem; 33; 86-93; 1990.

Winkler; "Molecular Molding Studies of "Flap Up" Mannosyl Cation Mimics"; J. Med. Chem.; 1996; 39; 4332-4334.

Drake, et al.; "Cathepsin K, but Not Cathepsins B, L, or S, Is Abundantly Expressed in Human Osteoclasts"; J. of Biological Chemistry; 1996; 217/21; 12511-12516.

Bromme, et al; "Human Cathepsin 02, a Matrix Protein-degrading Cysteine Protease Expressed in Osteoclasts"; J. of Biological Chemistry; 1996; 271/4; 2126-2132.

Velasco, et al; J. of Bio. Chem; 1994; 269/43; 27136-27142.

Lerner, et al; "Human Cystatin C, a Cysteine Proteinase Inhibitor, Inhibits Bone Resorption In Vitro Stimulated by Parathyroid Hormone and Parathyroid Hormone-Related Peptide of Malignancy"; J. of Bone and Mineral Research; 1992; 7/4; 433-439.

Borg, et al.; "Synthesis of 1,2,4-Oxadiazole-, 1,3,4-Oxadiazole-, and 1,2,4-Triazole- Derived Dipeptidomietics"; J. Org. Chem; 60; 3112-3120; 1995.

Afridi, et al.; "Heterocyclic Rearrangements. Part XIV. Attempts to Activate Ring-opening-Ring-closure Rearrangements with Carbon as the Central Atom"; J.C.S. Perkin Trans I; 1976; 3; 315-320.

Umezawa; "Structures and Activites of Protease Inhibitors of Microbial Origin"; Meth. Enzymol; 678-695; 1976.

Rasnick; Perspective in Drug Discovery & Design; 1996; 6; 48-63.

Potempa, et al.; "Host and Porphyromonas gingivalis proteinases in periodontitis: A biochemical model of infection and tissue distruction"; Perspective in Drug Discovery and Design; 1994; 2; 445-458.

Kosary, et al.; "Synthesis of pyridylthiazoles as antisecretory agents"; Pharmazie; 1989; 44/3; 191-193.

Thompson, et al.; "Design of potent and selective human cathepsin K Inhibitors that span the active site"; Proc. Natl. Acad. Sci.; 1997; 94; 14249-14254.

Tanner, et al; "Total Synthesis of Balanol, Part 1. Enantioselective Synthesis of the Hexaydroazepine Ring via Chiral Epoxides and Axiridines"; Tetrahedron; 1995; 51/21; 6061-6070.

Gray, et al.; Na-Ethyloxycarbonyl-a-Azaornithine Phen . . . ; Tetrahedron; 1977; 33; 837-840.

Boden, et al; "Total Synthesis of Lissoclinamide 5, a Cytotoxic Cyclic Peptide from the Tunicate Lissoclinum patella"; Tetrahedron. Ltrs.; 1994; 35/44; 8271-8274.

* cited by examiner

PROTEASE INHIBITORS

CROSS REFERENCE TO PRIOR APPLICATIONS

This application is a continuation of Ser. No. 10/239,343 filed 20 Sep. 2002 now U.S. Pat. No. 7,071,184, which is a 371 application of PCT/US01/07094 filed 7 Mar. 2001, which claims the benefit of U.S. application 60/191,000 filed 21 Mar. 2000, U.S. application 60/206,341 filed 23 May 2000, U.S. application 60/211,759 filed 14 Jun. 2000, and U.S. application 60/217,445 filed 10 Jul. 2000.

FIELD OF THE INVENTION

This invention relates in general to $C_{1-6}$alkyl-4-amino-azepan-3-one protease inhibitors, particularly such inhibitors of cysteine and serine proteases, more particularly compounds which inhibit cysteine proteases, even more particularly compounds which inhibit cysteine proteases of the papain superfamily, yet more particularly compounds which inhibit cysteine proteases of the cathepsin family, most particularly compounds which inhibit cathepsin K. Such compounds are particularly useful for treating diseases in which cysteine proteases are implicated, especially diseases of excessive bone or cartilage loss, e.g., osteoporosis, periodontitis, and arthritis; and certain parasitic diseases, e.g., malaria.

BACKGROUND OF THE INVENTION

Cathepsins are a family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J. Biol. Chem.* 271, 12517-12524; Drake, F. H., et al., (1996) *J. Biol.* Chem. 271, 12511-12516; Bromme, D., et al., (1996) *J. Biol. Chem.* 271, 2126-2132.

Cathepsin K has also been variously denoted as cathepsin O or cathepsin O2 in the literature. The designation cathepsin K is considered to be the most appropriate one.

Cathepsins function in the normal physiological process of protein degradation in animals, including humans, e.g., in the degradation of connective tissue. However, elevated levels of these enzymes in the body can result in pathological conditions leading to disease. Thus, cathepsins have been implicated as causative agents in various disease states, including but not limited to, infections by *pneumocystis carinii, trypsanoma cruzi, trypsanoma brucei brucei*, and *Crithidia fusiculata*; as well as in schistosomiasis, malaria, tumor metastasis, metachromatic leukodystrophy, muscular dystrophy, amytrophy, and the like. See International Publication Number WO 94/04172, published on Mar. 3, 1994, and references cited therein. See also European Patent Application EP 0 603 873 A1, and references cited therein. Two bacterial cysteine proteases from *P. gingivallis*, called gingipains, have been implicated in the pathogenesis of gingivitis. Potempa, J., et al. (1994) *Perspectives in Drug Discovery and Design*, 2, 445-458.

Cathepsin K is believed to play a causative role in diseases of excessive bone or cartilage loss. Bone is composed of a protein matrix in which spindle- or plate-shaped crystals of hydroxyapatite are incorporated. Type I collagen represents the major structural protein of bone comprising approximately 90% of the protein matrix. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodelling at discrete foci throughout life. These foci, or remodelling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive membrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

Several published studies have demonstrated that inhibitors of cysteine proteases are effective at inhibiting osteoclast-mediated bone resorption, and indicate an essential role for a cysteine proteases in bone resorption. For example, Delaisse, et al., *Biochem. J.*, 1980, 192, 365, disclose a series of protease inhibitors in a mouse bone organ culture system and suggest that inhibitors of cysteine proteases (e.g., leupeptin, Z-Phe-Ala-CHN$_2$) prevent bone resorption, while serine protease inhibitors were ineffective. Delaisse, et al., *Biochem. Biophys. Res. Commun.*, 1984, 125, 441, disclose that E-64 and leupeptin are also effective at preventing bone resorption in vivo, as measured by acute changes in serum calcium in rats on calcium deficient diets. Lerner, et al., *J. Bone Min. Res.*, 1992, 7, 433, disclose that cystatin, an endogenous cysteine protease inhibitor, inhibits PTH stimulated bone resorption in mouse calvariae. Other studies, such as by Delaisse, et al., *Bone*, 1987, 8, 305, Hill, et al., *J. Cell. Biochem.*, 1994, 56, 118, and Everts, et al., *J. Cell. Physiol.*, 1992, 150, 221, also report a correlation between inhibition of cysteine protease activity and bone resorption. Tezuka, et al., *J. Biol. Chem.*, 1994, 269, 1106, Inaoka, et al., *Biochem. Biophys. Res. Commun.*, 1995, 206, 89 and Shi, et al., *FEBS Lett.*, 1995, 357, 129 disclose that under normal conditions cathepsin K, a cysteine protease, is abundantly expressed in osteoclasts and may be the major cysteine protease present in these cells.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

Several cysteine protease inhibitors are known. Palmer, (1995) *J. Med. Chem.*, 38, 3193, disclose certain vinyl sulfones which irreversibly inhibit cysteine proteases, such as the cathepsins B, L, S, O2 and cruzain. Other classes of compounds, such as aldehydes, nitriles, α-ketocarbonyl compounds, halomethyl ketones, diazomethyl ketones, (acyloxy) methyl ketones, ketomethylsulfonium salts and epoxy succinyl compounds have also been reported to inhibit cysteine proteases. See Palmer, id, and references cited therein.

U.S. Pat. No. 4,518,528 discloses peptidyl fluoromethyl ketones as irreversible inhibitors of cysteine protease. Published International Patent Application No. WO 94/04172, and European Patent Application Nos. EP 0 525 420 A1, EP 0 603 873 A1, and EP 0 611 756 A2 describe alkoxymethyl and mercaptomethyl ketones which inhibit the cysteine proteases cathepsins B, H and L. International Patent Application No. PCT/US94/08868 and and European Patent Application No. EP 0 623 592 A1 describe alkoxymethyl and mercaptomethyl ketones which inhibit the cysteine protease IL-1βconvertase. Alkoxymethyl and mercaptomethyl ketones have also been described as inhibitors of the serine protease kininogenase (International Patent Application No. PCT/GB91/01479).

Azapeptides which are designed to deliver the azamino acid to the active site of serine proteases, and which possess a good leaving group, are disclosed by Elmore et al., *Biochem. J.*, 1968, 107, 103, Garker et al., *Biochem. J.*, 1974, 139, 555, Gray et al., *Tetrahedron*, 1977, 33, 837, Gupton et al., *J. Biol. Chem.*, 1984, 259, 4279, Powers et al., *J. Biol. Chem.*, 1984, 259, 4288, and are known to inhibit serine proteases. In addition, *J. Med. Chem.*, 1992, 35, 4279, discloses certain azapeptide esters as cysteine protease inhibitors.

Antipain and leupeptin are described as reversible inhibitors of cysteine protease in McConnell et al., *J. Med. Chem.*, 33, 86; and also have been disclosed as inhibitors of serine protease in Umezawa et al., 45 *Meth. Enzymol.* 678. E64 and its synthetic analogs are also well-known cysteine protease inhibitors (Barrett, *Biochem. J.*, 201, 189, and Grinde, *Biochem. Biophys. Acta*, 701, 328).

1,3-diamido-propanones have been described as analgesic agents in U.S. Pat. Nos. 4,749,792 and 4,638,010.

Thus, a structurally diverse variety of protease inhibitors have been identified. However, these known inhibitors are not considered suitable for use as therapeutic agents in animals, especially humans, because they suffer from various shortcomings. These shortcomings include lack of selectivity, cytotoxicity, poor solubility, and overly rapid plasma clearance. A need therefore exists for methods of treating diseases caused by pathological levels of proteases, particularly cysteine proteases, more particularly cathepsins, most particularly cathepsin K, and for novel inhibitor compounds useful in such methods.

We have now discovered a novel class of $C_{1-6}$alkyl-4-amino-azepan-3-one compounds which are protease inhibitors, most particularly of cathepsin K.

SUMMARY OF THE INVENTION

An object of the present invention is to provide $C_{1-6}$alkyl-4-amino-azepan-3-one carbonyl protease inhibitors, particularly such inhibitors of cysteine and serine proteases, more particularly such compounds which inhibit cysteine proteases, even more particularly such compounds which inhibit cysteine proteases of the papain superfamily, yet more particularly such compounds which inhibit cysteine proteases of the cathepsin family, most particularly such compounds which inhibit cathepsin K, and which are useful for treating diseases which may be therapeutically modified by altering the activity of such proteases.

Accordingly, in the first aspect, this invention provides a compound according to Formula I.

In another aspect, this invention provides a pharmaceutical composition comprising a compound according to Formula I and a pharmaceutically acceptable carrier, diluent or excipient.

In yet another aspect, this invention provides intermediates useful in the preparation of the compounds of Formula I.

In still another aspect, this invention provides a method of treating diseases in which the disease pathology may be therapeutically modified by inhibiting proteases, particularly cysteine and serine proteases, more particularly cysteine proteases, even more particularly cysteine proteases of the papain superfamily, yet more particularly cysteine proteases of the cathepsin family, most particularly cathepsin K.

In a particular aspect, the compounds of this invention are especially useful for treating diseases characterized by bone loss, such as osteoporosis and gingival diseases, such as gingivitis and periodontitis, or by excessive cartilage or matrix degradation, such as osteoarthritis and rheumatoid arthritis; and for treating certain parasitic diseases, such as malaria.

DETAILED DESCRIPTION OF THE INVENTION

The present invention provides compounds of Formula I:

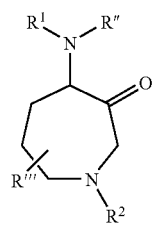

wherein:

$R^1$ is selected from the group consisting of:

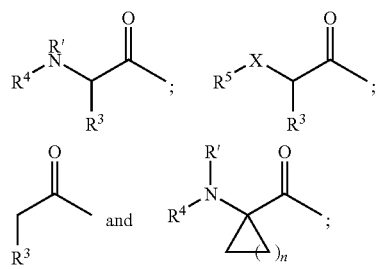

$R^2$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^9C(O)$—, $R^9C(S)$—, $R^9SO_2$—, $R^9OC(O)$—, $R^9R^{11}NC(O)$—, $R^9R^{11}NC(S)$—, $R^9(R^{11})NSO_2$—

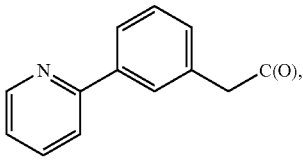

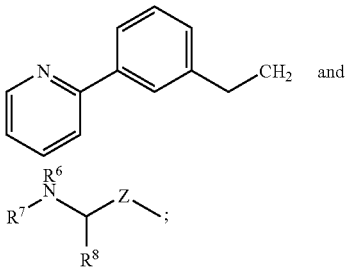

R³ is selected from the group consisting of: H, C$_{1-6}$alkyl, C$_{3-6}$cycloalkyl-C$_{0-6}$alkyl, C$_{2-6}$alkenyl, C$_{2-6}$alkynyl, HetC$_{0-6}$alkyl, ArC$_{0-6}$alkyl, Ar—ArC$_{0-6}$alkyl, Ar—HetC$_{0-6}$alkyl, Het-ArC$_{0-6}$alkyl, and Het-HetC$_{0-6}$alkyl;

R³ and R' may be connected to form a pyrrolidine, piperidine or morpholine ring;

R⁴ is selected from the group consisting of: H, C$_{1-6}$alkyl, C$_{3-6}$cycloalkyl-C$_{0-6}$alkyl, Ar—C$_{0-6}$alkyl, Het-C$_{0-6}$alkyl, R⁵C(O)—, R⁵C(S)—, R⁵SO$_2$—, R⁵OC(O)—, R⁵R¹²NC(O)—, and R⁵R¹²NC(S)—;

R⁵ is selected from the group consisting of: H, C$_{1-6}$alkyl, C$_{2-6}$alkenyl, C$_{2-6}$alkynyl, C$_{3-6}$cycloalkyl-C$_{0-6}$alkyl, C$_{2-6}$alkanonyl, Ar—C$_{0-6}$alkyl and Het-C$_{0-6}$alkyl;

R⁶ is selected from the group consisting of: H, C$_{1-6}$alkyl, Ar—C$_{0-6}$alkyl, and Het-C$_{0-6}$alkyl;

R⁷ is selected from the group consisting of: H, C$_{1-6}$alkyl, C$_{3-6}$cycloalkyl-C$_{0-6}$alkyl, Ar—C$_{0-6}$alkyl, Het-C$_{0-6}$alkyl, R¹⁰C(O)—, R¹⁰C(S)—, R¹⁰SO$_2$—, R¹⁰OC(O)—, R¹⁰R¹³NC(O)—, and R¹⁰R¹³NC(S)—;

R⁸ is selected from the group consisting of: H, C$_{1-6}$alkyl, C$_{2-6}$alkenyl, C$_{2-6}$alkynyl, HetC$_{0-6}$alkyl and ArC$_{0-6}$alkyl;

R⁹ is selected from the group consisting of: C$_{1-6}$alkyl, C$_{3-6}$cycloalkyl-C$_{0-6}$alkyl, Ar—C$_{0-6}$alkyl and Het-C$_{0-6}$alkyl;

R¹⁰ is selected from the group consisting of: C$_{1-6}$alkyl, C$_{3-6}$cycloalkyl-C$_{0-6}$alkyl, Ar—C$_{0-6}$alkyl and Het-C$_{0-6}$alkyl;

R¹¹ is selected from the group consisting of: H, C$_{1-6}$alkyl, Ar—C$_{0-6}$alkyl, C$_{3-6}$cycloalkyl-C$_{0-6}$alkyl, and Het-C$_{0-6}$alkyl;

R¹² is selected from the group consisting of: H, C$_{1-6}$alkyl, Ar—C$_{0-6}$alkyl, and Het-C$_{0-6}$alkyl;

R¹³ is selected from the group consisting of: H, C$_{1-6}$alkyl, Ar—C$_{0-6}$alkyl, and Het-C$_{0-6}$alkyl;

R' is selected from the group consisting of: H, C$_{1-6}$alkyl, Ar—C$_{0-6}$alkyl, and Het-C$_{0-6}$alkyl;

R" is selected from the group consisting of: H, C$_{1-6}$alkyl, Ar—C$_{0-6}$alkyl, or Het-C$_{0-6}$alkyl;

R''' is C$_{1-6}$alkyl;

X is selected from the group consisting of: CH$_2$, S, and O;

Z is selected from the group consisting of: C(O) and CH$_2$;

n is an integer from 1 to 5;

and pharmaceutically acceptable salts, hydrates and solvates thereof.

In compounds of Formula I, when R¹ is

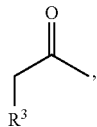

R³ is selected from the group consisting of: H, C$_{1-6}$alkyl, C$_{3-6}$cycloalkyl-C$_{0-6}$alkyl, C$_{2-6}$alkenyl, C$_{2-6}$alkynyl, Het-C$_{0-6}$alkyl, Ar—C$_{0-6}$alkyl, Ar—ArC$_{0-6}$alkyl, Ar—HetC$_{0-6}$alkyl, Het-ArC$_{0-6}$alkyl, and Het-HetC$_{0-6}$alkyl. Preferably, R³ is Ar—ArC$_{0-6}$alkyl, more preferably 3-isobutyl biphenyl.

In compounds of Formula I, when R¹ is

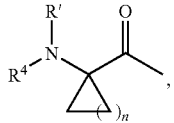

n is preferably 4, to provide 1-amino-1-acyl cyclohexane compounds. The cycloalkyl ring may be unsubstituted or substituted with one or more of C$_{1-6}$alkyl, C$_{3-6}$cycloalkyl-C$_{0-6}$ alkyl, C$_{2-6}$alkenyl, C$_{2-6}$alkynyl, HetC$_{0-6}$alkyl, ArC$_{0-6}$alkyl, or halogen.

The cycloalkyl ring is more preferably unsubstituted.

In compounds of Formula I, when R¹ is

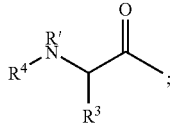

R³ is selected from the group consisting of: H, C$_{1-6}$alkyl, C$_{3-6}$cycloalkyl-C$_{0-6}$alkyl, C$_{2-6}$alkenyl, C$_{2-6}$alkynyl, Het-C$_{0-6}$alkyl, Ar—C$_{0-6}$alkyl, Ar—ArC$_{0-6}$alkyl, Ar—HetC$_{0-6}$alkyl, Het-ArC$_{0-6}$alkyl, and Het-HetC$_{0-6}$alkyl;

R³ is preferably selected from the group consisting of: H, C$_{3-6}$cycloalkyl-C$_{0-6}$alkyl, Ar—C$_{0-6}$alkyl, and C$_{1-6}$alkyl;

R³ is more preferably selected from the group consisting of:

H, methyl, ethyl, n-propyl, prop-2-yl, n-butyl, isobutyl, but-2-yl, cyclopropylmethyl, cyclohexylmethyl, 2-methanesulfinyl-ethyl, 1-hydroxyethyl, toluyl, naphthalen-2-ylmethyl, benzyloxymethyl, and hydroxymethyl.

R³ is even more preferably selected from the group consisting of: toluyl, isobutyl and cyclohexylmethyl.

R³ is most preferably isobutyl.

R⁴ is selected from the group consisting of: H, C$_{1-6}$alkyl, C$_{3-6}$cycloalkyl-C$_{0-6}$alkyl, Ar—C$_{0-6}$alkyl, Het-C$_{0-6}$alkyl, R⁵C(O)—, R⁵C(S)—, R⁵SO$_2$—, R⁵OC(O)—, R⁵R¹²NC(O)—, and R⁵R¹²NC(S)—.

R⁴ is preferably selected from the group consisting of: R⁵OC(O)—, R⁵C(O)— and R⁵SO$_2$—.

R⁴ is most preferably R⁵C(O)—.

In some embodiments, R⁴ is preferably methanesulfonyl.

R⁵ is selected from the group consisting of: H, C$_{1-6}$alkyl, C$_{2-6}$alkenyl, C$_{2-6}$alkynyl, C$_{3-6}$cycloalkyl-C$_{0-6}$alkyl, C$_{2-6}$alkanonyl, Ar—C$_{0-6}$alkyl or Het-C$_{0-6}$alkyl.

Preferably $R^5$ is selected from the group consisting of: $C_{1-6}$alkyl, $C_{2-6}$alkenyl, $C_{3-6}$cycloalkyl-$C_{0-6}$alkyl, $C_{2-6}$alkanonyl, Ar—$C_{0-6}$alkyl and Het-$C_{0-6}$alkyl.

More preferably, and especially when $R^4$ is $R^5C(O)$—, $R^5$ is selected from the group consisting of:

methyl, especially halogenated methyl, more especially trifluoromethyl, especially $C_{1-6}$alkoxy and aryloxy substituted methyl, more especially phenoxy-methyl, 4-fluorophenoxy-methyl, especially heterocycle substituted methyl, more especially 2-thiophenyl-methyl;

butyl, especially aryl substituted butyl, more especially 4-(4-methoxy)phenyl-butyl;

isopentyl;

cyclohexyl;

pentanonyl, especially 4-pentanonyl;

butenyl, especially aryl substituted butenyl, more especially 4,4-bis(4-methoxyphenyl)-but-3-enyl;

phenyl, especially phenyl substituted with one or more halogens, more especially 3,4-dichlorophenyl and 4-fluorophenyl, especially phenyl substituted with one or more $C_{1-6}$ alkoxy or aryloxy groups, more especially 3,4-dimethoxyphenyl, 3-benzyloxy-4-methoxy-phenyl, especially phenyl substituted with one or more sulfonyl groups, more especially 4-methanesulfonyl-phenyl;

benzyl;

naphthalenyl, especially naphthylen-2-yl;

benzo[1,3]dioxolyl, especially benzo[1,3]dioxol-5-yl, furanyl, especially furan-2-yl, especially substituted furanyl, such as 5-nitro-furan-2-yl, 5-(4-nitrophenyl)-furan-2-yl, 5-(3-trifluoromethyl-phenyl)-furan-2-yl, more especially halogen substituted furanyl, even more especially 5-bromofuran-2-yl, more especially aryl substituted furanyl, even more especially 5-(4-chloro-phenyl)-furan-2-yl;

tetrahydrofuranyl, especially tetrahydrofuran-2-yl;

benzofuranyl, especially benzofuran-2-yl, and especially $C_{1-6}$alkoxy substituted benzofuranyl, more especially 5-(2-piperazin-4-carboxylic acid tert-butyl ester-ethoxy)benzofuran-2-yl, 5-(2-morpholino-4-yl-ethoxy)-benzofuran-2-yl, 5-(2-piperazin-1-yl-ethoxy)benzofuran-2-yl, 5-(2-cyclohexyl-ethoxy)-benzofuran-2-yl; 7-methoxy-benzofuran-2-yl, 5-methoxy-benzofura-2-yl, 5,6-dimethoxy-benzofuran-2-yl, especially halogen substituted benzofuranyl, more especially 5-fluoro-benzofuran-2-yl, 5,6-difluoro-benzofuran-2-yl, especially $C_{1-6}$alkyl substituted benzofuranyl, most especially 3-methyl-benzofuran-2-yl;

benzo[b]thiophenyl, especially benzo[b]thiophen-2-yl; especially $C_{1-6}$alkoxy substituted benzo[b]thiophenyl, more especially 5,6-dimethoxy-benzo[b]thiophen-2-yl;

quinolinyl, especially quinolin-2-yl, quinolin-3-yl, quinolin-4-yl, quinolin-6-yl, and quinolin-8-yl;

quinoxalinyl, especially quinoxalin-2-yl;

1,8 naphthyridinyl, especially 1,8 naphthyridin-2-yl;

indolyl, especially indol-2-yl, especially indol-6-yl, indol-5-yl, especially $C_{1-6}$alkyl substituted indolyl, more especially N-methyl-indol-2-yl;

pyridinyl, especially pyridin-2-yl, pyridin-5-yl, especially 1-oxy-pyridin-2-yl, especially $C_{1-6}$alkyl substituted pyridinyl, more especially 2-methyl-pyridin-5-yl;

furo[3,2-b]pyridinyl, especially furo[3,2-b]pyridin-2-yl, and $C_{1-6}$alkyl substituted furo[3,2-b]pyridinyl, especially 3-methyl-furo[3,2-b]pyridin-2-yl;

thiophenyl, especially thiophen-3-yl, especially $C_{1-6}$alkyl substituted thiophenyl, more especially 5-methyl-thiophen-2-yl, especially halogen substituted thiophenyl, more especially 4,5-dibromo-thiophen-2-yl;

thieno[3,2-b]thiophene, especially thieno[3,2-b]thiophene-2-yl, more especially $C_{1-6}$alkyl substituted thieno[3,2-b]thiophene-2-yl, more especially 5-tert-butyl-3-methyl-thieno[3,2-b]thiophene-2-yl;

isoxazolyl, especially isoxazol-4-yl, especially $C_{1-6}$alkyl substituted isoxazolyl, more especially 3,5-dimethyl-isoxazol-4-yl; and oxazolyl, especially oxazol-4-yl, more especially 5-methyl-2-phenyl oxazol-4-yl, 2-phenyl-5-trifluoromethyl-oxazol-4-yl;

When $R^4$ is $R^5SO_2$, $R^5$ is preferably pyridin-2-yl or 1-oxopyridin-2-yl.

R' is selected from the group consisting of: H, $C_{1-6}$alkyl, Ar—$C_{0-6}$alkyl, and Het-$C_{0-6}$alkyl.

Preferably R' selected from the group consisting of: H and naphthalen-2-yl-methyl.

Most preferably R' is H.

R" selected from the group consisting of: H, $C_{1-6}$alkyl, Ar—$C_{0-6}$alkyl, and Het-$C_{0-6}$alkyl.

Most preferably R" is H.

R''' is:

$C_{1-6}$alkyl, especially selected from the group consisting of: methyl, ethyl, propyl, butyl, pentyl and hexyl, more especially methyl;

preferably 5-, 6- or 7-$C_{1-6}$alkyl, especially selected from the group consisting of: 5-, 6- or 7-methyl, -ethyl, -propyl, -butyl, -pentyl and -hexyl, more especially 5-, 6- or 7-methyl;

more preferably 6- or 7-$C_{1-6}$alkyl, especially selected from the group consisting of: 6- or 7-methyl, -ethyl, -propyl, -butyl, -pentyl and -hexyl, more especially 6- or 7-methyl;

yet more preferably cis-7-$C_{1-6}$alkyl as shown in Formula Ia:

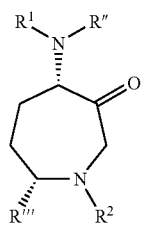

Ia wherein R''' is $C_{1-6}$alkyl, especially selected from the group consisting of: methyl, ethyl, propyl, butyl, pentyl and hexyl;

most preferably cis-7-methyl, as shown in Formula Ia wherein R''' is methyl.

In compounds of Formula I, $R^2$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^9C(O)$—, $R^9C(S)$—, $R^9SO_2$—, $R^9OC(O)$—, $R^9R^{11}NC(O)$—, $R^9R^{11}NC(S)$—, $R^9R^{11}NSO_2$—,

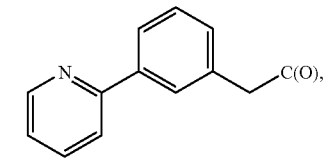

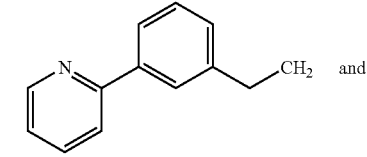

and

-continued

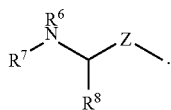

Preferably $R^2$ is selected from the group consisting of: Ar—$C_{0-6}$alkyl, $R^9C(O)$—, $R^9SO_2$, $R^9R^{11}NC(O)$—, and

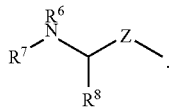

More preferably, $R^2$ is selected from the group consisting of: Ar—$C_{0-6}$alkyl, $R^9C(O)$—, and $R^9SO_2$.

Most preferably $R^2$ is $R^9SO_2$.

In such embodiments:

$R^6$ is selected from the group consisting of: H, $C_{1-6}$alkyl, Ar—$C_{0-6}$alkyl, or Het-$C_{0-6}$alkyl, preferably H.

$R^7$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^{10}C(O)$—, $R^{10}C(S)$—, $R^{10}SO_2$—, $R^{10}OC(O)$—, $R^{10}R^{13}NC(O)$—, $R^{10}R^{13}NC(S)$—, $R^7$ is preferably $R^{10}OC(O)$.

$R^8$ is selected from the group consisting of: H, $C_{1-6}$alkyl, $C_{2-6}$alkenyl, $C_{2-6}$alkynyl, Het$C_{0-6}$alkyl and Ar$C_{0-6}$alkyl; preferably $C_{1-6}$alkyl, more preferably isobutyl.

$R^9$ is selected from the group consisting of: $C_{1-6}$alkyl, $C_{3-6}$cycloalkyl-$C_{0-6}$alkyl, Ar—$C_{0-6}$alkyl, and Het-$C_{0-6}$alkyl.

More preferably, $R^9$ is selected from the group consisting of:

methyl;

ethyl, especially $C_{1-6}$alkyl-substituted ethyl, more especially 2-cyclohexyl-ethyl;

butyl, especially $C_{1-6}$butyl, more especially 3-methylbutyl;

tert-butyl, particularly when $R^2$ is $R^9OC(O)$;

isopentyl;

phenyl, especially halogen substituted phenyl, more especially 3,4-dichlorophenyl, 4-bromophenyl, 2-fluorophenyl, 4-fluorophenyl, 3-chlorophenyl, 4-chlorophenyl, especially $C_{1-6}$alkoxy phenyl, more especially 3-methoxyphenyl, 4-methoxyphenyl, 3,4-dimethoxyphenyl, especially cyanophenyl, more especially 2-cyanophenyl;

toluyl, especially Het-substituted toluyl, more especially 3-(pyridin-2-yl)toluyl;

naphthylenyl, especially naphthylen-2-yl;

benzoyl, especially 2-benzoyl;

benzo[1,3]dioxolyl, especially benzo[1,3]dioxol-5-yl;

benzo[1,2,5]oxadiazolyl, especially benzo[1,2,5]oxadiazol-4-yl;

pyridinyl, especially pyridin-2-yl, pyridin-3-yl, especially 1-oxy-pyridinyl, more especially 1-oxy-pyridin-2-yl, 1-oxy-pyridin-3-yl; especially $C_{1-6}$alkylpyridinyl, more especially 3-methyl-pyridin-2-yl, 6-methyl-pyridin-2-yl, thiophene, especially thiophene-2-yl;

thiazolyl, especially thiazol-2-yl;

1H-imidazolyl, especially 1H-imidazol-2-yl, 1H-imidazol-4-yl, more especially $C_{1-6}$alkyl substituted imidazolyl, even more especially 1-methyl-1H-imidazol-2-yl, 1-methyl-1H-imidazol-4-yl;

1H-[1,2,4]triazolyl, especially 1H-[1,2,4]triazol-3-yl, more especially $C_{1-6}$alkyl substituted 1H-[1,2,4]triazolyl, even more especially 5-methyl-1H-[1,2,4]triazol-3-yl; and quinolinyl.

When $R^2$ is $R^9SO_2$, $R^9$ is most preferably selected from the group consisting of: pyridin-2-yl and 1-oxy-pyridin-2-yl.

$R^{10}$ is selected from the group consisting of: $C_{1-6}$alkyl, $C_{3-6}$cycloalkyl-$C_{0-6}$alkyl, Ar—$C_{0-6}$alkyl or Het-$C_{0-6}$alkyl; preferably $C_{1-6}$alkyl, Ar—$C_{0-6}$alkyl and Het-$C_{0-6}$alkyl.

Z is selected from the group consisting of: C(O) and $CH_2$.

$R^2$ is also preferably:

H;

toluyl;

aryl substituted ethyl, especially 2-phenyl ethyl, 2-[3-(pyridin-2-yl)phenyl]ethyl.

Compounds of Formula I where R" is H and and R'" is methyl are preferred.

More preferred are compounds of Formula I wherein:

$R^1$ is

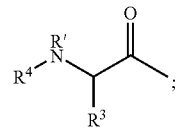

$R^2$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^9C(O)$—, $R^9C(S)$—, $R^9SO_2$—, $R^9OC(O)$—, $R^9R^{11}NC(O)$—, $R^9R^{11}NC(S)$—, $R^9(R^{11})NSO_2$—,

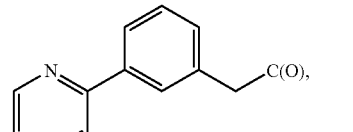

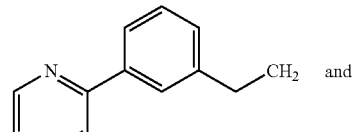

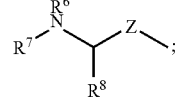

$R^3$ is selected from the group consisting of: H, $C_{1-6}$alkyl, $C_{3-6}$cycloalkyl-$C_{0-6}$alkyl, and Ar—$C_{0-6}$alkyl;

$R^4$ is selected from the group consisting of: $R^5C(O)$—, $R^5SO_2$—, and $R^5OC(O)$—;

$R^5$ is selected from the group consisting of: $C_{1-6}$alkyl, $C_{2-6}$alkenyl, $C_{3-6}$cycloalkyl-$C_{0-6}$alkyl, $C_{2-6}$alkanonyl, Ar—$C_{0-6}$alkyl and Het-$C_{0-6}$alkyl;

$R^6$ is selected from the group consisting of: H, $C_{1-6}$alkyl, Ar—$C_{0-6}$alkyl, and Het-$C_{0-6}$alkyl;

$R^7$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^{10}C(O)$—, $R^{10}C(S)$—, $R^{10}SO_2$—, $R^{10}OC(O)$—, $R^{10}R^{13}NC(O)$—, and $R^{10}R^{13}NC(S)$—;

$R^8$ is selected from the group consisting of: H, $C_{1-6}$alkyl, $C_{2-6}$alkenyl, $C_{2-6}$alkynyl, Het$C_{0-6}$alkyl and Ar$C_{0-6}$alkyl;

$R^9$ is selected from the group consisting of: $C_{1-6}$alkyl, $C_{3-6}$cycloalkyl-$C_{0-6}$alkyl, Ar—$C_{0-6}$alkyl and Het-$C_{0-6}$alkyl;

$R^{10}$ is selected from the group consisting of: $C_{1-6}$alkyl, $C_{3-6}$cycloalkyl-$C_{0-6}$alkyl, Ar—$C_{0-6}$alkyl and Het-$C_{0-6}$alkyl;

$R^{11}$ is selected from the group consisting of: H, $C_{1-6}$alkyl, Ar—$C_{0-6}$alkyl, $C_{3-6}$cycloalkyl-$C_{0-6}$alkyl, and Het-$C_{0-6}$alkyl;

$R^{12}$ is selected from the group consisting of: H, $C_{1-6}$alkyl, Ar—$C_{0-6}$alkyl, and Het-$C_{0-6}$alkyl;

$R^{13}$ is selected from the group consisting of: H, $C_{1-6}$alkyl, Ar—$C_{0-6}$alkyl, and Het-$C_{0-6}$alkyl;

R' is H;

R" is H;

R'" is selected from the group consisting of:

$C_{1-6}$alkyl, especially selected from the group consisting of: methyl, ethyl, propyl, butyl, pentyl and hexyl, more especially methyl;

preferably 5-, 6- or 7-$C_{1-6}$alkyl, especially selected from the group consisting of: 5-, 6- or 7-methyl, -ethyl, -propyl, -butyl, -pentyl and -hexyl, more especially 5-, 6- or 7-methyl;

more preferably 6- or 7-$C_{1-6}$alkyl, especially selected from the group consisting of: 6- or 7-methyl, -ethyl, -propyl, -butyl, -pentyl and -hexyl, more especially 6- or 7-methyl;

yet more preferably cis-7-$C_{1-6}$alkyl as shown in Formula Ia:

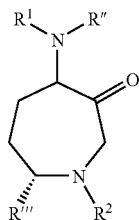

Ia wherein R'" is $C_{1-6}$alkyl, especially selected from the group consisting of: methyl, ethyl, propyl, butyl, pentyl and hexyl;

most preferably cis-7-methyl, as shown in Formula Ia wherein R'" is methyl; and

Z is selected from the group consisting of: C(O) and CH$_2$.

Particularly preferred are such compounds wherein $R^3$ is isobutyl.

Still more preferred are compounds of Formula I wherein: $R^1$ is

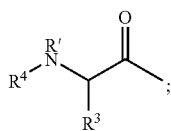

$R^2$ is selected from the group consisting of: Ar—$C_{0-6}$alkyl, $R^9$C(O)—, $R^9$SO$_2$, $R^9R^{11}$NC(O)—, and

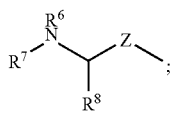

$R^3$ is selected from the group consisting of: H, $C_{1-6}$alkyl, $C_{3-6}$cycloalkyl-$C_{0-6}$alkyl, and Ar—$C_{0-6}$alkyl;

$R^4$ is selected from the group consisting of: $R^5$OC(O)—, $R^5$C(O)— and $R^5$SO$_2$—;

$R^5$ is selected from the group consisting of: $C_{1-6}$alkyl, $C_{2-6}$alkenyl, $C_{3-6}$cycloalkyl-$C_{0-6}$alkyl, $C_{2-6}$alkanonyl, Ar—$C_{0-6}$alkyl and Het-$C_{0-6}$alkyl;

$R^6$ is H;

$R^7$ is $R^{10}$OC(O);

$R^8$ is $C_{1-6}$alkyl;

$R^9$ is selected from the group consisting of: $C_{1-6}$alkyl, $C_{3-6}$cycloalkyl-$C_{0-6}$alkyl, Ar—$C_{0-6}$alkyl and Het-$C_{0-6}$alkyl;

$R^{10}$ is selected from the group consisting of: $C_{1-6}$alkyl, Ar—$C_{0-6}$alkyl and Het-$C_{0-6}$alkyl;

$R^{11}$ is selected from the group consisting of: $C_{1-6}$alkyl, $C_{3-6}$cycloalkyl-$C_{0-6}$alkyl, Ar—$C_{0-6}$alkyl and Het-$C_{0-6}$alkyl;

R' is H;

R" is H;

R'" is methyl, preferably 5-, 6- or 7-methyl, more preferably 6- or 7-methyl, most preferably cis-7-methyl, as shown in Formula Ia:

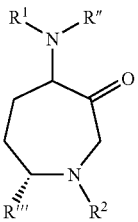

Ia wherein R'" is methyl; and

Z is selected from the group consisting of: C(O) and CH$_2$.

Even more preferred are such compounds of Formula I wherein $R^2$ is selected from the group consisting of: Ar—$C_{0-6}$alkyl, $R^9$C(O)—, $R^9$SO$_2$.

Yet more preferred are compounds of Formula I wherein:

$R^1$ is

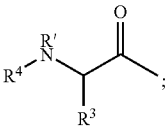

$R^2$ is selected from the group consisting of: Ar—$C_{0-6}$alkyl, $R^9$C(O)— and $R^9$SO$_2$;

$R^3$ is selected from the group consisting of: H, methyl, ethyl, n-propyl, prop-2-yl, n-butyl, isobutyl, but-2-yl, cyclopropylmethyl, cyclohexylmethyl, 2-methanesulfinyl-ethyl, 1-hydroxyethyl, toluyl, naphthalen-2-ylmethyl, benzyloxymethyl, and hydroxymethyl;

$R^4$ is $R^5$C(O)—;

$R^5$ is selected from the group consisting of: methyl, especially halogenated methyl, more especially trifluoromethyl, especially $C_{1-6}$alkoxy and aryloxy substituted methyl, more especially phenoxy-methyl, 4-fluoro-phenoxy-methyl, especially heterocycle substituted methyl, more especially 2-thiophenyl-methyl;

butyl, especially aryl substituted butyl, more especially 4-(4-methoxy)phenyl-butyl;

isopentyl;

cyclohexyl;

pentanonyl, especially 4-pentanonyl;

butenyl, especially aryl substituted butenyl, more especially 4,4-bis(4-methoxyphenyl)-but-3-enyl;

phenyl, especially phenyl substituted with one or more halogens, more especially 3,4-dichlorophenyl and 4-fluorophenyl, especially phenyl substituted with one or more $C_{1-6}$alkoxy or aryloxy groups, more especially 3,4-dimethoxy-phenyl, 3-benzyloxy-4-methoxy-phenyl, especially phenyl substituted with one or more sulfonyl groups, more especially 4-methanesulfonyl-phenyl;

benzyl;

naphthylen-2-yl;

benzo[1,3]dioxolyl, especially benzo[1,3]dioxol-5-yl, furanyl, especially furan-2-yl, especially substituted furanyl, such as 5-nitro-furan-2-yl, 5-(4-nitrophenyl)-furan-2-yl, 5-(3-trifluoromethyl-phenyl)-furan-2-yl, more especially halogen substituted furanyl, even more especially 5-bromo-furan-2-yl, more especially aryl substituted furanyl, even more especially 5-(4-chloro-phenyl)-furan-2-yl;

tetrahydrofuran-2-yl;

benzofuranyl, especially benzofuran-2-yl, and especially $C_{1-6}$alkoxy substituted benzofuranyl, more especially 5-(2-piperazin-4-carboxylic acid tert-butyl ester-ethoxy)benzofuran-2-yl, 5-(2-morpholino-4-yl-ethoxy)-benzofuran-2-yl, 5-(2-piperazin-1-yl-ethoxy)benzofuran-2-yl, 5-(2-cyclohexyl-ethoxy)-benzofuran-2-yl, 7-methoxy-benzofuran-2-yl, 5-methoxy-benzofuran-2-yl, 5,6-dimethoxy-benzofuran-2-yl, especially halogen substituted benzofuranyl, more especially 5-fluoro-benzofuran-2-yl, 5,6-difluoro-benzofuran-2-yl, especially $C_{1-6}$alkyl substituted benzofuranyl, most especially 3-methyl-benzofuran-2-yl;

benzo[b]thiophenyl, especially benzo[b]thiophen-2-yl; especially $C_{1-6}$alkoxy substituted benzo[b]thiophenyl, more especially 5,6-dimethoxy-benzo[b]thiophen-2-yl;

quinolinyl, especially quinolin-2-yl, quinolin-3-yl, quinolin-4-yl, quinolin-6-yl, and quinolin-8-yl;

quinoxalinyl, especially quinoxalin-2-yl;

1,8 naphthyridinyl, especially 1,8 naphthyridin-2-yl;

indolyl, especially indol-2-yl, especially indol-6-yl, indol-5-yl, especially $C_{1-6}$alkyl substituted indolyl, more especially N-methyl-indol-2-yl;

pyridinyl, especially pyridin-2-yl, pyridin-5-yl, especially 1-oxy-pyridin-2-yl, especially $C_{1-6}$alkyl substituted pyridinyl, more especially 2-methyl-pyridin-5-yl;

furo[3,2-b]pyridinyl, especially furo[3,2-b]pyridin-2-yl, and $C_{1-6}$alkyl substituted furo[3,2-b]pyridinyl, especially 3-methyl-furo[3,2-b]pyridin-2-yl;

thiophenyl, especially thiophen-3-yl, especially $C_{1-6}$alkyl substituted thiophenyl, more especially 5-methyl-thiophen-2-yl, especially halogen substituted thiophenyl, more especially 4,5-dibromo-thiophen-2-yl;

thieno[3,2-b]thiophene, especially thieno[3,2-b]thiophene-2-yl, more especially $C_{1-6}$alkyl substituted thieno[3,2-b]thiophene-2-yl, more especially 5-tert-butyl-3-methyl-thieno[3,2-b]thiophene-2-yl;

isoxazolyl, especially isoxazol-4-yl, especially $C_{1-6}$alkyl substituted isoxazolyl, more especially 3,5-dimethyl-isoxazol-4-yl; and oxazolyl, especially oxazol-4-yl, more especially 5-methyl-2-phenyl oxazol-4-yl, 2-phenyl-5-trifluoromethyl-oxazol-4-yl;

$R^9$ is selected from the group consisting of:
methyl;
ethyl, especially $C_{1-6}$alkyl-substituted ethyl, more especially 2-cyclohexyl-ethyl;
butyl, especially $C_{1-6}$butyl, more especially 3-methylbutyl;
tert-butyl, particularly when $R^2$ is $R^9OC(O)$;
isopentyl;

phenyl, especially halogen substituted phenyl, more especially 3,4-dichlorophenyl, 4-bromophenyl, 2-fluorophenyl, 4-fluorophenyl, 3-chlorophenyl, 4-chlorophenyl, especially $C_{1-6}$alkoxy phenyl, more especially 3-methoxyphenyl, 4-methoxyphenyl, 3,4-dimethoxyphenyl, especially cyanophenyl, more especially 2-cyanophenyl;

toluyl, especially Het-substituted toluyl, more especially 3-(pyridin-2-yl)toluyl;

naphthylene, especially naphthyl-2-ene;

benzoyl, especially 2-benzoyl;

benzo[1,3]dioxolyl, especially benzo[1,3]dioxol-5-yl;

benzo[1,2,5]oxadiazolyl, especially benzo[1,2,5]oxadiazol-4-yl;

pyridinyl, especially pyridin-2-yl, pyridin-3-yl, especially 1-oxy-pyridinyl, more especially 1-oxy-pyridin-2-yl, 1-oxy-pyridin-3-yl; especially $C_{1-6}$alkylpyridinyl, more especially 3-methyl-pyridin-2-yl, 6-methyl-pyridin-2-yl, thiophenyl, especially thiophene-2-yl;

thiazolyl, especially thiazol-2-yl;

1H-imidazolyl, especially 1H-imidazol-2-yl(74), 1H-imidazol-4-yl, more especially $C_{1-6}$alkyl substituted imidazolyl, even more especially 1-methyl-1H-imidazol-2-yl, 1-methyl-1H-imidazol-4-yl; and 1H-[1,2,4]triazolyl, especially 1H-[1,2,4]triazol-3-yl, more especially $C_{1-6}$alkyl substituted 1H-[1,2,4]triazolyl, even more especially 5-methyl-1H-[1,2,4]triazol-3-yl; and quinolinyl;

R' is H;

R" is H; and

R''' is methyl, preferably 5-, 6- or 7-methyl, more preferably 6- or 7-methyl, most preferably cis-7-methyl, as shown in Formula Ia:

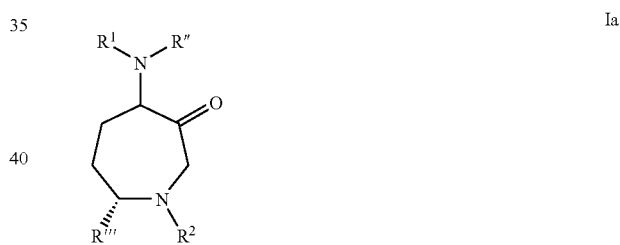

Ia wherein R''' is methyl.

Even yet more preferred are compounds of Formula I wherein:

$R^1$ is

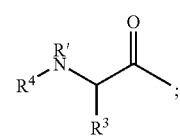

$R^2$ is $R^9SO_2$;
$R^3$ is $C_{1-6}$alkyl;
$R^4$ is $R^5C(O)$;
$R^5$ is Het-$C_{0-6}$alkyl;
$R^9$ is Het-$C_{0-6}$alkyl;
R' is H;
R" is H; and
R''' is selected from the group consisting of: 5-, 6- or 7-methyl, preferably 6- or 7-methyl, most preferably cis-7-methyl, as shown in Formula Ia:

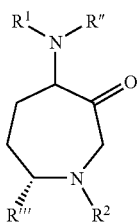

wherein R''' is methyl.

Still yet more preferred are compounds of Formula I wherein:

R¹ is

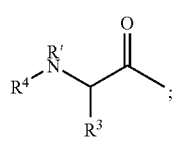

R² is R⁹SO₂;
R³ is isobutyl;
R⁴ is R⁵C(O);
R⁵ is selected from the group consisting of: 5-methoxybenzofuran-2-yl, benzo[b]thiophen-2-yl, 3-methyl-benzofuran-2-yl, thieno[3,2-b]thiophen-2-yl, benzofuran-2-yl, furo[3,2-b]pyridin-2-yl, and 3-methyl-furo[3,2-b]pyridin-2-yl; preferably benzofuran-2-yl, furo[3,2-b]pyridin-2-yl, and 3-methyl-furo[3,2-b]pyridin-2-yl; most preferably benzofuran-2-yl.
R⁹ is selected from the group consisting of: pyridin-2-yl and 1-oxy-pyridin-2-yl, preferably pyridin-2-yl.
R' is H;
R'' is H; and
R''' is selected from the group consisting of: 5-, 6- or 7-methyl, preferably 6- or 7-methyl, most preferably cis-7-methyl, as shown in Formula Ia:

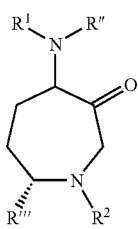

wherein R''' is methyl.

Compounds of Formula I selected from the following group are particularly preferred embodiments of the present invention:

5-methoxy-benzofuran-2-carboxylic acid {(S)-3-methyl-1-[(4S,6S)-6-methyl-3-oxo-1-(pyridine-2-sulfonyl)-azepan-4-ylcarbamoyl]-butyl}-amide:

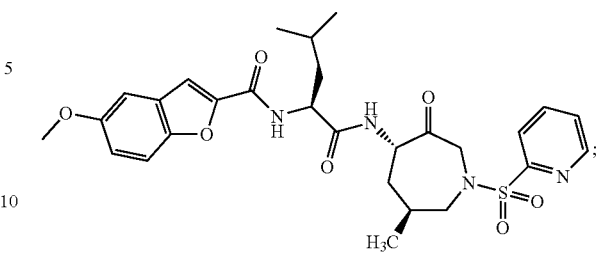

5-methoxy-benzofuran-2-carboxylic acid {(S)-3-methyl-1-[(4R,6R)-6-methyl-3-oxo-1-(pyridine-2-sulfonyl)-azepan-4-ylcarbamoyl]-butyl}-amide:

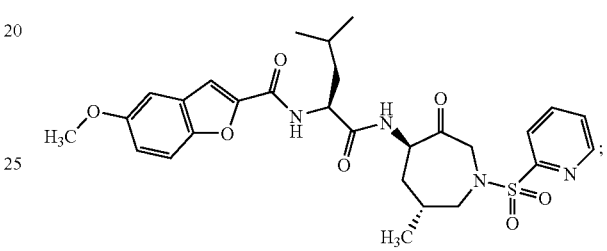

benzo[b]thiophene-2-carboxylic acid {(S)-1-[(4S,6S)-6-methyl-3-oxo-1-(pyridine-2-sulfonyl)-azepan-4-ylcarbamoyl]-3-methyl-butyl}-amide:

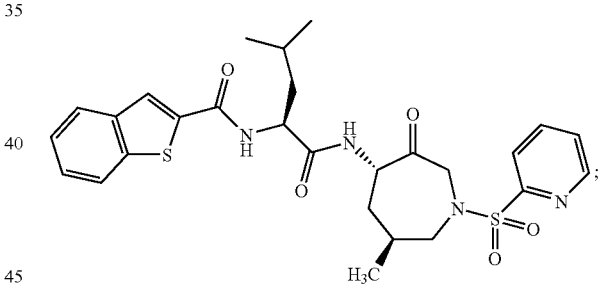

benzo[b]thiophene-2-carboxylic acid {(S)-1-[(4R,6R)-6-methyl-3-oxo-1-(pyridine-2-sulfonyl)-azepan-4-ylcarbamoyl]-3-methyl-butyl}-amide:

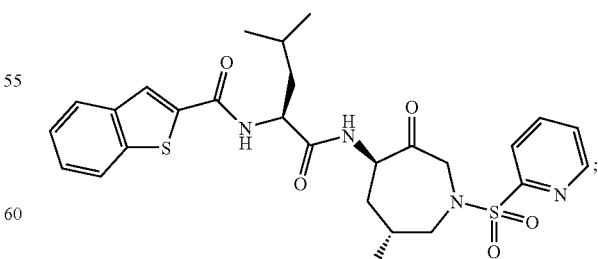

3-methyl-benzofuran-2-carboxylic acid {(S)-1-[(4S,6S)-6-methyl-3-oxo-1-(pyridine-2-sulfonyl)-azepan-4-ylcarbamoyl]-3-methyl-butyl)}-amide:

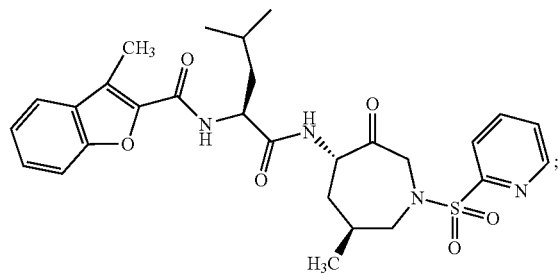

3-methyl-benzofuran-2-carboxylic acid {(S)-1-[(4R,6R)-6-methyl-3-oxo-1-(pyridine-2-sulfonyl)-azepan-4-ylcarbamoyl]-3-methyl-butyl}-amide:

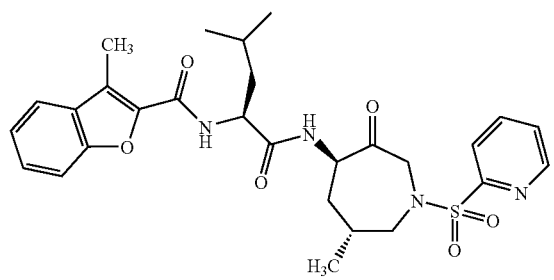

thieno[3,2-b]thiophene-2-carboxylic acid {(5)-1-[(4S,68)-6-methyl-3-oxo-1-(pyridine-2-sulfonyl)-azepan-4-ylcarbamoyl]-3-methyl-butyl}-amide:

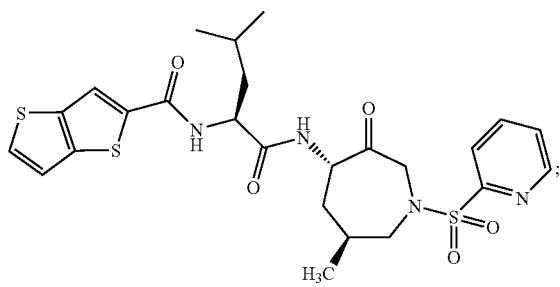

thieno[3,2-b]thiophene-2-carboxylic acid {(S)-1-[(4R,6R)-6-methyl-3-oxo-1-(pyridine-2-sulfonyl)-azepan-4-ylcarbamoyl]-3-methyl-butyl}-amide:

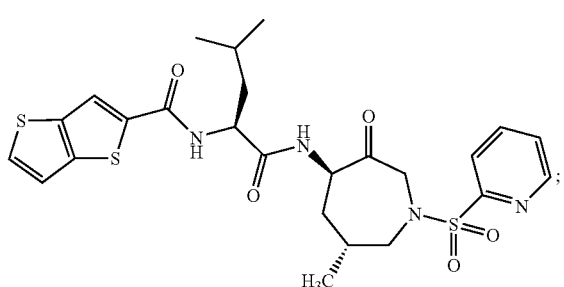

benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide:

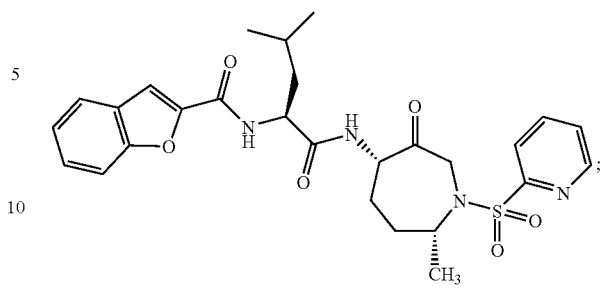

benzofuran-2-carboxylic acid {(S)-3-methyl-1-[(4R,7S)-7-methyl-3-oxo-1-(pyridine-2-sulfonyl)-azepan-4-ylcarbamoyl]-butyl}-amide:

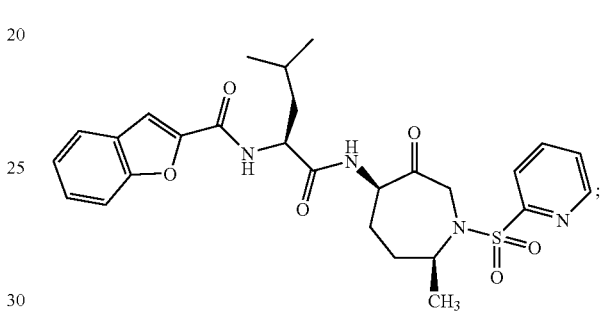

benzofuran-2-carboxylic acid {(S)-3-methyl-1-[(4S,7S)-7-methyl-3-oxo-1-(pyridine-2-sulfonyl)-azepan-4-ylcarbamoyl]-butyl}-amide:

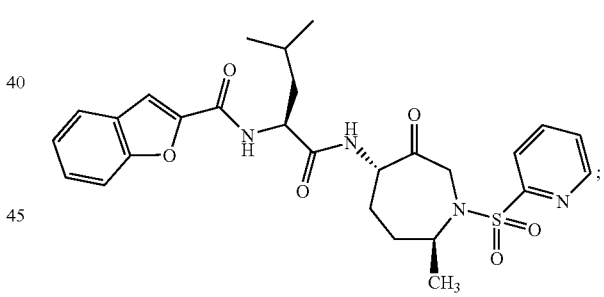

benzofuran-2-carboxylic acid {(S)-3-methyl-1-[(4R,7R)-7-methyl-3-oxo-1-(pyridine-2-sulfonyl)-azepan-4-ylcarbamoyl]-butyl}-amide:

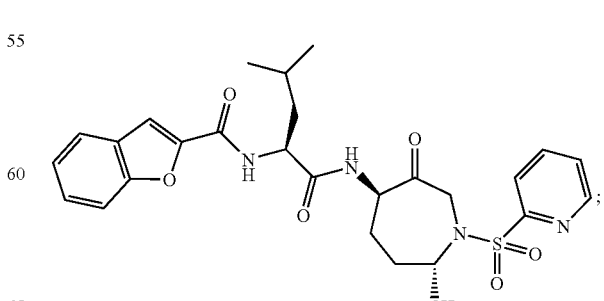

furo[3,2-b]pyridine-2-carboxylic acid {(S)-3-methyl-1-[(4S,7R)-7-methyl-3-oxo 1-(pyridine-2-sulfonyl)-azepan-4-yl-carbamoyl]-butyl}-amide:

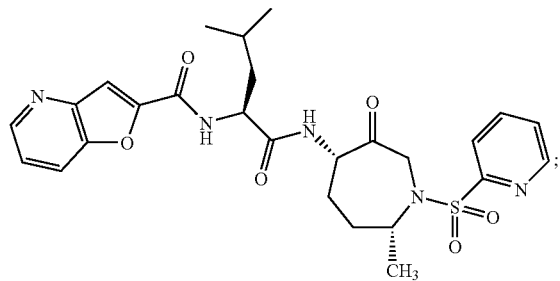

2,2,4-trideutero-furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide:

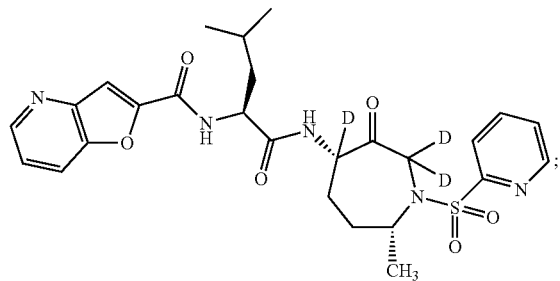

3-methyl-furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide:

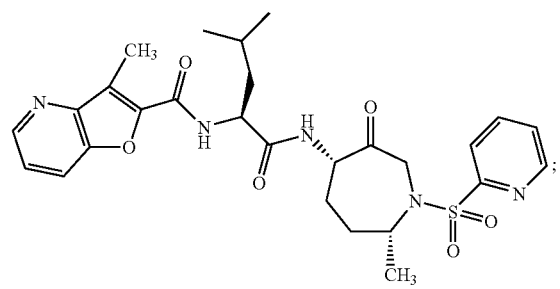

2,2,4-trideutero-3-methyl-1-furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide:

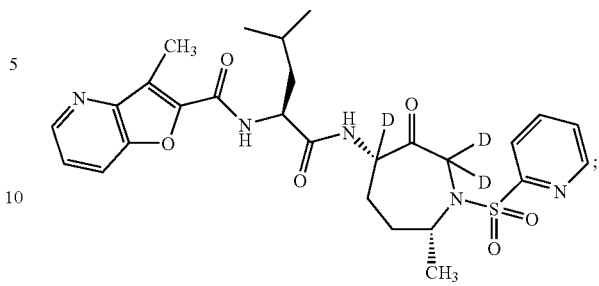

quinoline-6-carboxylic acid {(S)-3-methyl-1-[(4S,7R)-7-methyl-3-oxo-1-(pyridine-2-sulfonyl)-azepan-4-ylcarbamoyl]-butyl}-amide

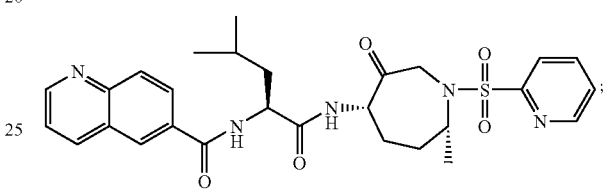

quinoline-3-carboxylic acid {(S)-3-methyl-1-[(4S,7R)-7-methyl-3-oxo-1-(pyridine-2-sulfonyl)-azepan-4-ylcarbamoyl]-butyl}-amide

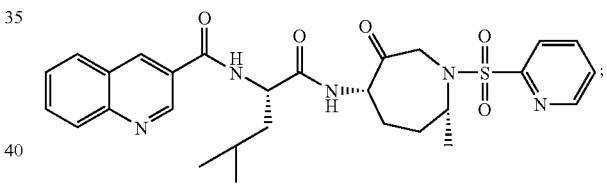

5-methoxy-benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide

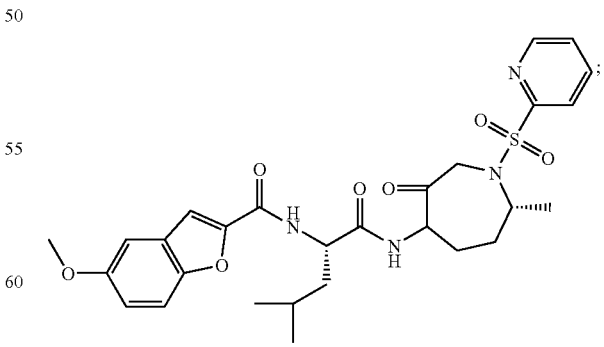

3-methyl-benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide

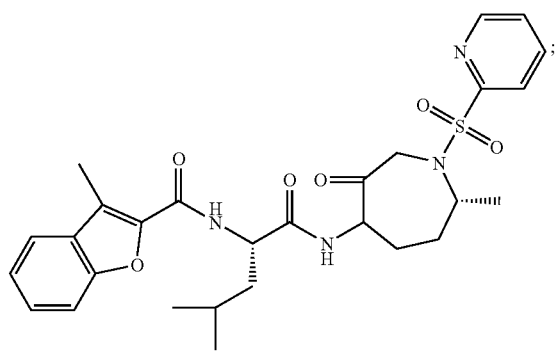

thieno[3,2-b]thiophene-2-carboxylic acid {(S)-3-methyl-1-[(4S,7R)-7-methyl-3-oxo-1-(pyridine-2-sulfonyl)-azepan-4-ylcarbamoyl]-butyl}-amide

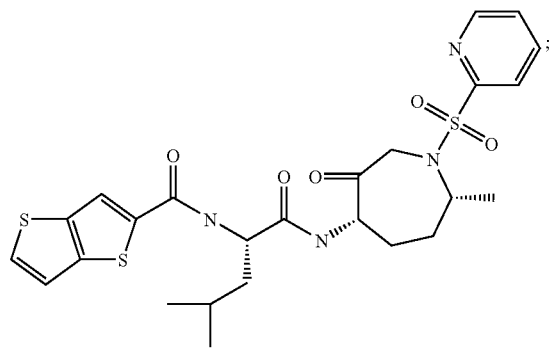

quinoxaline-2-carboxylic acid {(S)-3-methyl-1-[(4S,7R)-7-methyl-3-oxo-1-(pyridine-2-sulfonyl)-azepan-4-ylcarbamoyl]-butyl}-amide

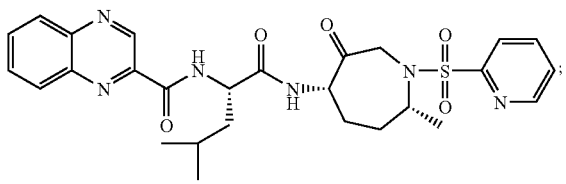

thieno[3,2-b]thiophene-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

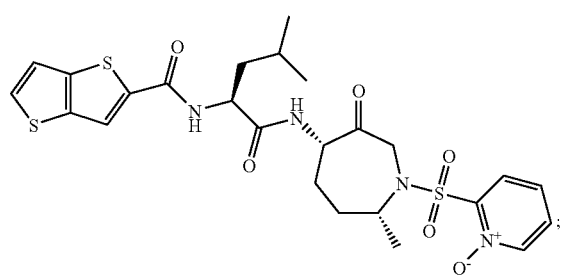

3-methyl-benzofuran-2-carboxylicacid {(S)-3-methyl-1-[(4S,7R)-7-methyl-3-oxo-1-(1-oxy-pyridine-2-sulfonyl)-azepan-4-ylcarbamoyl]-butyl}-amide

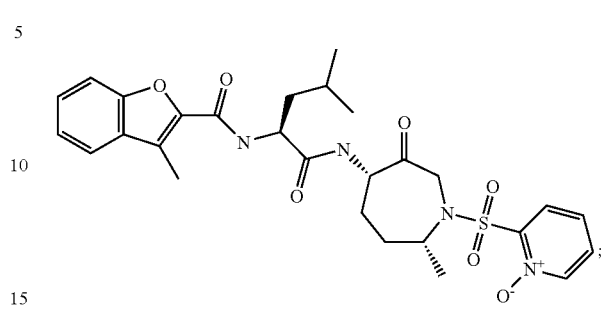

benzofuran-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

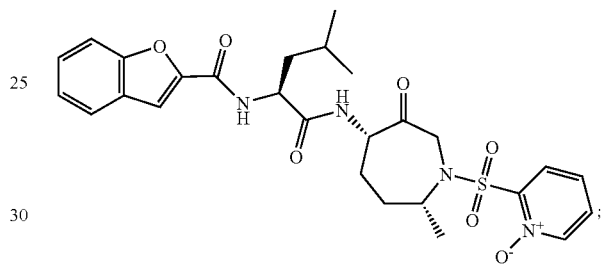

quinoline-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

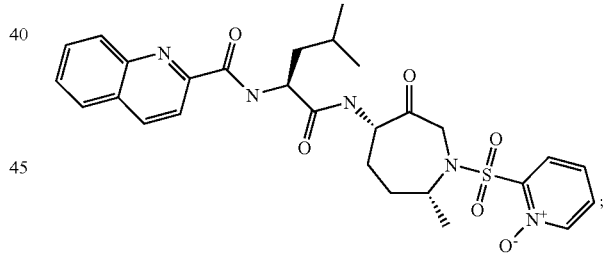

5,6-difluoro-benzofuran-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

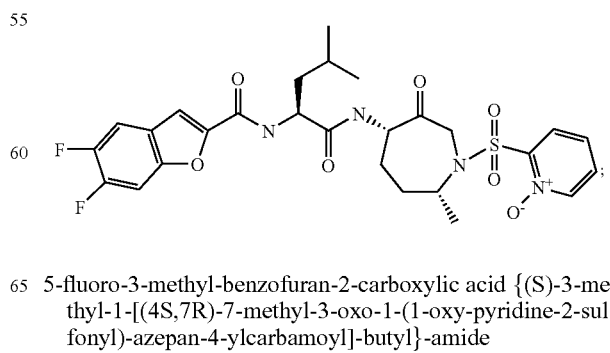

5-fluoro-3-methyl-benzofuran-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

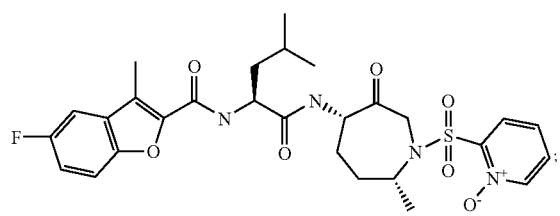

5-fluoro-benzofuran-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

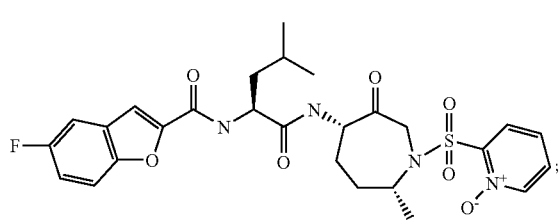

3-methyl-furo[3,2-b]]pyridine-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

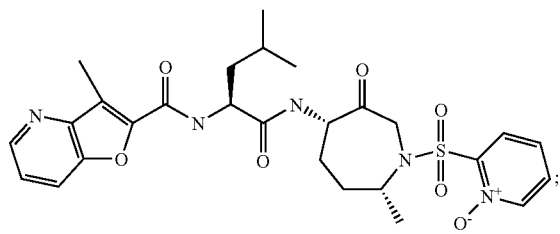

cyclohexanecarboxylic acid {(S)-3-methyl-1-[(4S,7R)-7-methyl-3-oxo-1-(1-oxy-pyridine-2-sulfonyl)-azepan-4-ylcarbamoyl]-butyl}-amide

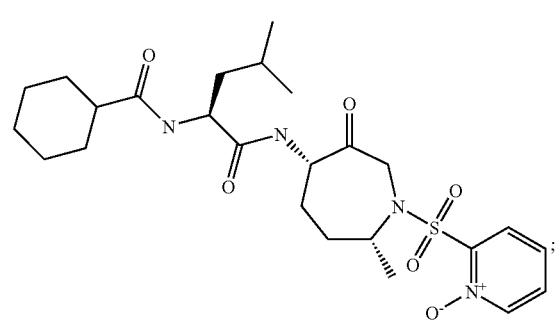

(S)-2-(2-cyclohexyl-ethanoylamino)-4-methyl-pentanoic acid [(4S,7R)-7-methyl-3-oxo-1-(1-oxy-pyridine-2-sulfonyl)-azepan-4-yl]-amide

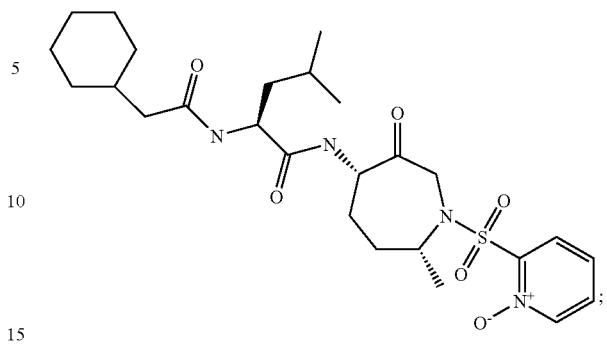

(S)-2-(3-cyclohexyl-propanoylamino)-4-methyl-pentanoic acid [(4S,7R)-7-methyl-3-oxo-1-(1-oxy-pyridine-2-sulfonyl)-azepan-4-yl]-amide

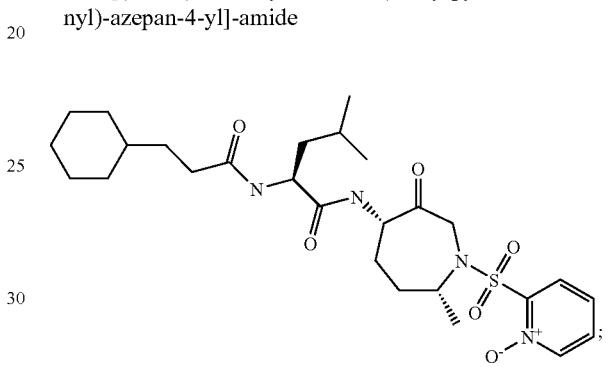

(S)-2-(4-cyclohexyl-butanoylamino)-4-methyl-pentanoic acid [(4S,7R)-7-methyl-3-oxo-1-(1-oxy-pyridine-2-sulfonyl)-azepan-4-yl]-amide

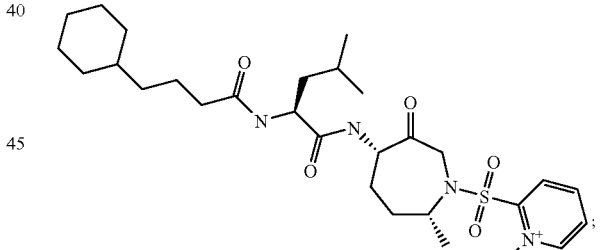

(S)-2-(5-cyclohexyl-pentanoylamino)-4-methyl-pentanoic acid [(4S,7R)-7-methyl-3-oxo-1-(1-oxy-pyridine-2-sulfonyl)-azepan-4-yl]-amide

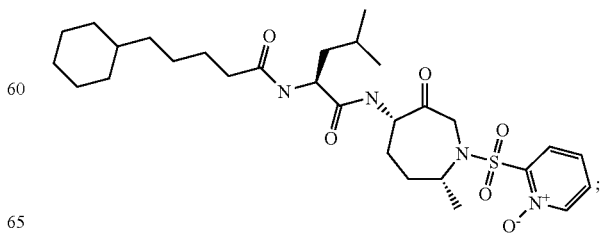

benzofuran-2-carboxylic acid {(S)-3-methyl-1-[(4S,7R)-7-methyl-3-oxo-1-(5-trifluoromethyl-pyridine-2-sulfonyl)-azepan-4-ylcarbamoyl]-butyl}-amide

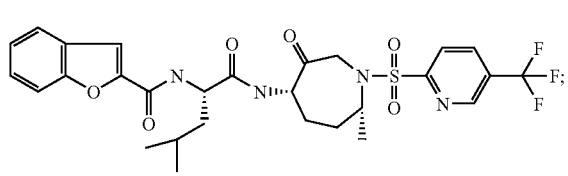

5-fluoro-benzofuran-2-carboxylic acid {(S)-3-methyl-1-[(4S,7R)-7-methyl-3-oxo-1-(5-trifluoromethyl-pyridine-2-sulfonyl)-azepan-4-ylcarbamoyl]-butyl}-amide

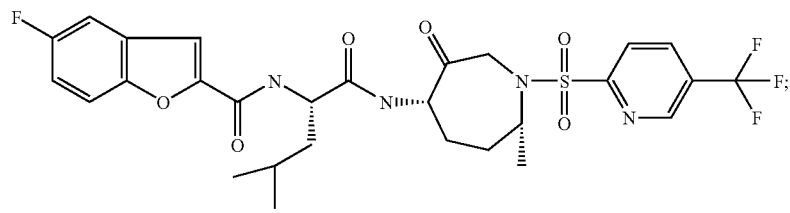

thieno[3,2-b]thiophene-2-carboxylic acid {(S)-3-methyl-1-[(4S,7R)-7-methyl-3-oxo-1-(5-trifluoromethyl-pyridine-2-sulfonyl)-azepan-4-ylcarbamoyl]-butyl}-amide

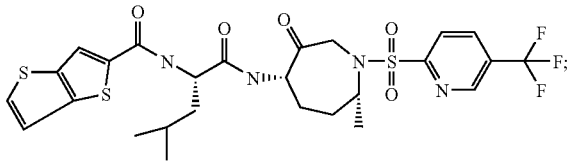

benzofuran-2-carboxylic acid {1-[(4S,7R)-7-methyl-3-oxo-1-(pyridine-2-sulfonyl)-azepan-4-ylcarbamoyl]-cyclohexyl}-amide

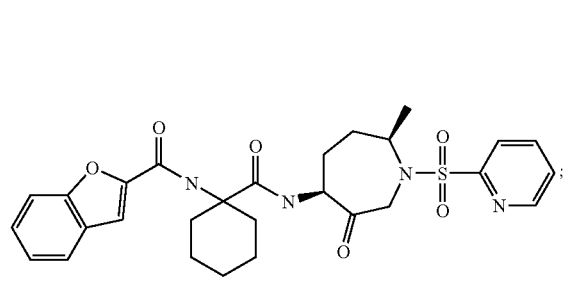

thiophene-3-carboxylic acid {(S)-3,3-dimethyl-1-[(4S,7R)-7-methyl-3-oxo-1-(pyridine-2-sulfonyl)-azepan-4-ylcarbamoyl]-butyl}-amide

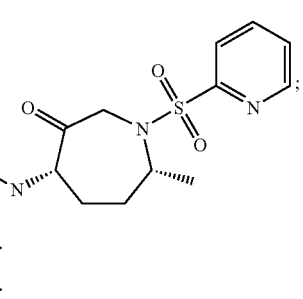

furan-2-carboxylic acid {(S)-3,3-dimethyl-1-[(4S,7R)-7-methyl-3-oxo-1-(pyridine-2-sulfonyl)-azepan-4-ylcarbamoyl]-butyl}-amide

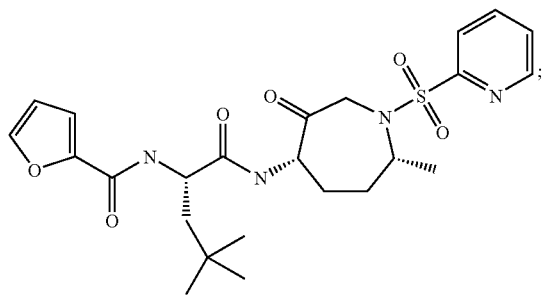

thieno[3,2-b]thiophene-2-carboxylic acid {(S)-3,3-dimethyl-1-[(4S,7R)-7-methyl-3-oxo-1-(pyridine-2-sulfonyl)-azepan-4-ylcarbamoyl]-butyl}-amide

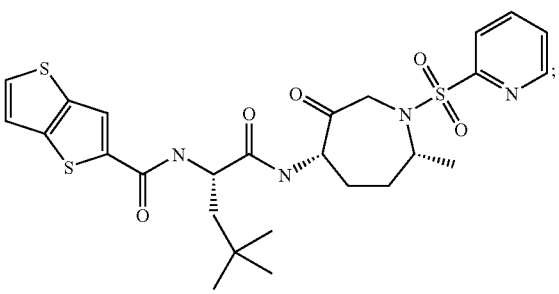

benzofuran-2-carboxylic acid {(S)-2-cyclohexyl-1-[(4S,7R)-7-methyl-3-oxo-1-(pyridine-2-sulfonyl)-azepan-4-ylcarbamoyl]-ethyl}-amide

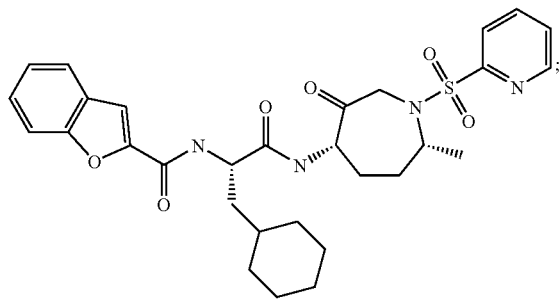

furan-2-carboxylic acid {(S)-2-cyclohexyl-1-[(4S,7R)-7-methyl-3-oxo-1-(pyridine-2-sulfonyl)-azepan-4-ylcarbamoyl]-ethyl}-amide

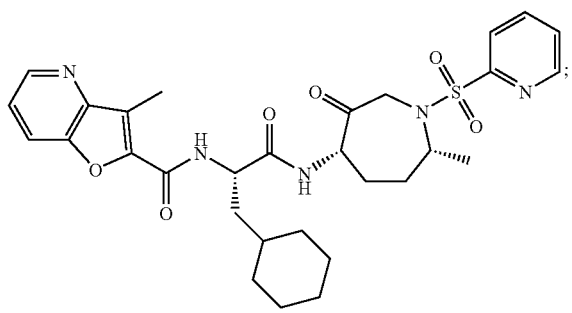

(2R,4aR,8aR)-octahydro-benzo[1,4]dioxine-2-carboxylic acid [(S)-1-((4S,7R)-1-methanesulfonyl-7-methyl-3-oxo-azepan-4-ylcarbamoyl)-3-methyl-butyl]-amide

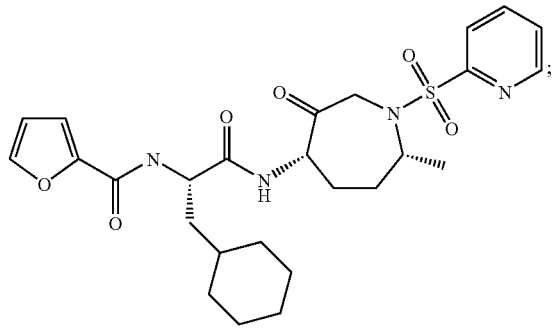

thiophene-3-carboxylic acid {(S)-2-cyclohexyl-1-[(4S,7R)-7-methyl-3-oxo-1-(pyridine-2-sulfonyl)-azepan-4-ylcarbamoyl]-ethyl}-amide

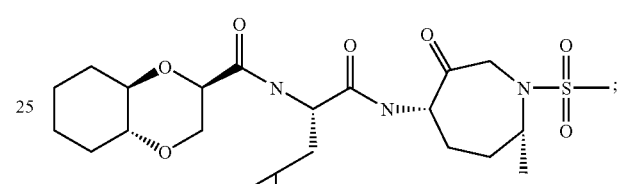

furan-2-carboxylic acid [(S)-2-cyclohexyl-1-((4S,7R)-7-methyl-3-oxo-1-propyl-azepan-4-ylcarbamoyl)-ethyl]-amide

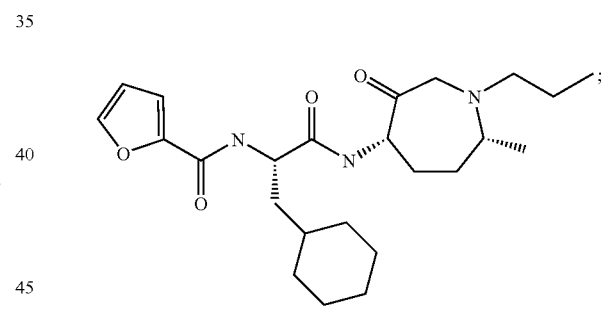

thiophene-3-carboxylic acid [(S)-2-cyclohexyl-1-((4S,7R)-7-methyl-3-oxo-1-propyl-azepan-4-ylcarbamoyl)-ethyl]-amide

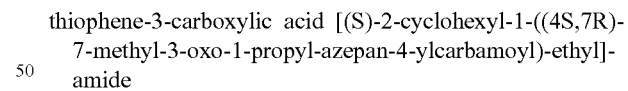

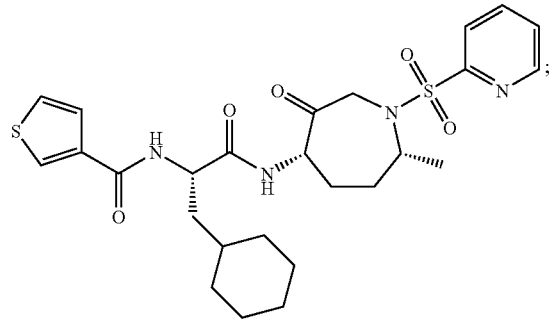

3-methyl-furo[3,2-b]-pyridine-2-carboxylic acid {(S)-2-cyclohexyl-1-[(4S,7R)-7-methyl-3-oxo-1-(pyridine-2-sulfonyl)-azepan-4-ylcarbamoyl]-ethyl}-amide benzofuran-2-carboxylic acid [(S)-2-cyclohexyl-1-((4S,7R)-7-methyl-3-oxo-1-propyl-azepan-4-ylcarbamoyl)-ethyl]-amide

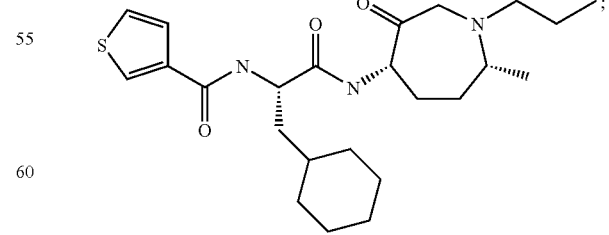

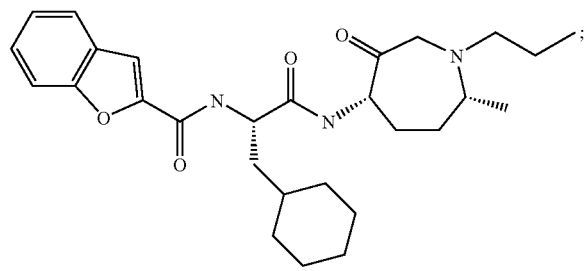

1-(3-cyclohexyl-propanoylamino)-cyclohexanecarboxylic acid((4S,7R)-1-cyclohexylmethyl-7-methyl-3-oxo-azepan-4-yl)-amide

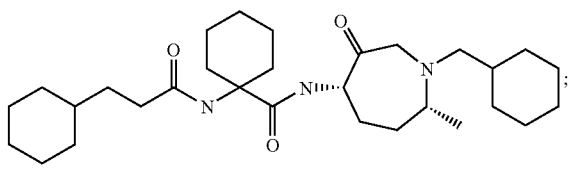

benzofuran-2-carboxylic acid [1-((4S,7R)-1-cyclohexylmethyl-7-methyl-3-oxo-azepan-4-ylcarbamoyl)-cyclohexyl]-amide

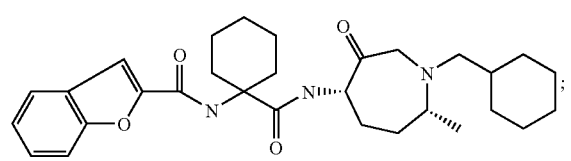

benzofuran-2-carboxylic acid [(S)-3-methyl-1-((4S,7R)-7-methyl-3-oxo-1-propyl-azepan-4-ylcarbamoyl)-butyl]-amide

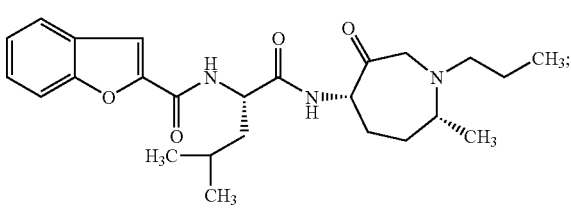

(2R,5S)-5-((S)-2-tert-butoxycarbonylamino-4-methyl-pentanoylamino)-2-methyl-6-oxo-azepane-1-carboxylic acid benzyl ester

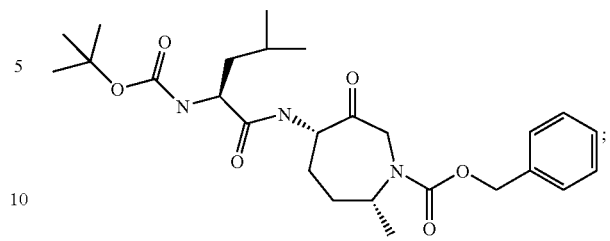

benzofuran-2-carboxylic acid {(S)-3-methyl-1-[(4S,7R)-7-methyl-1-(1-morpholin-4-yl-methanoyl)-3-oxo-azepan-4-ylcarbamoyl]-butyl}-amide

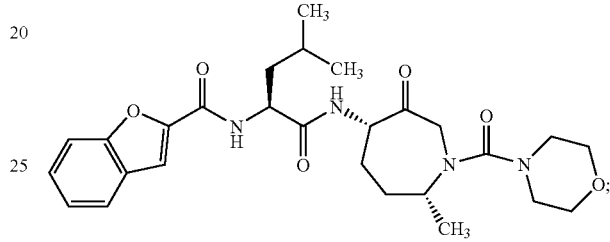

(S)-2-(3-cyclohexyl-propanoylamino)-4-methyl-pentanoic acid [(4S,7R)-7-methyl-1-(1-morpholin-4-yl-methanoyl)-3-oxo-azepan-4-yl]-amide

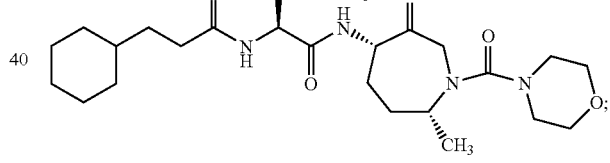

(2R,5S)-5-{(S)-2-[(1-benzofuran-2-yl-methanoyl)-amino]-4-methyl-pentanoylamino}-2-methyl-6-oxo-azepane-1-carboxylic acid (tetrahydro-pyran-4-yl)-amide

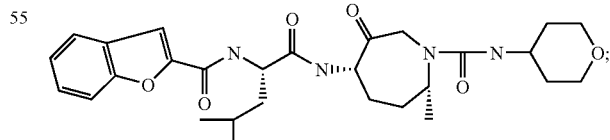

(S)-2-{[1-((2R,5S)-5-{(S)-2-[(1-benzofuran-2-yl-methanoyl)-amino]-4-methyl-pentanoylamino}-2-methyl-6-oxo-azepan-1-yl)-methanoyl]-amino}-4-methyl-pentanoic acid methyl ester

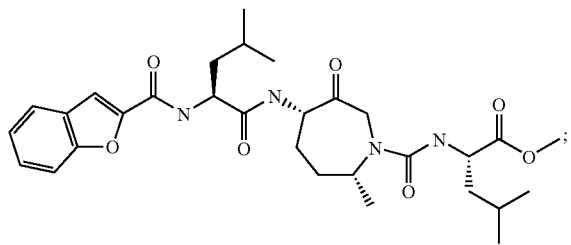

(S)-2-{[1-((2R,5S)-5-{(S)-2-[(1-benzofuran-2-yl-methanoyl)-amino]-4-methyl-pentanoylamino}-2-methyl-6-oxo-azepan-1-yl)-methanoyl]-amino}-4-methyl-pentanoic acid

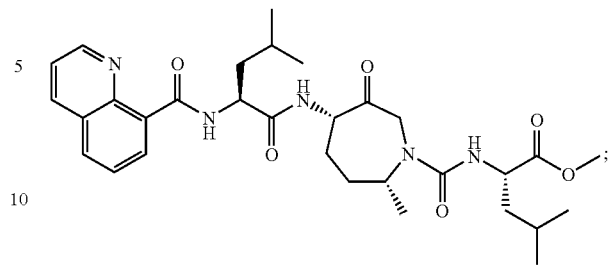

(S)-4-methyl-2-{[1-((2R,5S)-2-methyl-5-{(S)-4-methyl-2-[(1-quinolin-8-yl-methanoyl)-amino]-pentanoylamino}-6-oxo-azepan-1-yl)-methanoyl]-amino}-pentanoic acid

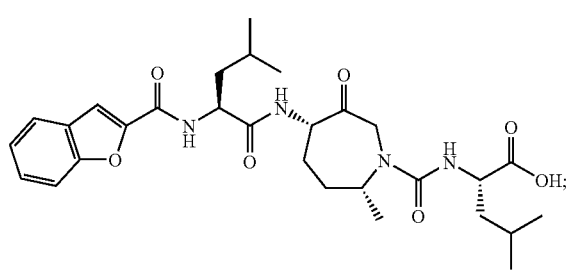

(S)-2-{[1-(4-{(S)-2-[(1-benzofuran-2-yl-methanoyl)-amino]-4-methyl-pentanoylamino 1-3-oxo-azepan-1-yl)-methanoyl]-amino)-4-methyl-pentanoicacid methyl ester

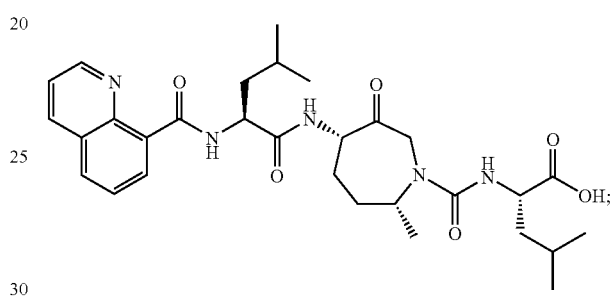

(R)-2-{[1-(4-{(S)-2-[(1-benzofuran-2-yl-methanoyl)-amino]-4-methyl-pentanoylamino}-3-oxo-azepan-1-yl)-methanoyl]-amino}-4-methyl-pentanoic acid methyl ester

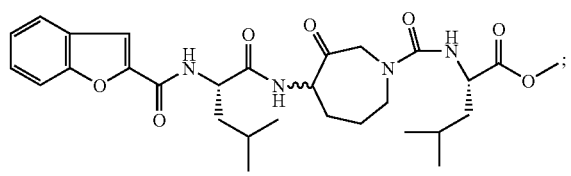

(S)-2-{[1-(4-{(S)-2-[(1-benzofuran-2-yl-methanoyl)-amino]-4-methyl-pentanoylamino}-3-oxo-azepan-1-yl)-methanoyl]-amino}-4-methyl-pentanoic acid

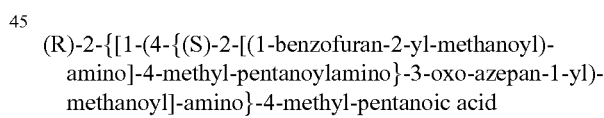

(R)-2-{[1-(4-{(S)-2-[(1-benzofuran-2-yl-methanoyl)-amino]-4-methyl-pentanoylamino}-3-oxo-azepan-1-yl)-methanoyl]-amino}-4-methyl-pentanoic acid

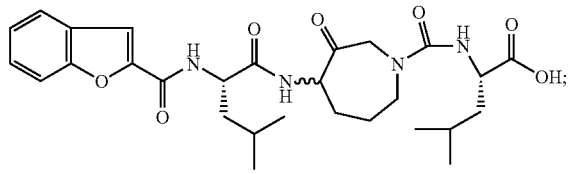

(S)-4-methyl-2-{[1-((2R,5S)-2-methyl-5-{(S)-4-methyl-2-[(1-quinolin-8-yl-methanoyl)-amino]-pentanoylamino)-6-oxo-azepan-1-yl)-methanoyl]-amino}-pentanoic acid methyl ester

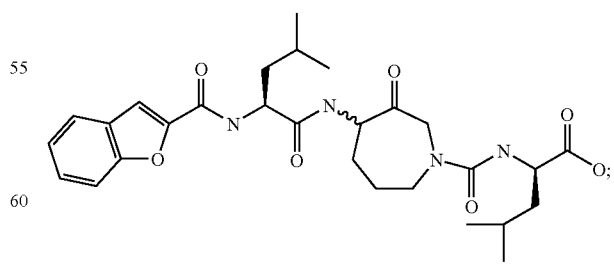

4,5 (R,S)-benzofuran-2-carboxylic acid {(S)-3-methyl-1-[5-methyl-3-oxo-1-(pyridine-2-sulfonyl)-azepan-4-ylcarbamoyl]-butyl}amide:

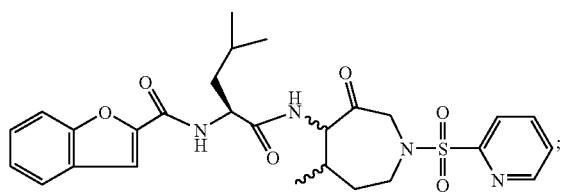

4S,5S-benzofuran-2-carboxylic acid {(S)-3-methyl-1-[5-methyl-3-oxo-1-(pyridine-2-sulfonyl)-azepan-4-ylcarbamoyl]-butyl}amide:

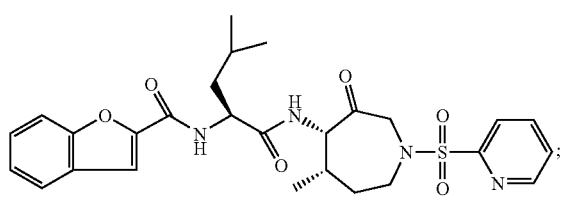

4S,5R-benzofuran-2-carboxylic acid {(S)-3-methyl-1-[5-methyl-3-oxo-1-(pyridine-2-sulfonyl)-azepan-4-ylcarbamoyl]-butyl}amide

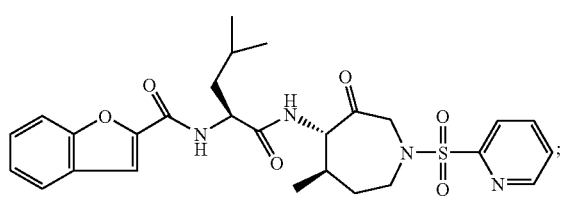

4R,5R-benzofuran-2-carboxylic acid {(S)-3-methyl-1-[5-methyl-3-oxo-1-(pyridine-2-sulfonyl)-azepan-4-ylcarbamoyl]-butyl}amide

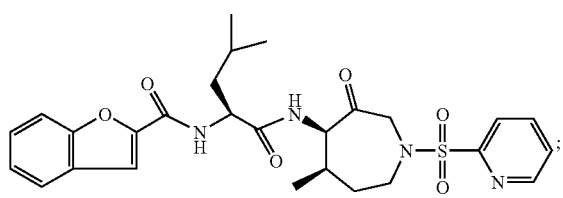

4R,5S-benzofuran-2-carboxylic acid {(S)-3-methyl-1-[5-methyl-3-oxo-1-(pyridine-2-sulfonyl)-azepan-4-ylcarbamoyl]-butyl}aide:

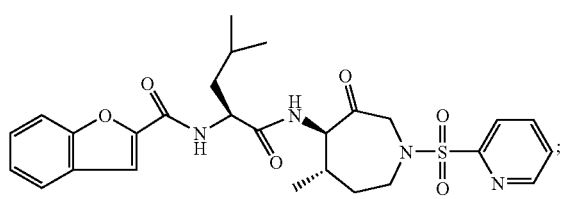

(R)-2-biphenyl-3-yl-4-methyl-pentanoic acid [(4S,7R)-7-methyl-3-oxo-1-(pyridine-2-sulfonyl)-azepan-4-yl]-amide:

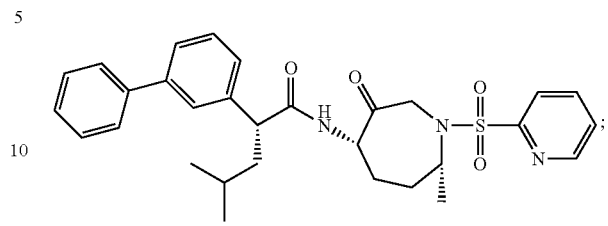

3-Methyl-furo[3,2-b]-pyridine-2-carboxylic acid {1-[(4S,7R)-7-methyl-3-oxo-1-(pyridine-2-sulfonyl)-azepan-4-ylcarbamoyl]-cyclohexyl}-amide:

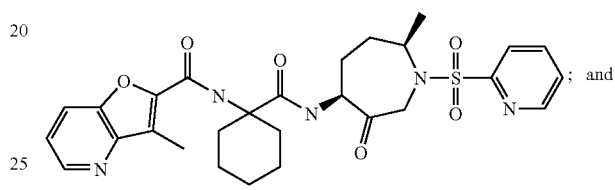

1-(3-cyclohexyl-propanoylamino)-cyclohexanecarboxylic acid [(4S,7R)-7-methyl-3-oxo-1-(pyridine-2-sulfonyl)-azepan-4-yl]-amide:

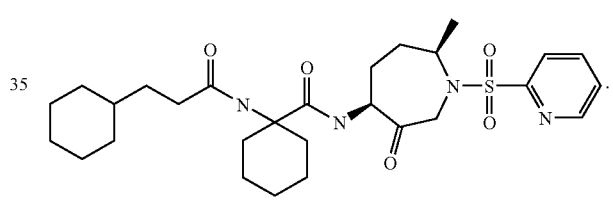

A most particularly preferred embodiment of the present invention is benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide:

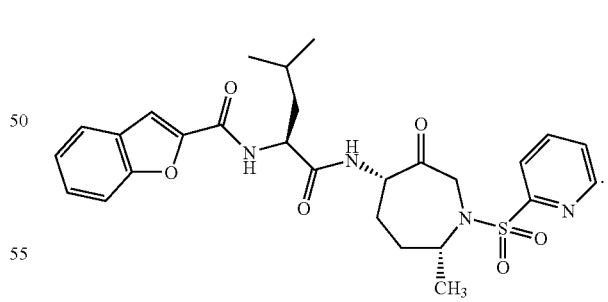

Specific representative compounds of the present invention are set forth in Examples 1-64.

Compared to the corresponding 5- and 6-membered ring compounds, the 7-membered ring compounds of the present invention are configurationally more stable at the carbon center alpha to the ketone.

The present invention includes deuterated analogs of the inventive compounds. Representative examples of such a deuterated compounds are set forth in Examples 7, 9 and 11.

A representative synthetic route for the deuterated compounds of the present invention is set forth in Scheme 4, below. The deuterated compounds of the present invention exhibit superior chiral stability compared to the protonated isomer.

Definitions

The present invention includes all hydrates, solvates, complexes and prodrugs of the compounds of this invention. Prodrugs are any covalently bonded compounds which release the active parent drug according to Formula I in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or any subformula thereof is independent of its meaning, or any other substituent's meaning, at any other occurrence, unless specified otherwise.

Abbreviations and symbols commonly used in the peptide and chemical arts are used herein to describe the compounds of the present invention. In general, the amino acid abbreviations follow the IUPAC-IUB Joint Commission on Biochemical Nomenclature as described in *Eur. J. Biochem.*, 158, 9 (1984).

"Proteases" are enzymes that catalyze the cleavage of amide bonds of peptides and proteins by nucleophilic substitution at the amide bond, ultimately resulting in hydrolysis. Such proteases include: cysteine proteases, serine proteases, aspartic proteases, and metalloproteases. The compounds of the present invention are capable of binding more strongly to the enzyme than the substrate and in general are not subject to cleavage after enzyme catalyzed attack by the nucleophile. They therefore competitively prevent proteases from recognizing and hydrolyzing natural substrates and thereby act as inhibitors.

The term "amino acid" as used herein refers to the D- or L-isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"Hydrogen" or "H" includes all of its possible isotopes, including "deuterium" or "D" or "$^2$H"; and "tritium" or "T" or "$^3$H".

"$C_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof. $C_{1-6}$alkyl may be optionally substituted by a moiety selected from the group consisting of: $OR^{14}$, $C(O)R^{14}$, $SR^{14}$, $S(O)R^{14}$, $NR142$, $R^{14}NC(O)OR^5$, $CO_2R^{14}$, $CO_2NR^{14}_2$, $N(C=NH)NH_2$, Het, $C_{3-6}$cycloalkyl, and Ar; where $R^5$ is selected from the group consisting of: H, $C_{1-6}$alkyl, $C_{2-6}$alkenyl, $C_{2-6}$alkynyl, $C_{3-6}$cycloalkyl-$C_{0-6}$alkyl, Ar—$C_{0-6}$alkyl and Het-$C_{0-6}$alkyl; and $R^{14}$ is selected from the group consisting of: H, $C_{1-6}$alkyl, Ar—$C_{0-6}$alkyl, and Het-$C_{0-6}$alkyl;

"$C_{3-6}$cycloalkyl" as applied herein is meant to include substituted and unsubstituted cyclopropane, cyclobutane, cyclopentane and cyclohexane.

"$C_{2-6}$ alkenyl" as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

"$C_{2-6}$alkanonyl" as applied herein is meant to include unsubstituted and substituted acetyl, propanonyl, butanonyl, pentanonyl, and hexanonyl.

"$C_{2-6}$alkynyl" means an alkyl group of 2 to 6 carbons wherein one carbon-carbon single bond is replaced by a carbon-carbon triple bond. $C_{2-6}$ alkynyl includes acetylene, 1-propyne, 2-propyne, 1-butyne, 2-butyne, 3-butyne and the simple isomers of pentyne and hexyne.

"Halogen" means F, Cl, Br, and I.

"Ar" or "aryl" means phenyl or naphthyl, optionally substituted by one or more of Ph-$C_{0-6}$alkyl; Het-$C_{0-6}$alkyl; $C_{1-6}$alkoxy; Ph-$C_{0-6}$alkoxy; Het-$C_{0-6}$alkoxy; OH, $(CH_2)_{1-6}NR^{15}R^{16}$; $O(CH_2)_{1-6}NR^{15}R^{16}$; $C_{1-6}$alkyl, $OR^{17}$, $N(R^{17})_2$, $SR^{17}$, $CF_3$, $NO_2$, $CN$, $CO_2R^{17}$, $CON(R^{17})$, F, Cl, Br or I; where $R^{15}$ and $R^{16}$ are H, $C_{1-6}$alkyl, Ph-$C_{0-6}$alkyl, naphthyl-$C_{0-6}$alkyl or Het-$C_{0-6}$alkyl; and $R^{17}$ is phenyl, naphthyl, or $C_{1-6}$alkyl.

"Ar—Ar" means aryl covalently linked to a second aryl. Examples of "Ar—Ar" include biphenyl or naphythyl-phenyl or phenyl-naphthyl.

As used herein "Het" or "heterocyclic" represents a stable 5- to 7-membered monocyclic, a stable 7- to 10-membered bicyclic, or a stable 11- to 18-membered tricyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure, and may optionally be substituted with one or two moieties selected from $C_{0-6}$Ar, $C_{1-6}$alkyl, $OR^{17}$, $N(R^{17})_2$, $SR^{17}$, $CF_3$, $NO_2$, $CN$, $CO_2R^{17}$, $CON(R^{17})$, F, Cl, Br and I, where $R^{17}$ is phenyl, naphthyl, or $C_{1-6}$alkyl. Examples of such heterocycles include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, pyridinyl, 1-oxo-pyridinyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, quinoxalinyl, isoquinolinyl, benzimidazolyl, benzopyranyl, benzoxazolyl, furanyl, benzofuranyl, thiophenyl, benzo[b]thiophenyl, thieno[3,2-b]thiophenyl, benzo[1,3]dioxolyl, 1,8 naphthyridinyl, pyranyl, tetrahydrofuranyl, tetrahydropyranyl, thienyl, benzoxazolyl, thiamorpholinyl sulfoxide, thiamorpholinyl sulfone, and oxadiazolyl, as well as triazolyl, thiadiazolyl, oxadiazolyl, isothiazolyl, imidazolyl, pyridazinyl, pyrimidinyl, triazinyl and tetrazinyl which are available by routine chemical synthesis and are stable. The term heteroatom as applied herein refers to oxygen, nitrogen and sulfur.

"Ar—Het" means an aryl group covalently linked to a heterocycle. Examples of "Ar—Het" include phenyl-piperidine, phenyl-piperazine, phenyl-2-oxopiperazine, naphthyl-piperidine, naphthyl-piperazine, and naphthyl-2-oxopiperazine.

"Het-Ar" means a heterocycle covalently linked to a aryl group. Examples of such "Het-Ar" include piperidinyl-phenyl, piperazinyl-phenyl, 2-oxopiperazinyl-phenyl, piperidinyl-naphthyl, piperazinyl-naphthyl, and 2-oxopiperazinyl-naphthyl.

"Het-Het" means a heterocycle covalently linked to a second heterocycle. Examples of such "Het-Het" include bipyridine, pyridinyl-piperidine, pyridinyl-piperazine, pyridinyl-2-oxopiperazine, thiophenyl-piperidine, thiophenyl-piperazine, and thiophenyl-2-oxopiperazine.

Here and throughout this application the term $C_0$ denotes the absence of the substituent group immediately following; for instance, in the moiety $ArC_{0-6}$alkyl, when C is 0, the substituent is Ar, e.g., phenyl. Conversely, when the moiety $ArC_{0-6}$alkyl is identified as a specific aromatic group, e.g., phenyl, it is understood that the value of C is 0.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical.

Certain reagents are abbreviated herein. m-CPBA refers to 3-chloroperoxybenzoic acid, EDC refers to N-ethyl-N'(dimethylaminopropyl)-carbodiimide, DMF refers to dimethyl formamide, DMSO refers to dimethyl sulfoxide, TEA refers to triethylamine, TFA refers to trifluoroacetic acid, and THF refers to tetrahydrofuran.

Methods of Preparation

Compounds of the general formula I may be prepared in a fashion analogous to that outlined in Schemes 1 to 8.

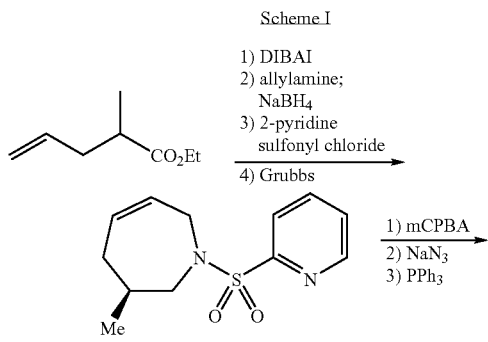

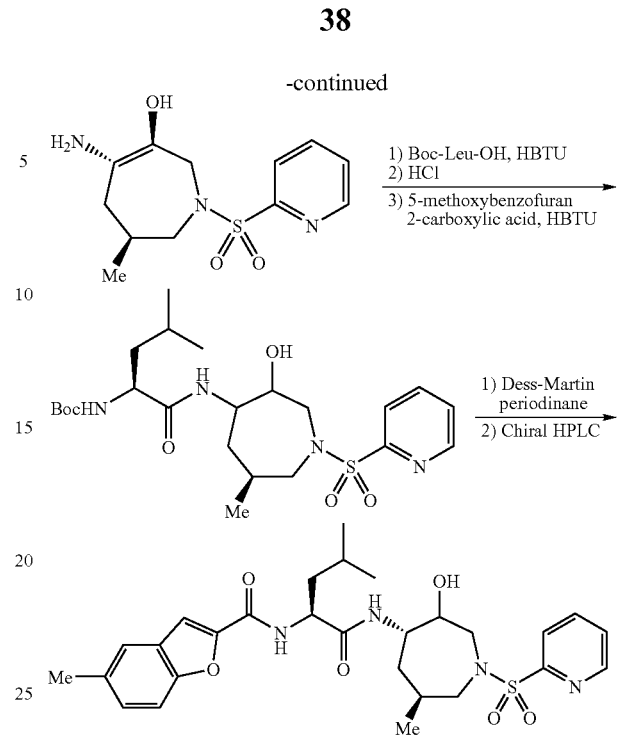

2-Methyl-pent-4-enoic acid ethyl ester is converted to a N-2-pyridinesulfonyl-azapine by reduction to the aldehyde, reductive amination with allylamine, sulfonylation with 2-pyridyl sulfonyl chloride, and olefin metathesis with Grubbs' catalyst. Epoxidation with mCPBA affords a mixture of epoxides that are separable by column chromatography. The syn epoxide is converted into an amino alcohol by opening with sodium azide followed by reduction with triphenylphosphine. Acylation of the free amine with Boc-leucine and a coupling reagent such as HBTU or EDC, followed by deprotection of the Boc group with HCl, and acylation with a variety of aromatic carboxylic acids and coupling reagents such as HBTU or EDC gives the intermediate alcohols. Final oxidation with Dess-Martin periodinane and HPLC affords the desired ketones.

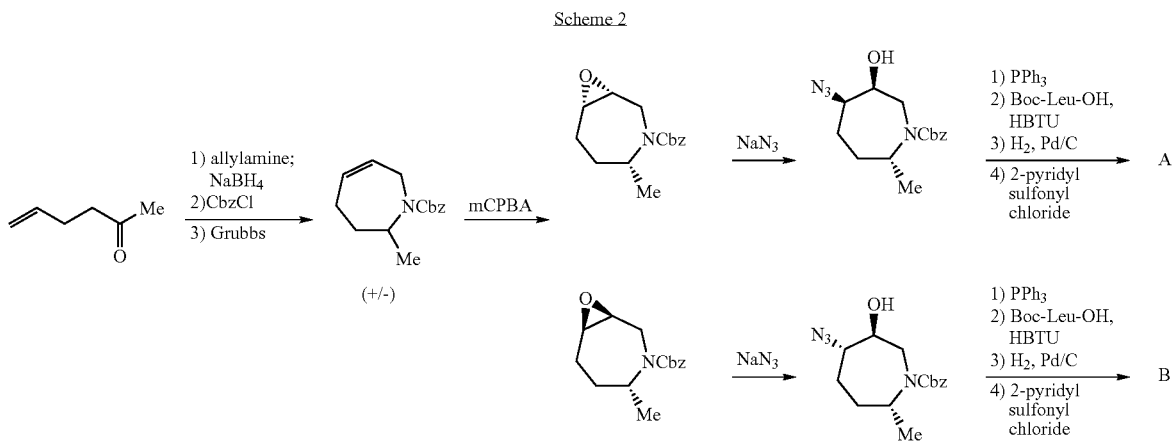

-continued

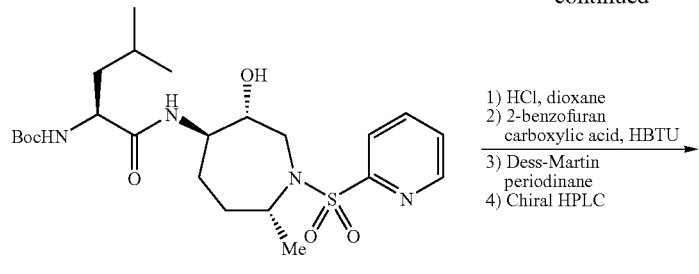

A

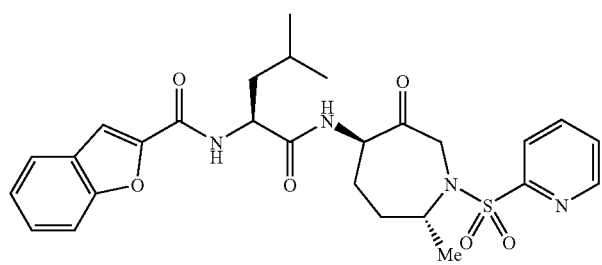

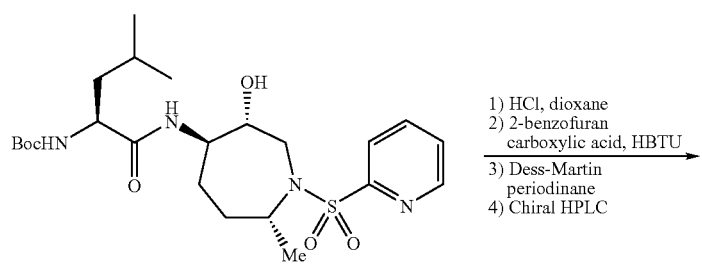

B

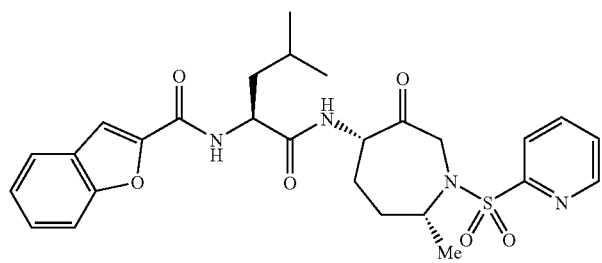

5-Hexen-2-one is converted to a N-carbobenzyloxy-azapine by reductive amination with allylamine, protection with carbobenzyloxychloride, and olefin metathesis with Grubbs' catalyst. Epoxidation with mCPBA affords a mixture of epoxides that are separable by column chromatography. Each epoxide is converted into an amino alcohol by opening with sodium azide followed by reduction with triphenylphosphine. Acylation of the free amine with Boc-leucine and a coupling reagent such as HBTU or EDC, followed by deprotection of the Cbz group by hydrogenolysis provides the secondary amines which are in turn sulfonylated with 2-pyridine sulfonylchloride. Deprotection of the Boc groups with HCl and acylation with a variety of aromatic carboxylic acids and coupling reagents such as HBTU or EDC gives the intermediate alcohols. Final oxidation with Dess-Martin periodinane and HPLC affords the desired ketones.

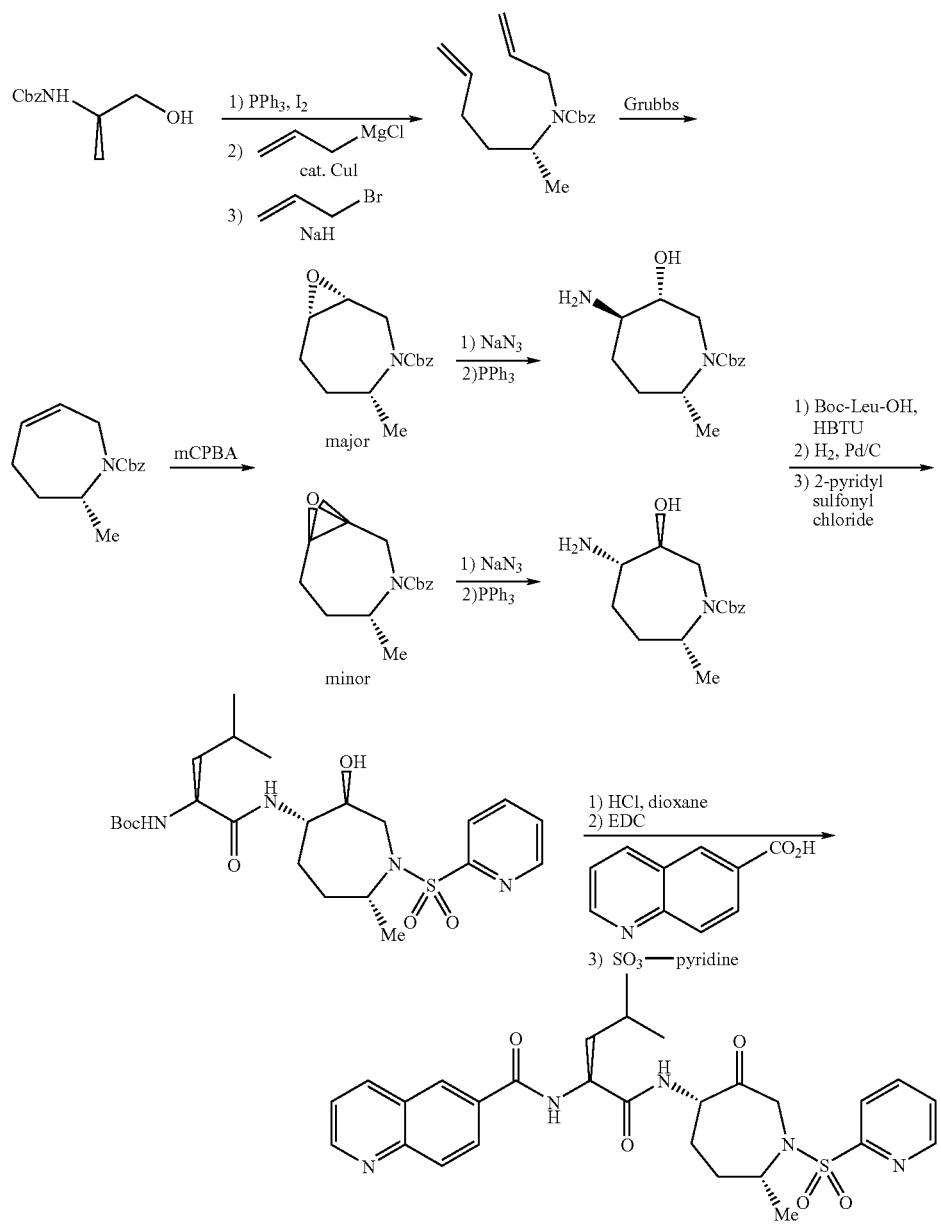

Carbobenyzloxy-D-alaninol (Cbz-D-alaninol) is first converted to an iodide, then is reacted with allyl Grignard with a copper (I) catalyst or a similar allyl organometallic reagent. The amine is then alkylated with allyl iodide. Grubbs' catalyst is then used to form the azapine ring by ring closing metathesis. Epoxidation of the alkene followed by separation of the diastereomers followed by opening of the epoxide of the minor component with sodium azide provides the intermediate azido alcohol. Reduction of the azide followed by acylation of the amine with a protected amino acid such as Boc-leucine, followed by deprotection of the Cbz gives the intermediate secondary amine, which is then sulfonylated with a sulfonyl chloride such as pyridine sulfonyl chloride. Deprotection of the Boc group followed by acylation with an acylating agent such as quinoline-6-carboxylic acid, HBTU, NMM, and final oxidation of the secondary alcohol to the ketone with an oxidant such as sulfur trioxide-pyridine or Dess-Martin periodinane provides the desired products.

Scheme 4

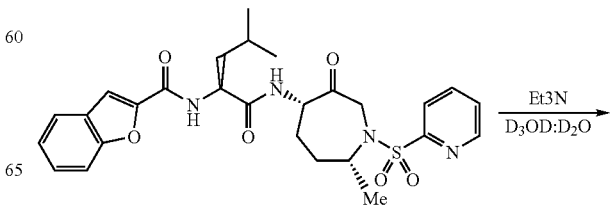

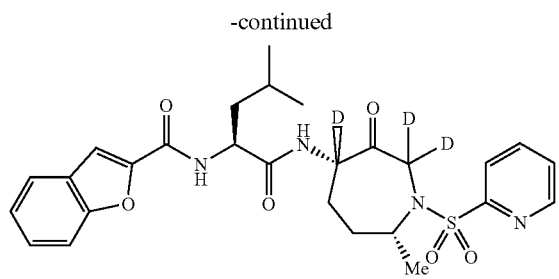

Deuterated inhibitors can be prepared from the parent inhibitors such as benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide by treating with a base such as triethyl amine and stirring for several days in a deteurated protic solvent such as CD$_3$OD: D$_2$O.

Scheme 5

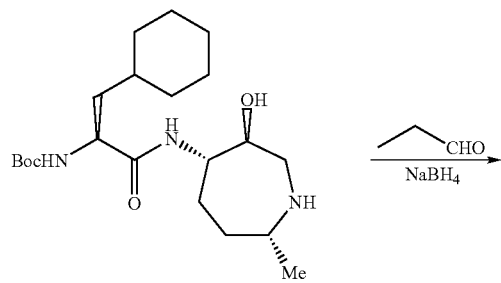

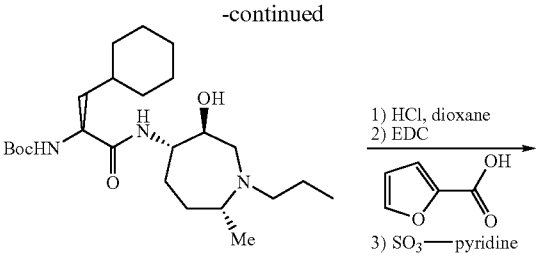

Intermediate (S)-3-Cyclohexyl-N-((3S,4S,7R)-3-hydroxy-7-methyl-azepan-4-yl)-2-methyl-propionamide, as described in Scheme 3 (using Boc-cyclohexylalanine instead of Boc-L-leucine), is reductively aminated with an aldehyde or a ketone such as propionaldehyde, then treated with a reducing agent such as sodium borohydride. Deprotection of the Boc group followed by acylation with an acylating agent such as 2-furan carboxylic acid, HBTU, NMM, and final oxidation of the secondary alcohol to the ketone with an oxidant such as sulfur trioxide-pyridine provides the desired products.

Scheme 6

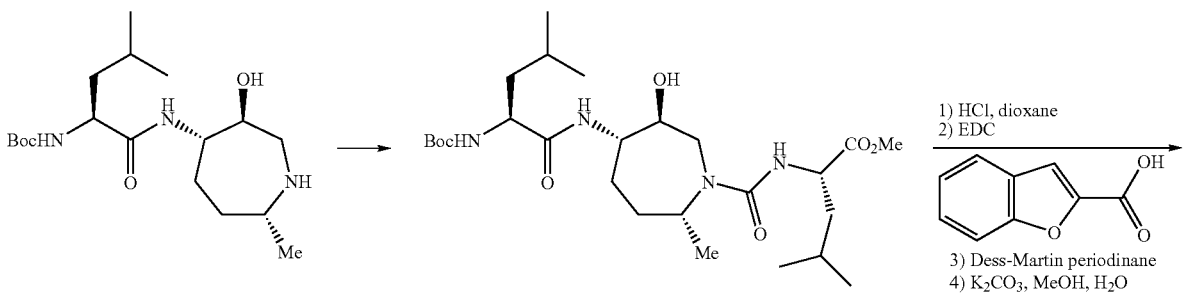

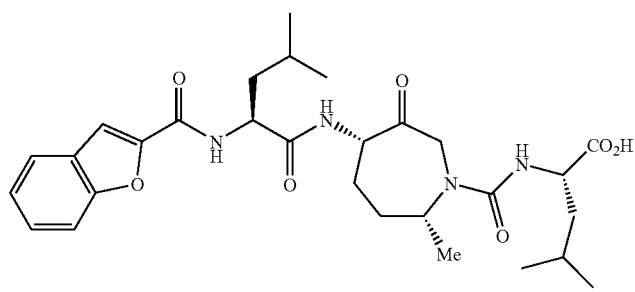

Intermediate [(S)-1-((S)-3-Hydroxy-azepan-4-ylcarbamoyl)-3-methyl-butyl]-carbamic acid tert-butyl ester, as described in Scheme 3, is acylated with an isocyanate such as (S)-(−)-2-isocyanato-4-methylvaleric acid methyl ester. Deprotection of the Boc group followed by acylation with an acylating agent such as benzofuran-2-carboxylic acid, HBTU, NMM, and final oxidation of the secondary alcohol to the ketone with an oxidant such as Dess-Martin periodinane or sulfur trioxide-pyridine provides the desired products.

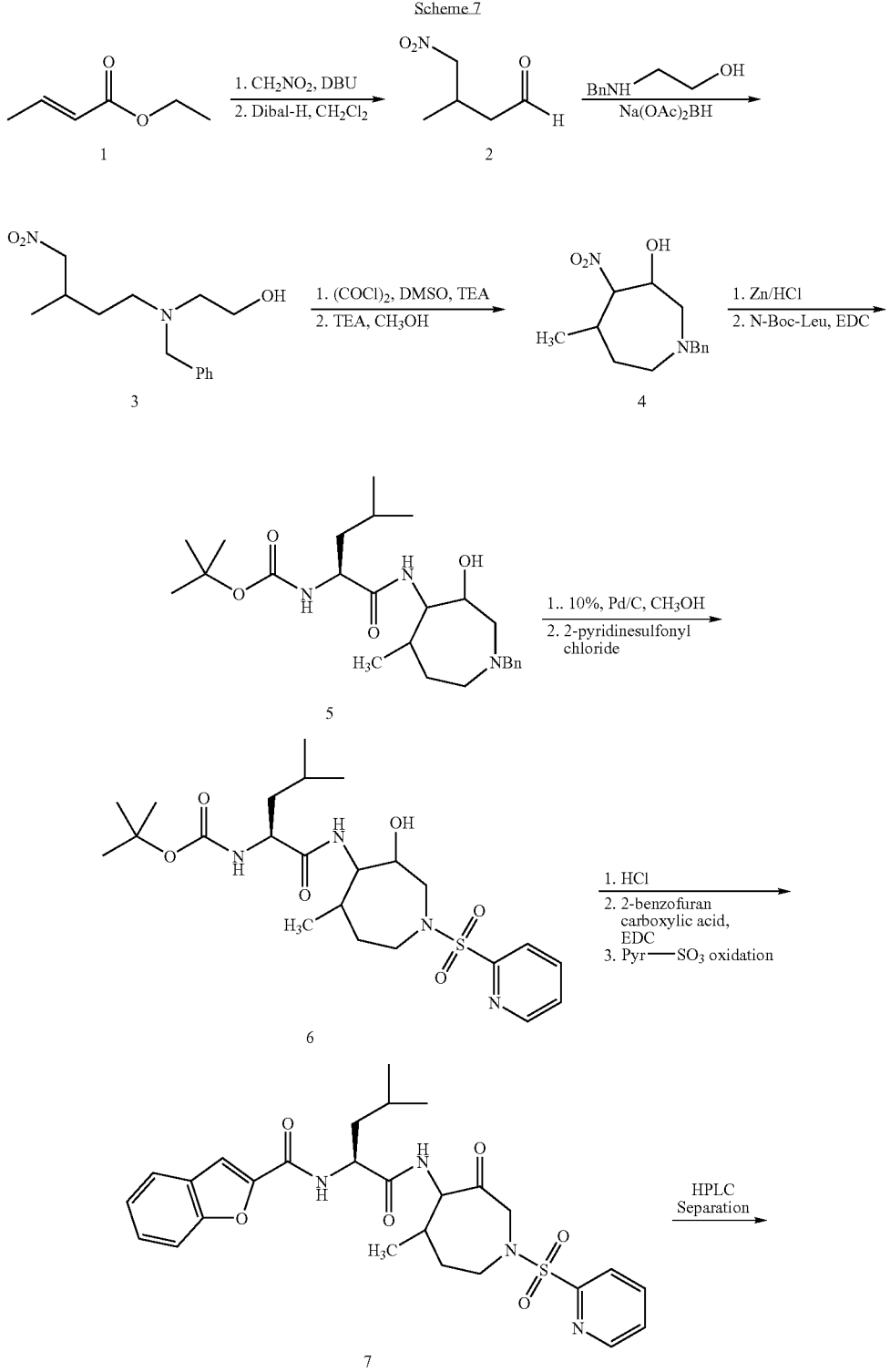

-continued

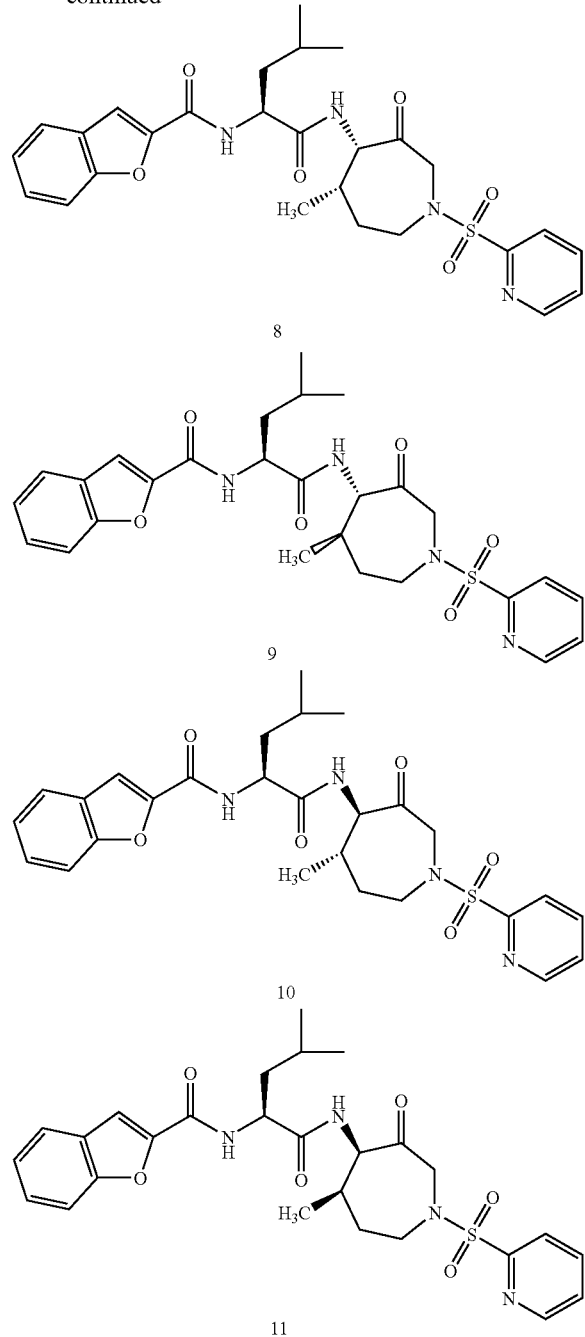

The synthesis of the C-5 methyl azepinone, 4,5 (R,S)-benzofuran-2-carboxylic acid {(S)-3-methyl-1-[5-methyl-3-oxo-1-(pyridine-2-sulfonyl)-azepan-4-ylcarbamoyl]-butyl}amide, (Example 61) is outlined above in Scheme 7. Michael addition of nitromethane to ethyl crotonate 7-1 followed by reduction of the intermediate ester with a reducing agent such as diisobutyl aluminum hydride (Dibal-H) provides the aldehyde 7-2. Reductive amination of 7-2 with N-benzyl ethanolamine in the presence of a reducing agent such as sodium triacetoxyborohydride provides the nitroalcohol 7-3. Oxidation of 7-3 using an oxidant common to the art such as DMSO and oxalyl chloride followed by treatment of the crude intermediate aldehyde with a base such as triethylamine effects the nitro-aldol reaction to give the azepanol 7-4. Reduction of the nitro group with zinc in the presence of hydrochloric acid followed by coupling of the resulting amine with N-Boc-leucine in the presence of a coupling agent common to the art such as EDC provides intermediate 7-5. Reductive removal of the N-benzyl moiety with hydrogen gas in the presence of a catalyst such as 10% Pd on carbon followed by sulfonylation with a sulfonyl chloride in the presence of a base such as N-methylmorpholine or triethyl amine provides the sulfonamide intermediate 7-6. Removal of the N-Boc protecting group under acidic conditions followed by coupling of the resulting amine salt with benzofuran-2-carboxylic acid and oxidation of the alcohol with an oxidant common to the art such as pyridine sulfur trioxide complex or Dess-Martin periodinane provides the ketone 7. The individual diastereomers of 7-7 may be separated by HPLC methods to provide diastereomers 7-8, 7-9, 7-10 and 7-11.

known to those of ordinary skill in the art and can be found in standard reference books, such as the COMPENDIUM OF ORGANIC SYNTHETIC METHODS, Vol. I-VI (published by Wiley-Interscience).

Coupling methods to form amide bonds herein are generally well known to the art. The methods of peptide synthesis generally set forth by Bodansky et al., THE PRACTICE OF

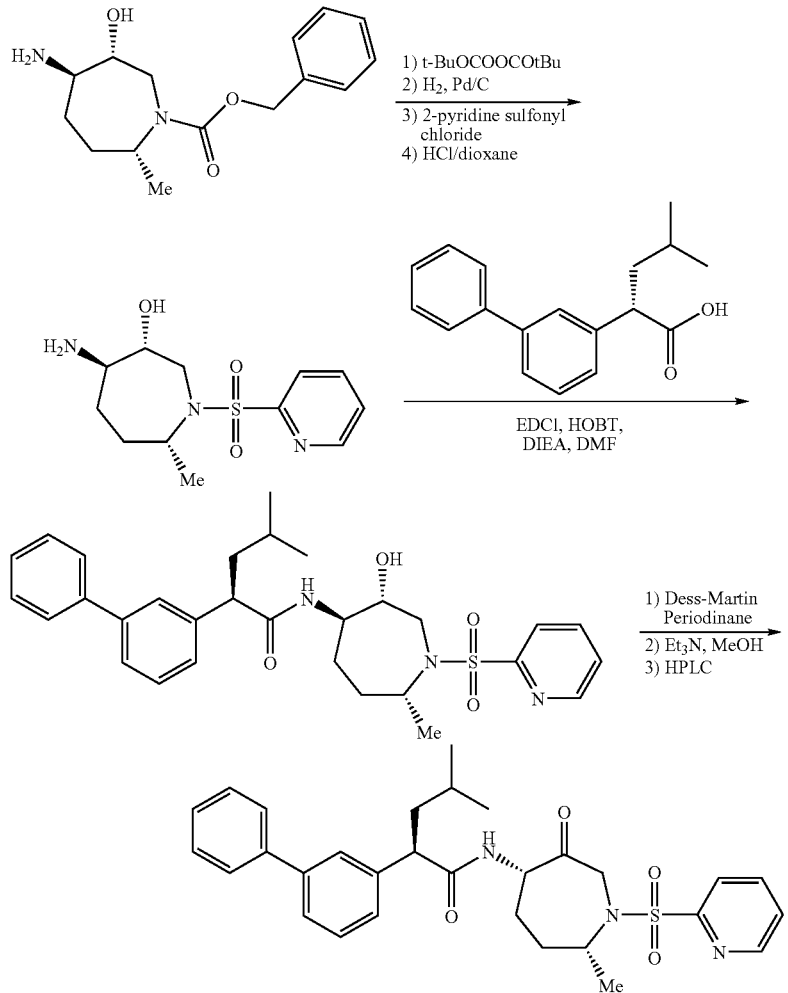

Scheme 8

Intermediate (2R,5R,6R)-5-Amino-6-hydroxy-2-methyl-azepane-1-carboxylic acid benzyl ester (derived from the major epoxide of Scheme 3) is protected with Boc anhydride. Then, the Cbz group is removed by hydrogenolysis. Sulfonylation is then accomplished with 2-pyridine sulfonyl chloride, and the Boc group is removed with hydrochloric acid in dioxane. The primary amine is then coupled with 2-biphenyl-3-yl-4-methyl-pentanoic acid (as described in. *J. Am. Chem. Soc.* 1997, 120, 9114), then the secondary alcohol to the ketone with an oxidant such as Dess-Martin periodinane or sulfur trioxide-pyridine. The azepanone is then epimerized using triethylamine in MeOH to provide a mixture of diastereomers. The desired compound is obtained by separation of the diastereomers using chiral HPLC.

The starting materials used herein are commercially available amino acids or are prepared by routine methods well PEPTIDE SYNTHESIS, Springer-Verlag, Berlin, 1984; E. Gross and J. Meienhofer, THE PEPTIDES, Vol. 1, 1-284 (1979); and J. M. Stewart and J. D. Young, SOLID PHASE PEPTIDE SYNTHESIS, 2d Ed., Pierce Chemical Co., Rockford, Ill., 1984. are generally illustrative of the technique and are incorporated herein by reference.

Synthetic methods to prepare the compounds of this invention frequently employ protective groups to mask a reactive functionality or minimize unwanted side reactions. Such protective groups are described generally in Green, T. W, PROTECTIVE GROUPS IN ORGANIC SYNTHESIS, John Wiley & Sons, New York (1981). The term "amino protecting groups" generally refers to the Boc, acetyl, benzoyl, Fmoc and Cbz groups and derivatives thereof as known to the art.

Methods for protection and deprotection, and replacement of an amino protecting group with another moiety are well known.

Acid addition salts of the compounds of Formula I are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts. Halides, sulfate, phosphate, alkanoates (such as acetate and trifluoroacetate), benzoates, and sulfonates (such as mesylate) are examples of anions present in pharmaceutically acceptable salts.

This invention also provides a pharmaceutical composition which comprises a compound according to Formula I and a pharmaceutically acceptable carrier, diluent or excipient. Accordingly, the compounds of Formula I may be used in the manufacture of a medicament. Pharmaceutical compositions of the compounds of Formula I prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

Novel Intermediates

Referring to the methods of preparing the compounds of Formula I set forth in Schemes 1-8 above, the skilled artisan will appreciate that the present invention includes all novel intermediates required to make the compounds of Formula I. In particular, the present invention provides the compounds of Formula II:

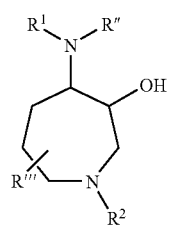

II wherein:

$R^1$ is selected from the group consisting of:

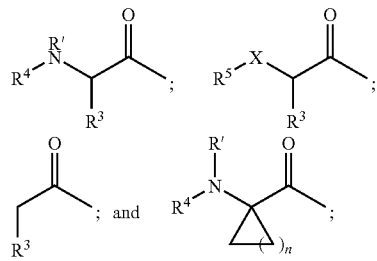

$R^2$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^9$C(O)—, $R^9$C(S)—, $R^9SO_2$—, $R^9$OC(O)—, $R^9R^{11}$NC(O)—, $R^9R^{11}$NC(S)—, $R^9(R^{11})NSO_2$—

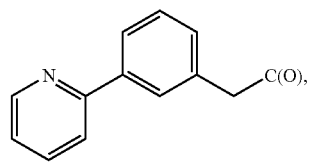

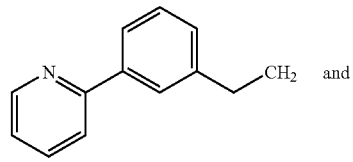

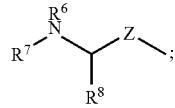

$R^3$ is selected from the group consisting of: H, $C_{1-6}$alkyl, $C_{3-6}$cycloalkyl-$C_{0-6}$alkyl, $C_{2-6}$alkenyl, $C_{2-6}$alkynyl, Het$C_{0-6}$ alkyl, ArC$_{0-6}$alkyl, Ar—ArC$_{0-6}$alkyl, Ar—HetC$_{0-6}$alkyl, Het-ArC$_{0-6}$alkyl, and Het-HetC$_{0-6}$alkyl;

R$^3$ and R' may be connected to form a pyrrolidine, piperidine or morpholine ring;

R$^4$ is selected from the group consisting of: H, C$_{1-6}$alkyl, C$_{3-6}$cycloalkyl-C$_{0-6}$alkyl, Ar—C$_{0-6}$alkyl, Het-C$_{0-6}$alkyl, R$^5$C(O)—, R$^5$C(S)—, R$^5$SO$_2$—, R$^5$OC(O)—, R$^5$R$^{12}$NC(O)—, and R$^5$R$^{12}$NC(S)—;

R$^5$ is selected from the group consisting of: H, C$_{1-6}$alkyl, C$_{2-6}$alkenyl, C$_{2-6}$alkynyl, C$_{3-6}$cycloalkyl-C$_{0-6}$alkyl, Ar—C$_{0-6}$ alkyl and Het-C$_{0-6}$alkyl;

R$^6$ is selected from the group consisting of: H, C$_{1-6}$alkyl, Ar—C$_{0-6}$alkyl, or Het-C$_{0-6}$alkyl;

R$^7$ is selected from the group consisting of: H, C$_{1-6}$alkyl, C$_{3-6}$cycloalkyl-C$_{0-6}$alkyl, Ar—C$_{0-6}$alkyl, Het-C$_{0-6}$alkyl, R$^{10}$C(O)—, R$^{10}$C(S)—, R$^{10}$SO$_2$—, R$^{10}$OC(O)—, R$^{10}$R$^{13}$NC(O)—, and R$^{10}$R$^{13}$NC(S)—;

R$^8$ is selected from the group consisting of: H, C$_{1-6}$alkyl, C$_{2-6}$alkenyl, C$_{2-6}$alkynyl, HetC$_{0-6}$alkyl and ArC$_{0-6}$alkyl;

R$^9$ is selected from the group consisting of: C$_{1-6}$alkyl, C$_{3-6}$cycloalkyl-C$_{0-6}$alkyl, Ar—C$_{0-6}$alkyl and Het-C$_{0-6}$alkyl;

R$^{10}$ is independently selected from the group consisting of: C$_{1-6}$alkyl, C$_{3-6}$cycloalkyl-C$_{0-6}$alkyl, Ar—C$_{0-6}$alkyl and Het-C$_{0-6}$alkyl;

R$^{11}$ is selected from the group consisting of: H, C$_{1-6}$alkyl, C$_{3-6}$cycloalkyl-C$_{0-6}$alkyl, Ar—C$_{0-6}$alkyl, and Het-C$_{0-6}$alkyl;

R$^{12}$ is selected from the group consisting of: H, C$_{1-6}$alkyl, Ar—C$_{0-6}$alkyl, and Het-C$_{0-6}$alkyl;

R$^{13}$ is selected from the group consisting of: H, C$_{1-6}$alkyl, Ar—C$_{0-6}$alkyl, and Het-C$_{0-6}$alkyl;

R' is selected from the group consisting of: H, C$_{1-6}$alkyl, Ar—C$_{0-6}$alkyl, and Het-C$_{0-6}$alkyl;

R" is selected from the group consisting of: H, C$_{1-6}$alkyl, Ar—C$_{0-6}$alkyl, or Het-C$_{0-6}$alkyl;

R''' is selected from the group consisting of:

C$_{1-6}$alkyl, especially selected from the group consisting of: methyl, ethyl, propyl, butyl, pentyl and hexyl, more especially methyl;

preferably 5-, 6- or 7-C$_{1-6}$alkyl, especially selected from the group consisting of: 5-, 6- or 7-methyl, -ethyl, -propyl, -butyl, -pentyl and -hexyl, more especially 5-, 6- or 7-methyl;

more preferably 6- or 7-C$_{1-6}$alkyl, especially selected from the group consisting of: 6- or 7-methyl, -ethyl, -propyl, -butyl, -pentyl and -hexyl, more especially 6- or 7-methyl;

yet more preferably cis-7-C$_{1-6}$alkyl as shown in Formula Ia:

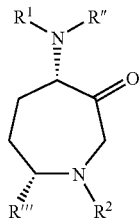

wherein R''' is C$_{1-6}$alkyl, especially selected from the group consisting of: methyl, ethyl, propyl, butyl, pentyl and hexyl;

most preferably cis-7-methyl, as shown in Formula Ia wherein R''' is methyl;

X is selected from the group consisting of: CH$_2$, S, and O;
Z is selected from the group consisting of: C(O) and CH$_2$;
n is an integer from 1 to 5;

and pharmaceutically acceptable salts, hydrates and solvates thereof.

The following compounds are preferred novel intermediates:

3-methyl-1-(pyridine-2-sulfonyl)-2,3,4,7-tetrahydro-1H-azepine;

5-methyl-3-(pyridine-2-sulfonyl)-8-oxa-3-aza-bicyclo[5.1.0]octane;

4-azido-5-methyl-1-(pyridine-2-sulfonyl)-azepan-3-ol;

4-amino-6-methyl-1-(pyridine-2-sulfonyl)-azepan-3-ol;

{(S)-1-[3-hydroxy-6-methyl-1-(pyridine-2-sulfonyl)-azepan-4-ylcarbamoyl]-3-methyl-butyl}-carbamic acid tert-butyl ester;

5-methoxy-benzofuran-2-carboxylic acid {(S)-1-[3-hydroxy-6-methyl-1-(pyridine-2-sulfonyl)-azepan-4-ylcarbamoyl]-3-methyl-butyl )-amide;

allyl-(1-methyl-pent-4-enyl)-carbamic acid benzyl ester;

2-methyl-2,3,4,7-tetrahydro-azepine-1-carboxylic acid benzyl ester;

4-methyl-8-oxa-3-aza-bicyclo[5.1.0]octane-3-carboxylic acid benzyl ester;

5-azido-6-hydroxy-2-methyl-azepane-1-carboxylic acid benzyl ester;

5-amino-6-hydroxy-2-methyl-azepane-1-carboxylic acid benzyl ester;

(2R,5S,6S)-5-((S)-2-tert-butoxycarbonylamino-4-methylpentanoylamino)-6-hydroxy-2-methyl-azepane-1-carboxylic acid benzyl ester;

(2S,5R,6R)-5-((S)-2-tert-butoxycarbonylamino-4-methylpentanoylamino)-6-hydroxy-2-methyl-azepane-1-carboxylic acid benzyl ester;

[(S)-1-((3S,4S,7R)-3-hydroxy-7-methyl-azepan-4-ylcarbamoyl)-3-methyl-butyl]-carbamic acid tert-butyl ester;

[(S)-1-((3R,4R,7S)-3-hydroxy-7-methyl-azepan-4-ylcarbamoyl)-3-methyl-butyl]-carbamic acid tert-butyl ester;

[(S)-1-((3S,4S,7R)-1-benzenesulfonyl-3-hydroxy-7-methyl-azepan-4-ylcarbamoyl)-3-methyl-butyl]-carbamic acid tert-butyl ester;

[(S)-1-((3R,4R,7S)-1-benzenesulfonyl-3-hydroxy-7-methyl-azepan-4-ylcarbamoyl)-3-methyl-butyl]-carbamic acid tert-butyl ester;

(S)-2-amino-4-methyl-pentanoic acid ((3S,4S,7R)-1-(2-pyridine)-sulfonyl-3-hydroxy-7-methyl-azepan-4-yl)-amide;

(S)-2-amino-4-methyl-pentanoic acid ((3R,4R,7S)-1-(2-pyridine)-sulfonyl-3-hydroxy-7-methyl-azepan-4-yl)-amide;

benzofuran-2-carboxylic acid {(S)-1-[(3S,4S,7R)-3-hydroxy-7-methyl-1-(pyridine-2-sulfonyl)-azepan-4-ylcarbamoyl]-3-methyl-butyl}-amide;

benzofuran-2-carboxylic acid {(S)-1-[(3R,4R,7S)-3-hydroxy-7-methyl-1-(pyridine-2-sulfonyl)-azepan-4-ylcarbamoyl]-3-methyl-butyl}-amide;

((R)-1-methyl-pent-4-enyl)-carbamic acid benzyl ester;
allyl-((R)-1-methyl-pent-4-enyl)-carbamic acid benzyl ester;
2-methyl-2,3,4,7-tetrahydro-azepine-1-carboxylic acid benzyl ester;

(1S,4R,7R)-4-methyl-8-oxa-3-aza-bicyclo[5.1.0]octane-3-carboxylic acid benzyl ester;

(2R,5S,6S)-5-azido-6-hydroxy-2-methyl-azepane-1-carboxylic acid benzyl ester;

(2R,5S,6S)-5-amino-6-hydroxy-2-methyl-azepane-1-carboxylic acid benzyl ester;

(2R,5S,6S)-5-((S)-2-tert-butoxycarbonylamino-4-methylpentanoylamino)-6-hydroxy-2-methyl-azepane-1-carboxylic acid benzyl ester;

[(S)-1-((3S,4S,7R)-3-hydroxy-7-methyl-azepan-4-ylcarbamoyl)-3-methyl-butyl]-carbamic acid tert-butyl ester;
[(S)-1-((3S,4S,7R)-2-pyridinesulfonyl-3-hydroxy-7-methyl-azepan-4-ylcarbamoyl)-3-methyl-butyl]-carbamic acid tert-butyl ester;
(S)-2-amino-4-methyl-pentanoic acid ((3S,4S,7R)-1-(2-pyridine)-sulfonyl-3-hydroxy-7-methyl-azepan-4-yl)-amide;
5-methoxy-benzofuran-2-carboxylic acid {(S)-3-methyl-1-[(3R,4R,6R)-6-methyl-3-hydroxy-1-(pyridine-2-sulfonyl)-azepan-4-ylcarbamoyl]-butyl}-amide;
benzo[b]thiophene-2-carboxylic acid {(S)-1-[(3S,4S,6S)-6-methyl-3-hydroxy-1-(pyridine-2-sulfonyl)-azepan-4-ylcarbamoyl]-3-methyl-butyl}-amide;
benzo[b]thiophene-2-carboxylic acid {(S)-1-[(3R,4R,6R)-6-methyl-3-hydroxy-1-(pyridine-2-sulfonyl)-azepan-4-ylcarbamoyl]-3-methyl-butyl}-amide;
3-methyl-benzofuran-2-carboxylic acid {(S)-1-[(3S,4S,6S)-6-methyl-3-hydroxy-1-(pyridine-2-sulfonyl)-azepan-4-ylcarbamoyl]-3-methyl-butyl}-amide;
3-methyl-benzofuran-2-carboxylic acid {(S)-1-[(3R,4R,6R)-6-methyl-3-hydroxy-1-(pyridine-2-sulfonyl)-azepan-4-ylcarbamoyl]-3-methyl-butyl}-amide;
thieno[3,2-b]thiophene-2-carboxylic acid {(S)-1-[(3S,4S,6S)-6-methyl-3-hydroxy-1-(pyridine-2-sulfonyl)-azepan-4-ylcarbamoyl]-3-methyl-butyl}-amide;
thieno[3,2-b]thiophene-2-carboxylic acid {(S)-1-[(3S,4R,6R)-6-methyl-3-hydroxy-1-(pyridine-2-sulfonyl)-azepan-4-ylcarbamoyl]-3-methyl-butyl}-amide;
benzofuran-2-carboxylic acid {(S)-3-methyl-1-[(3S,4S,7R)-7-methyl-3-hydroxy-1-(pyridine-2-sulfonyl)-azepan-4-ylcarbamoyl]-butyl}-amide;
benzofuran-2-carboxylic acid {(S)-3-methyl-1-[(3S,4S,7S)-7-methyl-3-hydroxy-1-(pyridine-2-sulfonyl)-azepan-4-ylcarbamoyl]-butyl}-amide;
benzofuran-2-carboxylic acid {(S)-3-methyl-1-[(3R,4R,7S)-7-methyl-3-hydroxy-1-(pyridine-2-sulfonyl)-azepan-4-ylcarbamoyl]-butyl}-amide;
benzofuran-2-carboxylic acid {(S)-3-methyl-1-[(3R,4R,7R)-7-methyl-3-hydroxy-1-(pyridine-2-sulfonyl)-azepan-4-ylcarbamoyl]-butyl}-amide;
((R)-2-iodo-1-methyl-ethyl)-carbamic acid benzyl ester
((R)-1-methyl-pent-4-enyl)-carbamic acid benzyl ester;
allyl-((R)-1-methyl-pent-4-enyl)-carbamic acid benzyl ester;
2-methyl-2,3,4,7-tetrahydro-azepine-1-carboxylic acid benzyl ester;
(1S,4R,7R)-4-methyl-8-oxa-3-aza-bicyclo[5.1.0]octane-3-carboxylic acid benzyl ester;
(2R,5S,6S)-5-azido-6-hydroxy-2-methyl-azepane-1-carboxylic acid benzyl ester;
(2R,5S,6S)-5-amino-6-hydroxy-2-methyl-azepane-1-carboxylic acid benzyl ester;
(2R,5S,6S)-5-((S)-2-tert-butoxycarbonylamino-4-methyl-pentanoylamino)-6-hydroxy-2-methyl-azepane-1-carboxylic acid benzyl ester;
[(S)-1-((3S,4S,7R)-3-hydroxy-7-methyl-azepan-4-ylcarbamoyl)-3-methyl-butyl]-carbamic acid tert-butyl ester;
[(S)-1-((3S,4S,7R)-2-pyridinesulfonyl-3-hydroxy-7-methyl-azepan-4-ylcarbamoyl)-3-methyl-butyl]-carbamic acid tert-butyl ester;
(S)-2-amino-4-methyl-pentanoic acid ((3S,4S,7R)-1-(2-pyridine)-sulfonyl-3-hydroxy-7-methyl-azepan-4-yl)-amide;
furo[3,2-b]pyridine-2-carboxylic acid {(S)-1-[(3S,4S,7R)-3-hydroxy-7-methyl-1-(pyridine-2-sulfonyl)-azepan-4-ylcarbamoyl]-3-methyl-butyl}-amide;
furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide;
3-methyl-furo[3,2-b]pyridine-2-carboxylic acid {(S)-1-[(3S,4S,7R)-3-hydroxy-7-methyl-1-(pyridine-2-sulfonyl)-azepan-4-ylcarbamoyl]-3-methyl-butyl}-amide;
3-methyl-furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide;
quinoline-6-carboxylic acid {(S)-3-methyl-1-[(3S,4S,7R)-7-methyl-3-hydroxy-1-(pyridine-2-sulfonyl)-azepan-4-ylcarbamoyl]-butyl}-amide;
quinoline-3-carboxylic acid {(S)-3-methyl-1-[(3S,4S,7R)-7-methyl-3-hydroxy-1-(pyridine-2-sulfonyl)-azepan-4-ylcarbamoyl]-butyl}-amide;
5-methoxy-benzofuran-2-carboxylic acid {(S)-3-methyl-1-[(3S,4S,7R)-7-methyl-3-hydroxy-1-(pyridine-2-sulfonyl)-azepan-4-ylcarbamoyl]-butyl}-amide;
3-methyl-benzofuran-2-carboxylic acid {(S)-3-methyl-1-[(3S,4S,7R)-7-methyl-3-hydroxy-1-(pyridine-2-sulfonyl)-azepan-4-ylcarbamoyl]-butyl}-amide;
thieno[3,2-b]thiophene-2-carboxylic acid {(S)-3-methyl-1-[(3S,4S,7R)-7-methyl-3-hydroxy-1-(pyridine-2-sulfonyl)-azepan-4-ylcarbamoyl]-butyl}-amide;
quinoxaline-2-carboxylic acid {(S)-3-methyl-1-[(3S,4S,7R)-7-methyl-3-hydroxy-1-(pyridine-2-sulfonyl)-azepan-4-ylcarbamoyl]-butyl}-amide;
thieno[3,2-b]thiophene-2-carboxylic acid {(S)-3-methyl-1-[(3S,4S,7R)-7-methyl-3-hydroxy-1-(1-oxy-pyridine-2-sulfonyl)-azepan-4-ylcarbamoyl]-butyl}-amide;
3-methyl-benzofuran-2-carboxylicacid {(S)-3-methyl-1-[(3S,4S,7R)-7-methyl-3-hydroxy-1-(1-oxy-pyridine-2-sulfonyl)-azepan-4-ylcarbamoyl]-butyl}-amide;
benzofuran-2-carboxylic acid {(S)-3-methyl-1-[(3S,4S,7R)-7-methyl-3-hydroxy-1-(1-oxy-pyridine-2-sulfonyl)-azepan-4-ylcarbamoyl]-butyl}-amide;
quinoline-2-carboxylic acid {(S)-3-methyl-1-[(3S,4S,7R)-7-methyl-3-hydroxy-1-(1-oxy-pyridine-2-sulfonyl)-azepan-4-ylcarbamoyl]-butyl}-amide;
5,6-difluoro-benzofuran-2-carboxylic acid {(S)-3-methyl-1-[(3S,4S,7R)-7-methyl-3-hydroxy-1-(1-oxy-pyridine-2-sulfonyl)-azepan-4-ylcarbamoyl]-butyl}-amide;
5-fluoro-3-methyl-benzofuran-2-carboxylic acid {(S)-3-methyl-1-[(3S,4S,7R)-7-methyl-3-hydroxy-1-(1-oxy-pyridine-2-sulfonyl)-azepan-4-ylcarbamoyl]-butyl}-amide;
5-fluoro-benzofuran-2-carboxylic acid {(S)-3-methyl-1-[(3S,4S,7R)-7-methyl-3-hydroxy-1-(1-oxy-pyridine-2-sulfonyl)-azepan-4-ylcarbamoyl]-butyl}-amide;
3-methyl-furo[3,2-b]]pyridine-2-carboxylic acid {(S)-3-methyl-1-[(3S,4S,7R)-7-methyl-3-hydroxy-1-(1-oxy-pyridine-2-sulfonyl)-azepan-4-ylcarbamoyl]-butyl}-amide;
cyclohexanecarboxylic acid {(S)-3-methyl-1-[(3S,4S,7R)-7-methyl-3-hydroxy-1-(1-oxy-pyridine-2-sulfonyl)-azepan-4-ylcarbamoyl]-butyl}-amide;
(S)-2-(2-cyclohexyl-ethanoylamino)-4-methyl-pentanoic acid [(3S,4S,7R)-7-methyl-3-hydroxy-1-(1-oxy-pyridine-2-sulfonyl)-azepan-4-yl]-amide;
(S)-2-(3-cyclohexyl-propanoylamino)-4-methyl-pentanoic acid [(3S,4S,7R)-7-methyl-3-hydroxy-1-(1-oxy-pyridine-2-sulfonyl)-azepan-4-yl]-amide;
(S)-2-(4-cyclohexyl-butanoylamino)-4-methyl-pentanoic acid [(3S,4S,7R)-7-methyl-3-hydroxy-1-(1-oxy-pyridine-2-sulfonyl)-azepan-4-yl]-amide;
(S)-2-(5-cyclohexyl-pentanoylamino)-4-methyl-pentanoic acid [(3S,4S,7R)-7-methyl-3-hydroxy-1-(1-oxy-pyridine-2-sulfonyl)-azepan-4-yl]-amide;

benzofuran-2-carboxylic acid {(S)-3-methyl-1-[(3S,4S,7R)-7-methyl-3-hydroxy-1-(5-trifluoromethyl-pyridine-2-sulfonyl)-azepan-4-ylcarbamoyl]-butyl}-amide;

5-fluoro-benzofuran-2-carboxylic acid {(S)-3-methyl-1-[(3S,4S,7R)-7-methyl-3-hydroxy-1-(5-trifluoromethyl-pyridine-2-sulfonyl)-azepan-4-ylcarbamoyl]-butyl}-amide;

thieno[3,2-b]thiophene-2-carboxylic acid {(S)-3-methyl-1-[(3S,4S,7R)-7-methyl-3-hydroxy-1-(5-trifluoromethyl-pyridine-2-sulfonyl)-azepan-4-ylcarbamoyl]-butyl}-amide;

benzofuran-2-carboxylic acid {1-[(3S,4S,7R)-7-methyl-3-hydroxy-1-(pyridine-2-sulfonyl)-azepan-4-ylcarbamoyl]-cyclohexyl}-amide;

thiophene-3-carboxylic acid {(S)-3,3-dimethyl-1-[(3S,4S,7R)-7-methyl-3-hydroxy-1-(pyridine-2-sulfonyl)-azepan-4-ylcarbamoyl]-butyl}-amide;

furan-2-carboxylic acid {(S)-3,3-dimethyl-1-[(3S,4S,7R)-7-methyl-3-hydroxy-1-(pyridine-2-sulfonyl)-azepan-4-ylcarbamoyl]-butyl}-amide;

thieno[3,2-b]thiophene-2-carboxylic acid {(S)-3,3-dimethyl-1-[(3S,4S,7R)-7-methyl-3-hydroxy-1-(pyridine-2-sulfonyl)-azepan-4-ylcarbamoyl]-butyl}-amide;

benzofuran-2-carboxylic acid {(S)-2-cyclohexyl-1-[(3S,4S,7R)-7-methyl-3-hydroxy-1-(pyridine-2-sulfonyl)-azepan-4-ylcarbamoyl]-ethyl}-amide;

furan-2-carboxylic acid {(S)-2-cyclohexyl-1-[(3S,4S,7R)-7-methyl-3-hydroxy-1-(pyridine-2-sulfonyl)-azepan-4-ylcarbamoyl]-ethyl}-amide;

thiophene-3-carboxylic acid {(S)-2-cyclohexyl-1-[(3S,4S,7R)-7-methyl-3-hydroxy-1-(pyridine-2-sulfonyl)-azepan-4-ylcarbamoyl]-ethyl}-amide;

3-methyl-furo[3,2-b]-pyridine-2-carboxylic acid {(S)-2-cyclohexyl-1-[(3S,4S,7R)-7-methyl-3-hydroxy-1-(pyridine-2-sulfonyl)-azepan-4-ylcarbamoyl]-ethyl}-amide;

(2R,4aR,8aR)-octahydro-benzo[1,4]dioxine-2-carboxylic acid [(S)-1-((3S,4S,7R)-1-methanesulfonyl-7-methyl-3-hydroxy-azepan-4-ylcarbamoyl)-3-methyl-butyl]-amide;

furan-2-carboxylic acid [(S)-2-cyclohexyl-1-((3S,4S,7R)-7-methyl-3-hydroxy-1-propyl-azepan-4-ylcarbamoyl)-ethyl]-amide;

thiophene-3-carboxylic acid [(S)-2-cyclohexyl-1-((3S,4S,7R)-7-methyl-3-hydroxy-1-propyl-azepan-4-ylcarbamoyl)-ethyl]-amide;

benzofuran-2-carboxylic acid [(S)-2-cyclohexyl-1-((3S,4S,7R)-7-methyl-3-hydroxy-1-propyl-azepan-4-ylcarbamoyl)-ethyl]-amide;

1-(3-cyclohexyl-propanoylamino)-cyclohexanecarboxylic acid ((3S,4S,7R)-1-cyclohexylmethyl-7-methyl-3-hydroxy-azepan-4-yl)-amide;

benzofuran-2-carboxylic acid [1-((3S,4S,7R)-1-cyclohexylmethyl-7-methyl-3-hydroxy-azepan-4-ylcarbamoyl)-cyclohexyl]-amide;

benzofuran-2-carboxylic acid [(S)-3-methyl-1-((3S,4S,7R)-7-methyl-3-hydroxy-1-propyl-azepan-4-ylcarbamoyl)-butyl]-amide;

(2R,5S)-5-((S)-2-tert-butoxycarbonylamino-4-methyl-pentanoylamino)-2-methyl-6-hydroxy-azepane-1-carboxylic acid benzyl ester;

benzofuran-2-carboxylic acid {(S)-3-methyl-1-[(3S,4S,7R)-7-methyl-3-hydroxy-1-(1-morpholin-4-yl-methanoyl)-3-hydroxy-azepan-4-ylcarbamoyl]-butyl}-amide;

(S)-2-(3-cyclohexyl-propanoylamino)-4-methyl-pentanoic acid [(3S,4S,7R)-7-methyl-1-(1-morpholin-4-yl-methanoyl)-3-hydroxy-azepan-4-yl]-amide;

(2R,5S,6S)-5-{(S)-2-[(1-benzofuran-2-yl-methanoyl)-amino]-4-methyl-pentanoylamino}-2-methyl-6-hydroxy-azepane-1-carboxylic acid (tetrahydro-pyran-4-yl)-amide;

(S)-2-{[1-((2R,5S,6S)-5-{(S)-2-[(1-benzofuran-2-yl-methanoyl)-amino]-4-methyl-pentanoylamino}-2-methyl-6-hydroxy-azepan-1-yl)-methanoyl]-amino)-4-methyl-pentanoic acid methyl ester;

(S)-2-{[1-(4-{(S)-2-[(1-benzofuran-2-yl-methanoyl)-amino]-4-methyl-pentanoylamino}-3-hydroxy-azepan-1-yl)-methanoyl]-amino)-4-methyl-pentanoicacid methyl ester;

(S)-4-methyl-2-{[1-((2R,5S,6S)-2-methyl-5-f (S)-4-methyl-2-[(1-quinolin-8-yl-methanoyl)-amino]-pentanoylamino}-6-hydroxy-azepan-1-yl)-methanoyl]-amino}-pentanoic acid methyl ester;

(R)-2-{[1-(4-{(S)-2-[(1-benzofuran-2-yl-methanoyl)-amino]-4-methyl-pentanoylamino}-3-hydroxy-azepan-1-yl)-methanoyl]-amino}-4-methyl-pentanoic acid methyl ester;

2-biphenyl-3-yl-4-methyl-pentanoic acid [(3R,4R,7R)-7-methyl-3-hydroxy-1-(pyridine-2-sulfonyl)-azepan-4-yl]-amide;

3-methyl-furo[3,2-b]-pyridine-2-carboxylic acid {1-[(4S,7R)-7-methyl-3-hydroxy-1-(pyridine-2-sulfonyl)-azepan-4-ylcarbamoyl]-cyclohexyl}-amide; and 1-(3-cyclohexyl-propanoylamino)-cyclohexanecarboxylic acid [(4S,7R)-7-methyl-3-hydroxy-1-(pyridine-2-sulfonyl)-azepan-4-yl]-amide.

Process for Synthesis of Inventive Compounds

Referring to Schemes 1-8 herein above, the present invention provides a process for the synthesis of compounds of Formula (I) comprising the step of oxidizing the appropriate compound of Formula (II) with an oxidant to provide the compound of Formula (I) as a mixture of diastereomers. Preferably the oxidant is sulfur trioxide-pyridine complex.

Referring to Scheme 4, the present invention also provides a process for the synthesis of deuterated compounds of Formula (I). Specifically, when a deuterated isomer is desired, an additional step, following the oxidation step, of deuterating the protonated isomer with a deuterating agent to provide the deuterated compound of Formula (I) as a mixture of diastereomers is added to the synthesis. Preferably, the deuterating agent is $CD_3OD:D_2O$ (10:1) in triethylamine.

The process further comprises the step of separating the diastereomers of Formula (I) by separating means, preferably by high presssure liquid chromatography (HPLC).

Utility of the Present Invention

The compounds of Formula I are useful as protease inhibitors, particularly as inhibitors of cysteine and serine proteases, more particularly as inhibitors of cysteine proteases, even more particularly as inhibitors of cysteine proteases of the papain superfamily, yet more particularly as inhibitors of cysteine proteases of the cathepsin family, most particularly as inhibitors of cathepsin K. The present invention also provides useful compositions and formulations of said compounds, including pharmaceutical compositions and formulations of said compounds.

The present compounds are useful for treating diseases in which cysteine proteases are implicated, including infections by *pneumocystis carinii, trypsanoma cruzi, trypsanoma brucei*, and *Crithidia fusiculata*; as well as in schistosomiasis, malaria, tumor metastasis, metachromatic leukodystrophy, muscular dystrophy, amytrophy; and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease; hypercalcemia of malignancy, and metabolic bone disease.

Parasites known to utilize cysteine proteases in their life cycle (and the diseases caused by these parasites) include *Trypanosoma cruzi, Trypanosoma Brucei* [trypanosomiasis (African sleeping sickness, Chagas disease)], *Leishmania mexicana, Leishmania pifanoi, Leishmania major* (leishmaniasis), *Schistosoma mansoni* (schistosomiasis), *Onchocerca volvulus* [onchocerciasis (river blindness)] *Brugia pahangi, Entamoeba histolytica, Giardia lambia,* the helminths, *Haemonchus contortus* and *Fasciola hepatica,* as well as helminths of the genera *Spirometra, Trichinella, Necator* and *Ascaris,* and protozoa of the genera *Cryptosporidium, Eimeria, Toxoplasma* and *Naegleria.* The compounds of the present invention are suitable for treating diseases caused by these parasites which may be therapeutically modified by altering the activity of cysteine proteases. In particular, the present compounds are useful for treating malaria by inhibiting falcipain.

Metastatic neoplastic cells also typically express high levels of proteolytic enzymes that degrade the surrounding matrix, and certain tumors and metastatic neoplasias may be effectively treated with the compounds of this invention.

The present invention also provides methods of treatment of diseases caused by pathological levels of proteases, particularly cysteine and serine proteases, more particularly cysteine proteases, even more particularly cysteine proteases of the papain superfamily, yet more particularly cysteine proteases of the cathepsin family, which methods comprise administering to an animal, particularly a mammal, most particularly a human in need thereof a compound of the present invention. The present invention especially provides methods of treatment of diseases caused by pathological levels of cathepsin K, which methods comprise administering to an animal, particularly a mammal, most particularly a human in need thereof an inhibitor of cathepsin K, including a compound of the present invention. The present invention particularly provides methods for treating diseases in which cysteine proteases are implicated, including infections by *pneumocystis carinii, trypsanoma cruzi, trypsanoma brucei,* and *Crithidia fusiculata;* as well as in schistosomiasis, malaria, tumor metastasis, metachromatic leukodystrophy, muscular dystrophy, amytrophy, and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease, hypercalcemia of malignancy, and metabolic bone disease.

The present method provides treatment of diseases (in parentheses) caused by infection by *Trypanosoma cruzi, Trypanosoma Brucei* [trypanosomiasis (African sleeping sickness, Chagas disease)], *Leishmania mexicana, Leishmania pifanoi, Leishmania major* (leishmaniasis), *Schistosoma mansoni* (schistosomiasis), *Onchocerca volvulus* [onchocerciasis (river blindness)] *Brugia pahangi, Entamoeba histolytica, Giardia lambia,* the helminths, *Haemonchus contortus* and *Fasciola hepatica,* as well as helminths of the genera *Spirometra, Trichinella, Necator* and *Ascaris,* and protozoa of the genera *Cryptosporidium, Eimeria, Toxoplasma* and *Naegleria* by inhibiting cysteine proteases of the papain superfamily by administering to a patient in need thereof, particularly an animal, more particularly a mammal, most particularly a human being, one or more of the above-listed compounds.

Most particularly, the present invention provides a method of treating malaria, caused by infection with *Plasmodium falciparum,* by the inhibition of falcipain by administering to a patient in need thereof, particularly an animal, more particularly a mammal, most particularly a human being, one or more of the above-listed compounds.

The present method may be practiced by administering the above-listed compounds alone or in combination, with each other, or with other therapeutically effective compounds.

This invention further provides a method for treating osteoporosis or inhibiting bone loss which comprises internal administration to a patient of an effective amount of a compound of Formula I, alone or in combination with other inhibitors of bone resorption, such as bisphosphonates (i.e., allendronate), hormone replacement therapy, anti-estrogens, or calcitonin. In addition, treatment with a compound of this invention and an anabolic agent, such as bone morphogenic protein, iproflavone, may be used to prevent bone loss or to increase bone mass.

For acute therapy, parenteral administration of a compound of Formula I is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit cathepsin K. The compounds are administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention.

Biological Assays

The compounds of this invention may be tested in one of several biological assays to determine the concentration of compound which is required to have a given pharmacological effect.

Determination of Cathepsin K Proteolytic Catalytic Activity

All assays for cathepsin K were carried out with human recombinant enzyme. Standard assay conditions for the determination of kinetic constants used a fluorogenic peptide substrate, typically Cbz-Phe-Arg-AMC, and were determined in 100 mM Na acetate at pH 5.5 containing 20 mM cysteine and 5 mM EDTA. Stock substrate solutions were prepared at concentrations of 10 or 20 mM in DMSO with 20 uM final substrate concentration in the assays. All assays contained 10% DMSO. Independent experiments found that this level of DMSO had no effect on enzyme activity or kinetic constants. All assays were conducted at ambient temperature. Product fluorescence (excitation at 360 nM; emission at 460 nM) was monitored with a Perceptive Biosystems Cytofluor II fluorescent plate reader. Product progress curves were generated over 20 to 30 minutes following formation of AMC product.

Inhibition Studies

Potential inhibitors were evaluated using the progress curve method. Assays were carried out in the presence of variable concentrations of test compound. Reactions were initiated by addition of enzyme to buffered solutions of inhibitor and substrate. Data analysis was conducted according to one of two procedures depending on the appearance of the progress curves in the presence of inhibitors. For those compounds whose progress curves were linear, apparent inhibition constants ($K_{i,app}$) were calculated according to equation 1 (Brandt et al., *Biochemitsry*, 1989, 28, 140):

$$v = V_m A / [K_a(1 + 1/K_{i,app}) + A] \quad (1)$$

where v is the velocity of the reaction with maximal velocity $V_m$, A is the concentration of substrate with Michaelis constant of $K_a$, and I is the concentration of inhibitor.

For those compounds whose progress curves showed downward curvature characteristic of time-dependent inhibition, the data from individual sets was analyzed to give $k_{obs}$ according to equation 2:

$$[AMC] = v_{ss}t + (v_0 - v_{ss})[1 - \exp(-k_{obs}t)]/k_{obs} \quad (2)$$

where [AMC] is the concentration of product formed over time t, $v_0$ is the initial reaction velocity and $v_{ss}$ is the final steady state rate. Values for $k_{obs}$ were then analyzed as a linear function of inhibitor concentration to generate an apparent second order rate constant ($k_{obs}$/inhibitor concentration or $k_{obs}/[I]$) describing the time-dependent inhibition. A complete discussion of this kinetic treatment has been fully described (Morrison et al., *Adv. Enzymol. Relat. Areas Mol. Biol.*, 1988, 61, 201).

Human Osteoclast Resorption Assay

Aliquots of osteoclastoma-derived cell suspensions were removed from liquid nitrogen storage, warmed rapidly at 37° C. and washed ×1 in RPMI-1640 medium by centrifugation (1000 rpm, 5 min at 4° C.). The medium was aspirated and replaced with murine anti-HLA-DR antibody, diluted 1:3 in RPMI-1640 medium, and incubated for 30 min on ice The cell suspension was mixed frequently.

The cells were washed ×2 with cold RPMI-1640 by centrifugation (1000 rpm, 5 min at 4° C.) and then transferred to a sterile 15 mL centrifuge tube. The number of mononuclear cells were enumerated in an improved Neubauer counting chamber.

Sufficient magnetic beads (5/mononuclear cell), coated with goat anti-mouse IgG, were removed from their stock bottle and placed into 5 mL of fresh medium (this washes away the toxic azide preservative). The medium was removed by immobilizing the beads on a magnet and is replaced with fresh medium.

The beads were mixed with the cells and the suspension was incubated for 30 min on ice. The suspension was mixed frequently. The bead-coated cells were immobilized on a magnet and the remaining cells (osteoclast-rich fraction) were decanted into a sterile 50 mL centrifuge tube. Fresh medium was added to the bead-coated cells to dislodge any trapped osteoclasts. This wash process was repeated ×10. The bead-coated cells were discarded.

The osteoclasts were enumerated in a counting chamber, using a large-bore disposable plastic pasteur pipette to charge the chamber with the sample. The cells were pelleted by centrifugation and the density of osteoclasts adjusted to 1.5× $10^4$/mL in EMEM medium, supplemented with 10% fetal calf serum and 1.7 g/litre of sodium bicarbonate. 3 mL aliquots of the cell suspension (per treatment) were decanted into 15 mL centrifuge tubes. These cells were pelleted by centrifugation. To each tube 3 mL of the appropriate treatment was added (diluted to 50 uM in the EMEM medium). Also included were appropriate vehicle controls, a positive control (87MEM1 diluted to 100 ug/mL) and an isotype control (IgG2a diluted to 100 ug/mL). The tubes were incubate at 37° C. for 30 min.

0.5 mL aliquots of the cells were seeded onto sterile dentine slices in a 48-well plate and incubated at 37° C. for 2 h. Each treatment was screened in quadruplicate. The slices were washed in six changes of warm PBS (10 mL/well in a 6-well plate) and then placed into fresh treatment or control and incubated at 37° C. for 48 h. The slices were then washed in phosphate buffered saline and fixed in 2% glutaraldehyde (in 0.2M sodium cacodylate) for 5 min., following which they were washed in water and incubated in buffer for 5 min at 37° C. The slices were then washed in cold water and incubated in cold acetate buffer/fast red garnet for 5 min at 4° C. Excess buffer was aspirated, and the slices were air dried following a wash in water.

The TRAP positive osteoclasts were enumerated by brightfield microscopy and were then removed from the surface of the dentine by sonication. Pit volumes were determined using the Nikon/Lasertec ILM21W confocal microscope.

General

Nuclear magnetic resonance spectra were recorded at either 250 or 400 MHz using, respectively, a Bruker AM 250 or Bruker AC 400 spectrometer. $CDCl_3$ is deuteriochloroform, DMSO-$d_6$ is hexadeuteriodimethylsulfoxide, and $CD_3OD$ is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (1R) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240 C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230400 mesh) silica gel.

Where indicated, certain of the materials were purchased from the Aldrich Chemical Co., Milwaukee, Wis., Chemical Dynamics Corp., South Plainfield, N.J., and Advanced Chemtech, Louisville, Ky.

EXAMPLES

In the following synthetic examples, temperature is in degrees Centigrade (° C.). Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

Example 1

5-Methoxy-benzofuran-2-carboxylic acid {(S)-3-methyl-1-[(4S,6S)-6-methyl-3-oxo-1-(pyridine-2-sulfonyl)-azepan-4-ylcarbamoyl]-butyl}-amide

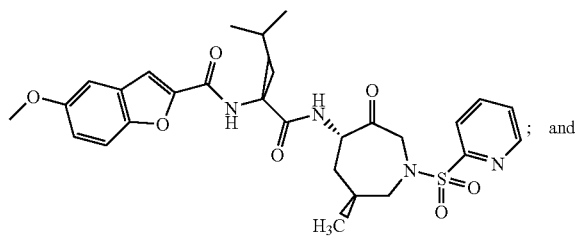

5-Methoxy-benzofuran-2-carboxylic acid {(S)-3-methyl-1-[(4R,6R)-6-methyl-3-oxo-1-(pyridine-2-sulfonyl)-azepan-4-ylcarbamoyl]-butyl}-amide

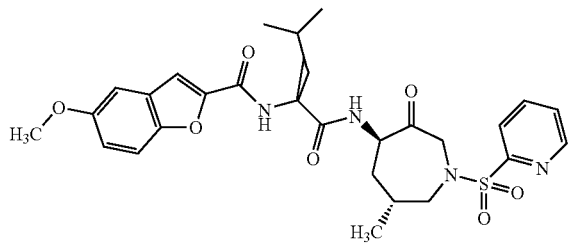

a. Allyl-(2-methyl-pent-4-enyl)-amine

To a solution of 2-methyl-pent-4-enoic acid ethyl ester (7.1 g, 50 mmol) was added dropwise a solution of DIBAL (1.0 M in hexanes, 75 ml) at −78 C over 1.0 h. After the addition, the reaction mixture was stirred at −78 C for another hour. The reaction was quenched with saturated NH4Cl (10 ml) and 4% HCl, then was extracted with EtOAc (3×100 ml). The combined organic extracts were dried with $MgSO_4$, filtered, concentrated by rotary evaporation and the crude reaction product was used in the next reaction without further purification. 2-Methyl-4-pentenal (3.3 g, 33.7 mmol) was dissolved in $CH_2Cl_2$ (100 ml). To this solution allylamine (2.9 g, 50.5 mmol) was added. Molecular sieves (5 g) were used to absorb water generated during the reaction. The mixture was stirred at room temperature over night. The reaction mixture was concentrated by rotary evaporation and the crude product was used in the next reaction without further purification. Allyl-(2-methyl-pent-4-enylidene)-amine (3.2 g, 23.4 mmol) was diluted in 50 ml MeOH. To the solution $NaBH_4$ (1.0 g, 26.3 mmol) was added at 0° C. After addition the mixture was stirred at RT for 5 h. The reaction mixture was concentrated and the residue was partitioned between EtOAc/20% aq. NaOH. The organic layer was dried over $Na_2SO_4$, fitered and concentrated by rotary evaporation to give allyl-(2-methyl-pent-4-enyl)-amine (1.5 g 48% yield): 1H-NMR (400 Hz, CDCl3): d=5.93-5.68 (m, 2H), 5.18-4.92(m, 4H), 3.21(d, 2H), 2.60-2.40(m, 2H), 1.97-1.65(m, 2H), 0.92(d, 3H)

b. Pyridine-2-sulfonic acid allyl-(2-methyl-pent-4-enyl)-amide

Allyl-(2-methyl-pent-4-enyl)-amine (1.0 g, 7.2 mmol) and NMM (1.7 g, 17.2 mmol) were mixed in 30 ml $CH_2Cl_2$.2-pyridinesulphonyl chloride (1.53 g, 8.6 mmol) was added slowly to the solution while it was cooled in an ice-water bath. After addition, the reaction mixture was stirred at RT overnight. The reaction mixture was washed with 10% $NaHCO_3$ and the brine, then was purified by column chromatography to give the title compound as a colorless oil (1.2 g, 60% yield): MS (M+H+) 281.2; 1H-NMR (400 Hz, CDCl3): d=8.70(d, 1H), 8.0-7.75(m, 2H), 7.5 (m, 1H) 5.80-5.60(m, 2H), 5.15-4.92(m, 4H), 4.00-3.90(m, 2H), 3.20-3.06(m, 2H), 2.15(m, 1H), 1.85(m, 2H), 0.89(d, 3H)

c. 3-methyl-1-(pyridine-2-sulfonyl)-2,3,4,7-tetrahydro-1H-azepine

Pyridine-2-sulfonic acid allyl-(2-methyl-pent-4-enyl)-amide (1.2 g, 4.3 mmol) was diluted in $CH_2Cl_2$ (100 ml). After carefully degass by Ar, Grubbs catalyst (0.35 g, 0.43 mmol) was added under Ar protection. The mixture was then refluxed for 2 h before the reaction mixture was concentrated by rotary evaporation. The product was purified by column chromatography (5%-20% EtOAc/hexanes) to give the title compound (0.9 g, 83% yield): MS (M+H+):253.2; 1H-NMR (400 Hz, CDCl3): d=8.70(d, 1H), 8.0-7.75(m, 2H), 7.5 (m, 1H) 5.79-5.60(m, 2H), 4.00(d, 2H), 3.65(dd, 1H), 3.22(dd, 1H), 2.30-2.05(m, 3H), 0.96(d, 3H)

d. 5-methyl-3-(pyridine-2-sulfonyl)-8-oxa-3-aza-bicyclo[5.1.0]octane

To the solution of 3-methyl-1-(pyridine-2-sulfonyl)-2,3,4,7-tetrahydro-1H-azepine (1.3 g, 5.16 mmol) in $CH_2Cl_2$ (50 ml) was added $NaHCO_3$ (1.3 g, 15.5 mmol) and then mCPBA (2.67 g, 15.5 mmol) in portions. Stirred at RT for 4 h before worked up by washing with 15% NaOH, saturated $K_2CO_3$ and brine. Dried over $Na_2SO_4$. The reaction mixture was concentrated by rotary evaporation and two insomers were seperated on column chromatography (30%-40% EtoAc/Hexane). The first elution (trans-isomer, 230 mg) was used in next steps, the second elution (cis-insomer 200 mg) was saved: MS (M+H+): 269.0; 1H-NMR (400 Hz, CDCl3): d=8.70(d, 1H), 8.0-7.75(m, 2H), 7.50 (m, 1H) 4.39(m, 1H), 3.92(m, 1H), 3.34-2.00(m, 6H), 1.40(m, 1H), 0.88(d, 3H)

e. 4-Azido-5-methyl-1-(pyridine-2-sulfonyl)-azepan-3-ol 5-methyl-3-(pyridine-2-sulfonyl)-8-oxa-3-aza-bicyclo[5.1.0]octane (230 mg, 0.86 mmol) was dissolved in the mixture of 8 ml MeOH and 2 ml $H_2O$. $NaN_3$ (170 mg, 2.6 mmol) and $NH_4Cl$ (140 mg, 2.6 mmol) were added to the solution. The resulting mixture was refluxed overnight. After the removal of MeOH, the residue was diluted in EtOAc and washed with 10% $NaHCO_3$ and brine. Purified on column chromatography gave the title compound (170 mg, yield 64%). MS (M+H+) 312.2; 1H-NMR (400 Hz, CDCl3): d=8.69(d, 1H), 8.04-7.94(m, 2H), 7.54 (m, 1H) 4.00-2.95 (m, 7H), 2.20(m, 1H), 1.90-1.74(m, 2H), 0.98(d, 3H)

f. 4-Amino-6-methyl-1-(pyridine-2-sulfonyl)-azepan-3-ol

4-Azido-6-methyl-1-(pyridine-2-sulfonyl)-azepan-3-ol (0.33 g, 1.06 mmol) was dissolved in THF (50 ml) and $H_2O$ (0.2 ml). $PPh_3$ (0.42 g, 1.59 mmol) was added to this solution. The reaction mixture was stirred at 45° C. over night. TLC showed no starting material left. THF was evaperated, azeotroped by toluene (2×100 ml). The resulting thick oil was dissolved in MeOH, treated with HCl in ether to adjust pH to acidic. More ether was added and the solution turned cloudy to give the title compound as a white precipitate (0.21 g, 71% yield) MS (M+H+) 286.0; 1H-NMR (400 Hz, CD3OD): d (ppm): 8.72(d, 1H), 8.14-7.99(m, 2H), 7.68(m, 1H), 3.85-3.69(m, 2H), 3.38-3.22(m, 3H), 3.10-3.04(m, 2H), 2.04(m, 1H), 1.82-1.66(m, 2H), 1.02(d, 3H)

g. {(S)-1-[3-Hydroxy-6-methyl-1-(pyridine-2-sulfonyl)-azepan-4-ylcarbamoyl]-3-methyl-butyl}-carbamic acid tert-butyl ester 4-Amino-6-methyl-1-(pyridine-2-sulfonyl)-azepan-3-ol HCl salt (0.21 g, 0.59 mmol) was dissolved in 5 ml DMF. To this solution, was added Boc-Leu-OH (0.22 g, 0.88 mmol) and HBTU (0.34 g, 0.90 mmol) and then NMM (0.24 g, 2.4 mmol). The mixture was stirred at RT overnight. DMF was removed under high vacuum. The residue was diluted in EtOAc and washed with H$_2$O, 10% NaHCO$_3$ and brine. Purification by column chromatography gave the title compound (0.2 g, 68% yield). MS (M+H+): 499.1; 1H-NMR (400 Hz, CDCl3): 8.75(d, 1H), 8.0-7.75(m, 2H), 7.5 5(m, 1H) 5.10(m, 1H), 4.15-2.90(m, 10H), 2.10-1.48(m, 14H), 1.00(m, 9H)

h. 5-Methoxy-benzofuran-2-carboxylic acid {(S)-1-[3-hydroxy-6-methyl-1-(pyridine-2-sulfonyl)-azepan-4-ylcarbamoyl]-3-methyl-butyl}-amide To {(S)-1-[3-hydroxy-6-methyl-1-(pyridine-2-sulfonyl)-azepan-4-ylcarbamoyl]-3-methyl-butyl}-carbamic acid tert-butyl ester (0.13 g, 0.28 mmol) was added HCl/dioxane (4M, 2.8 ml, 11.2 mmol). The mixture was stirred at RT for 2 h before solvents and excess amount of HCl was removed on rotavapor. The result white solid was dissolved in 5 ml DMF. To the solution was added 5-methoxy-benzofuran-2-carboxylic acid (63.4 mg, 0.33 mmol), HBTU (125 g, 0.33 mmol) and NMM (0.14 g, 1.34 mmol). The mixture was stirred at RT overnight. DMF was then removed and the residue was re-dissolved in EtOAc (50 ml), washed with 10% NaHCO$_3$ (50 ml×2) and brine (50 ml). The combined organics were concentrated by rotary evaporation. Purification by column chromatograghy gave the title compound (110 mg in 69% yield, 2 steps): MS (M+H+):573.4; 1H-NMR (400 Hz, CDCl3): d=8.74-8.66(dd, 1H), 7.96-6.97(m, 9H), 4.72(m, 1H), 4.18-3.21(m, 7H), 2.81(m, 1H), 2.04-1.74(m, 6H), 1.25 (m, 2H), 0.99-0.87(m, 9H)

i. 5-Methoxy-benzofuran-2-carboxylic acid {(S)-3-methyl-1-[(4S,6S)-6-methyl-3-oxo-1-(pyridine-2-sulfonyl)-azepan-4-ylcarbamoyl]-butyl}-amide and 5-methoxy-benzofuran-2-carboxylic acid {(S)-3-methyl-1-[(4R,6R)-6-methyl-3-oxo-1-(pyridine-2-sulfonyl)-azepan-4-ylcarbamoyl]-butyl}-amide To a solution of 5-methoxy-benzofuran-2-carboxylic acid {(S)-1-[3-hydroxy-6-methyl-1-(pyridine-2-sulfonyl)-azepan-4-ylcarbamoyl]-3-methyl-butyl}-amide (110 mg, 0.19 mmol) in 5 ml CH$_2$Cl$_2$, was added Dess-Martin reagent (122 mg, 0.29 mmol) at RT. The solution was stirred for 2 h when 50 ml CH$_2$Cl$_2$ was added and then washed with 10% NaHCO$_3$ and brine. Purification by column chromatograghy (50% ethyl acetate in hexane) gave the title compound (90 mg, 82% yield). 1H-NMR (400 Hz, CDCl3): d (ppm): 8.69(d, 1H), 7.94(m, 2H), 7.39-7.24(m, 3H), 7.02(m, 4H), 5.26(m, 1H), 4.69(m, 2H), 3.84(m, 4H), 3.00(m, 1H), 2.05(m, 1H), 1.73(m, 2H), 1.61(m, 4H), 1.18(d, 3H), 0.97(d,6H);). The diastereomers were separated by HPLC. Diastereomer 1: MS (M+H+): 571.2; Diastereomer 2: MS (M+H+): 571.2

Example 2

Benzo[b]thiophene-2-carboxylic acid {(S)-1-[(4S,6S)-6-methyl-3-oxo-1-(pyridine-2-sulfonyl)-azepan-4-ylcarbamoyl]-3-methyl-butyl}-amide

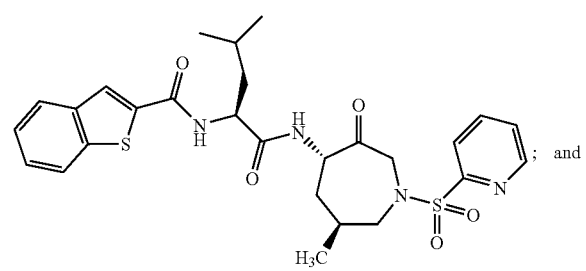

; and benzo[b]thiophene-2-carboxylic acid {(S)-1-[(4R,6R)-6-methyl-3-oxo-1-(pyridine-2-sulfonyl)-azepan-4-ylcarbamoyl]-3-methyl-butyl}-amide

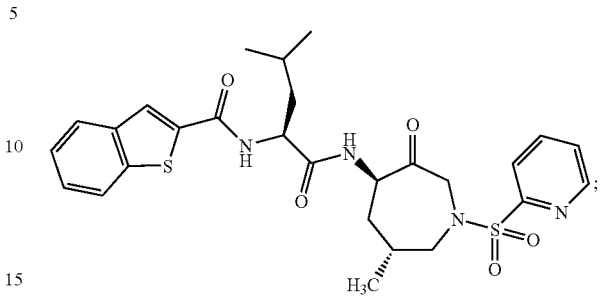

Following the procedure of Example 1 (a-i), except substituting "benzo[b]thiophene-2-carboxylic acid" for "5-methoxy-benzofuran-2-carboxylic acid" gave the title compound: MS (M+H+); 1H-NMR (400 Hz, CDCl3): d (ppm): 8.69(d, 1H), 7.97-7.78(m, 5H), 7.41-7.39(m, 3H), 6.95(d, 1H), 6.65 (d, 1H), 5.25(m, 1H), 4.71-4.60(m, 2H), 3.86(d, 1H), 3.80(m, 1H), 2.98(d, 1H), 2.05(m, 2H), 1.75-1.55(m, 4H), 1.18(d, 3H), 0.97(d, 6H); The diastereomers were separated by HPLC. Diastereomer 1: MS (M+H+): 557.2; Diastereomer 2: MS (M+H+): 557.2

Example 3

3-Methyl-benzofuran-2-carboxylic acid {(S)-1-[(4S,6S)-6-methyl-3-oxo-1-(pyridine-2-sulfonyl)-azepan-4-ylcarbamoyl]-3-methyl-butyl}-amide

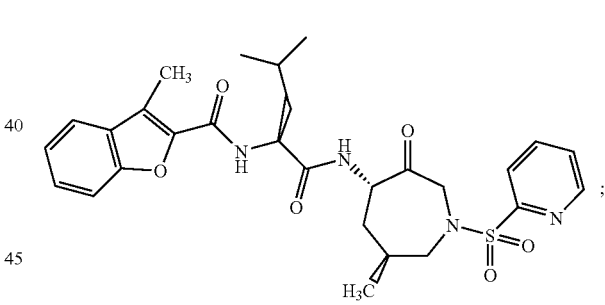

; and 3-methyl-benzofuran-2-carboxylic acid {(S)-1-[(4R,6R)-6-methyl-3-oxo-1-(pyridine-2-sulfonyl)-azepan-4-ylcarbamoyl]-3-methyl-butyl}-amide

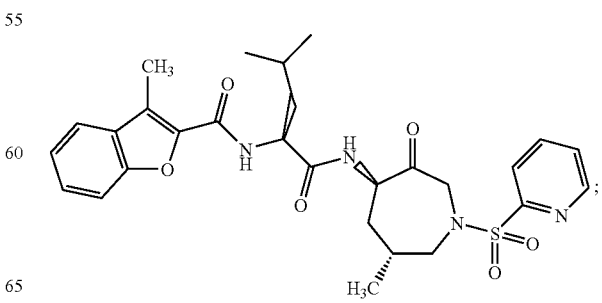

Following the procedure of Example 1 (a-i), except substituting "3-methyl-benzofuran-2-carboxylic acid" for "5-methoxy-benzofuran-2-carboxylic acid" gave the title compound: MS (M+H+) 555.2; 1H-NMR (400 Hz, CDCl3): d (ppm): 8.68(d, 1H), 7.93(m, 2H), 7.59-7.27(m, 5H), 7.03-6.96(dd, 2H), 5.26(m, 1H), 4.70-4.61(m, 1H), 3.82(d, 1H), 3.76(m, 1H), 2.99(d, 1H), 2.60(s, 3H), 2.05(m, 2H), 1.76-1.58(m, 5H), 1.19(d, 3H), 0.97(d, 6H); The diastereomers were separated by HPLC. Diastereomer 1: MS (M+H+): 555.2; Diastereomer 2: MS (M+H+): 555.4

Example 4

Thieno[3,2-b]thiophene-2-carboxylic acid ((S)-1-[(4S,6S)-6-methyl-3-oxo-1-(pyridine-2-sulfonyl)-azepan-4-ylcarbamoyl]-3-methyl-butyl}-amide

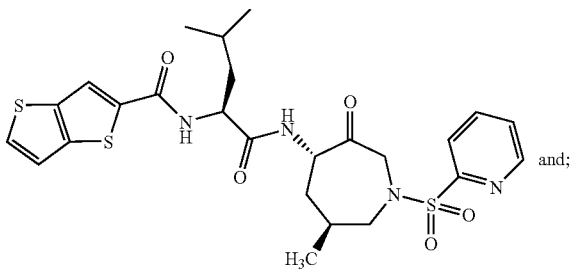

thieno[3,2-b]thiophene-2-carboxylic acid {(S)-1-[(4R,6R)-6-methyl-3-oxo-1-(pyridine-2-sulfonyl)-azepan-4-ylcarbamoyl]-3-methyl-butyl}-amide

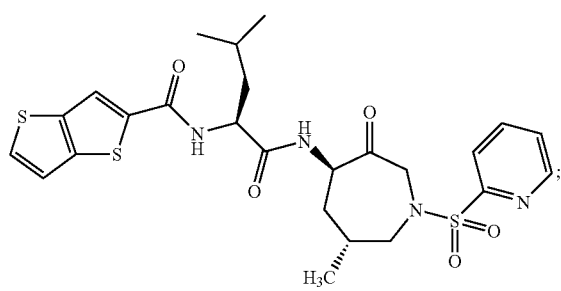

Following the procedure of Example 1 (a-i), except substituting "thieno[3,2-b]thiophene-2-carboxylic acid" for "5-methoxy-benzofuran-2-carboxylic acid" gave the title compound: MS (M+H+) 563.2; 1H-NMR (400 Hz, CDCl3): d (ppm): 8.69(d, 1H), 7.97-7.78(m, 5H), 7.41-7.38(m, 3H), 6.95(d, 1H), 6.65(d, 1H), 5.26(m, 1H), 4.69-4.60(m, 2H), 3.85(d, 1H), 3.80(m, 1H), 2.99(d, 1H), 2.04(m, 2H), 1.75-1.55(m, 4H), 1.18(d, 3H), 0.97(d, 6H); The diastereomers were separated by HPLC. Diastereomer 1: MS (M+H+): 563.2; Diastereomer 2:
MS (M+H+): 563.2

Example 5

Benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide

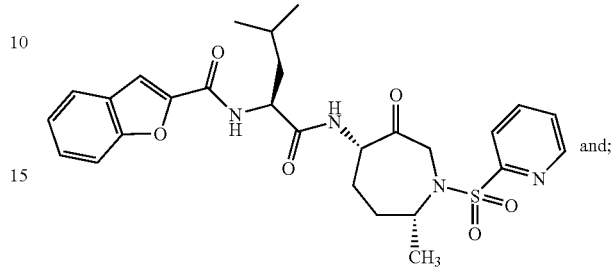

benzofuran-2-carboxylic acid {(S)-3-methyl-1-[(4R,7S)-7-methyl-3-oxo-1-(pyridine-2-sulfonyl)-azepan-4-ylcarbamoyl]-butyl}-amide

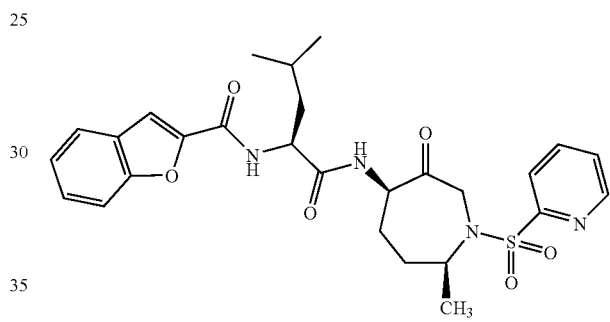

a. Allyl-(1-methyl-pent-4-enylidene)-amine Allyl-(1-methyl-pent-4-enyl)-amine

Hex-5-en-2-one (9.8 g, 11.6 ml, 100 mmol) was added to a stirred solution of allylamine (8.55 mmol, 11.25 ml, 150 mmol), 4 Angstrom molecular sieves (52 g), and p-toluene sulfonic acid (10 mg) in CH$_2$Cl$_2$ (200 ml) and was stirred overnight. The reaction mixture was concentrated in vacuo by rotary evaporation and was used in the next reaction without further purification (13 g, 95%). Electrospray mass spec: M+H$^+$=137.9 b. Racemic Allyl-(1-methyl-pent-4-enyl)-amine

Sodium borohydride (2.7 g, 71 mmol) was added portionwise to a stirred solution of allyl-(1-methyl-pent-4-enylidene)-amine (6.5 g, 47 mmol) in MeOH (100 ml) at 0 C. The reaction mixture was stirred for 30 minutes, then warmed to RT. Approximately 90 ml of MeOH was removed from the reaction mixture by rotary evaporation, then the reaction mixture was diluted with ether (200 ml), then extracted with water then brine. The combined organics were dried with MgSO$_4$, filtered, concentrated in vacuo by rotary evaporation to give a pale yellow liquid that was used in the next reaction without further purification (5.2 g, 80%).

c. Racemic Allyl-(1-methyl-pent-4-enyl)-carbamic acid benzyl ester

Carbobenzyloxy chloride (9.56 g, 8 ml) was added dropwise to a stirred solution of allyl-(1-methyl-pent-4-enyl)-amine (7 g, 50 mmol), triethylamine (5.5 g, 8.0 ml, 57.5 mmol) in CH$_2$Cl$_2$ (100 ml) at 0 C. The reaction mixture was warmed to RT, then was stirred for 2 h. The reaction mixture was diluted with CH$_2$Cl$_2$ (100 ml), then was extracted with water, then brine. The combined organics were dried with MgSO$_4$, filtered, concentrated in vacuo by rotary evaporation, then was chromatographed (silica gel, 4% EtOAc/hexanes) to give the title compound (8.9 g, 65% yield): Liquid Chromatgraphy/Electrospray mass spec: M+H$^+$=274.2 d. Racemic 2-Methyl-2,3,4,7-tetrahydro-azepine-1-carboxylic acid benzyl ester

Allyl-(1-methyl-pent-4-enyl)-carbamic acid benzyl ester (1.036 g, 3.8 mmol) was dissolved in CH$_2$Cl$_2$ (10 ml) and a stream of argon gas was bubbled into the reaction mixture for 10 minutes. Then bis(tricyclohexylphosphine)benzylidine ruthenium(IV) dichloride (Strem Chemicals, Grubbs' catalyst, 22 mg, 0.027 mmol) was added and the reaction mixture was refluxed for 2 h. Additional bis(tricyclohexylphosphine) benzylidine ruthenium(IV) dichloride (11 mg, 0.014 mmol) was added and the reaction mixtrue was refluxed for an additional 1.5 hours. The reaction was cooled to RT under argon overnight, then was concentrated in vacuo by rotary evaporation, then was chromatographed (silica gel, 5% EtOAc/hexanes) to give the title compound (0.83 g, 89%): 1H NMR: 7.35-7.20 (m, 5H), 5.65 (1H, m), 5.13 (2H, AB), 4.45-4.05 (m, 2H), 3.56 (1H, d), 2.25-2.10 (m, 2H), 1.90-1.60 (m, 2H), 1.12 (3H, d); Liquid Chromatgraphy/Electrospray mass spec: M+H$^+$=246.2.

e. Racemic (1S,4R,7R)-4-Methyl-8-oxa-3-aza-bicyclo[5.1.0]octane-3-carboxylic acid benzyl ester m-Chloro-perbenzoic acid (1.05 g, 57-86% pure) was added to a solution of 2-methyl-2,3,4,7-tetrahydro-azepine-1-carboxylic acid benzyl ester (0.83 g, 3.34 mmol) in CH$_2$Cl$_2$ at 0 degrees C. The reaction mixture was stirred for half an hour, then was warmed to RT. Additional m-chloro-perbenzoic acid (0.3 g, 57-86% pure) was added and the reaction was stirred 2 h. The reaction mixture was concentrated in vacuo by rotary evaporation, then 80 ml of 9:1 hexanes/EtOAc was added and the reaction mixture was filtered. The filtrate was concentrated in vacuo by rotary evaporation, then was chromatographed (silica gel, 20% EtOAc:hexanes) to give racemic (1S,4R,7S)-4-methyl-8-oxa-3-aza-bicyclo[5.1.0]octane-3-carboxylic acid benzyl ester (0.44 g, 50%) and the title compound as a racemic mixture of the title compound (0.15 g, 17% yield): 1H NMR: 7.42-7.22 (m, 5H), 5.13 (2H, s), 4.50-4.15 (m, 2H), 3.27 (1H, d), 3.12-2.95 (1H, m), 2.15-1.70 (m, 2H), 1.47 (m, 2H), 1.12 (3H, d); Liquid Chromatgraphy/Electrospray mass spec: M+H$^+$=262.0.

f. Racemic (2R,5S,6S)-5-Azido-6-hydroxy-2-methyl-azepane-1-carboxylic acid benzyl ester Sodium azide (0.56 g, 8.62 mmol) was added to a solution of racemic (1S,4R,7R)-4-methyl-8-oxa-3-aza-bicyclo[5.1.0]octane-3-carboxylic acid benzyl ester (0.75 g, 2.87 mmol) and ammonium chloride (0.46 g, 8.62 mmol) in MeOH (5 ml) and H$_2$O (0.5 ml), then was refluxed for 6 h. The reaction mixture was concentrated in vacuo by rotary evaporation, then was diluted with water (5 ml) and extracted with EtOAc (10 ml). The organic layer was then extracted with water, brine, dried with MgSO$_4$, filtered, concentrated in vacuo by rotary evaporation, and chromatographed (silica gel, 20% EtOAc/hexanes) to yield the title compound (0.7 g, 80%): 7.39-7.30 (m, 5H), 5.15 (2H, s), 4.10-3.67 (m, 2H), 3.10 (1H, d), 1.85-1.53 (m, 4H), 1.09 (3H, d); Liquid Chromatgraphy/Electrospray mass spec: M+H$^+$=305.2.

g. Racemic (2R,5S,6S)-5-Amino-6-hydroxy-2-methyl-azepane-1-carboxylic acid benzyl ester Triphenylphosphine (1.94 g, 7.4 mmol) was added to a solution of racemic (2R,5S,6S)-5-azido-6-hydroxy-2-methyl-azepane-1-carboxylic acid benzyl ester (1.5 g, 4.93 mmol) in THF (185 ml) and H$_2$O (0.7 ml), then was heated to 45 degrees C. overnight. The reaction mixture was then diluted with toluene (100 ml×2) and was azeotroped in vacuo by rotary evaporation twice. The resxulting oil was dissolved in MeOH and HCl in Et$_2$O and the resulting salt was collected following filtration and was used in the next reaction without further purification (1.4 g, 90%).

h. (2R,5S,6S)-5-((S)-2-tert-Butoxycarbonylamino-4-methyl-pentanoylamino)-6-hydroxy-2-methyl-azepane-1-carboxylic acid benzyl ester and (2S,5R,6R)-5-((S)-2-tert-Butoxycarbonylamino-4-methyl-pentanoylamino)-6-hydroxy-2-methyl-azepane-1-carboxylic acid benzyl ester 1-(3-Dimethylaminopropyl)-3-ethylcarbodiimide (0.33 g, 1.73 mmol) was added to a solution of Boc-leucine-hydrate (0.43 g, 1.7 mmol), diisopropylethylamine (0.22 g, 0.3 ml, 1.7 mmol), hydroxybenztriazole (0.25 g, 1.85 mmol), and racemic (2R,5S,6S)-5-Amino-6-hydroxy-2-methyl-azepane-1-carboxylic acid benzyl ester (0.5 g, 1.6 mmol) in DMF (10 ml). The reaction was stirred overnight at RT, then was diluted with EtOAc (100 ml), washed with H$_2$O (3×50 ml), brine (50 ml), dried with magnesium sulfate, filtered, concentrated in vacuo by rotary evaporation, and chromatographed (silica gel, 50% EtOAc/hexanes) to yield the title compound (0.78 g, 100%): 1H NMR: 7.40-7.29 (m, 5H), 6.75 (1H, bd), 5.12 (2H, AB), 5.0 (1H, bs), 4.15-3.72 (m, 2H), 3.06 (1H, d), 1.60-1.30 (m, 2H), 1.60-1.30 (m, 5H), 1.12 (3H, d), 0.97-0.87(6H, dd); Electrospray mass spec: M+H$^+$=492.0 i. [(S)-1-((3S,4S,7R)-3-Hydroxy-7-methyl-azepan-4-ylcarbamoyl)-3-methyl-butyl]-carbamic acid tert-butyl ester and [(S)-1-((3R,4R,7S)-3-Hydroxy-7-methyl-azepan-4-ylcarbamoyl)-3-methyl-butyl]-carbamic acid tert-butyl ester (2R,5S,6S)-5-((S)-2-tert-Butoxycarbonylamino-4-methyl-pentanoylamino)-6-hydroxy-2-methyl-azepane-1-carboxylic acid benzyl ester and (2S,5R,6R)-5-((S)-2-tert-butoxycarbonylamino-4-methyl-pentanoylamino)-6-hydroxy-2-methyl-azepane-1-carboxylic acid benzyl ester (0.77 g, 1.57 mmol) was dissolved in EtOAc (27.5 ml), MeOH (5.5 ml). Then 10% Pd/C (0.39 g) was added and the reaction was stirred overnight under a balloon filled with hydrogen gas. The reaction mixture was filtered through Celite, concentrated in vacuo by rotary evaporation and was used in the next reaction without further purification (0.56 g): Electrospray mass spec: M+H$^+$=358.11.

j. [(S)-1-((3S,4S,7R)-1-Benzenesulfonyl-3-hydroxy-7-methyl-azepan-4-ylcarbamoyl)-3-methyl-butyl]-carbamic acid tert-butyl ester and [(S)-1-((3R,4R,7S)-1-Benzenesulfonyl-3-hydroxy-7-methyl-azepan-4-ylcarbamoyl)-3-methyl-butyl]-carbamic acid tert-butyl ester 2-Pyridine sulfonyl chloride (0.6 g, 3.4 mmol) was added to a solution of [(S)-1-((3S,4S,7R)-3-Hydroxy-7-methyl-azepan-4-ylcarbamoyl)-3-methyl-butyl]-carbamic acid tert-butyl ester and [(S)-1-((3R,4R,7S)-3-hydroxy-7-methyl-azepan-4-ylcarbamoyl)-3-methyl-butyl]-carbamic acid tert-butyl ester (1.0 g, 2.8 mmol), N-methyl morpholine (0.45 ml, 4.1 mmol) in CH$_2$Cl$_2$ (35 ml) and was stirred at RT overnight. The reaction mixture was diluted with EtOAc (100 ml), washed with H$_2$O, brine, dried with magnesium sulfate, filtered, concentrated in vacuo by rotary evaporation, and chromatographed (silica gel, 2.5% MeOH/CH$_2$Cl$_2$) to yield the title compound (0.9 g, 64%): 1H NMR: 8.68 (m, 1H), 8.05

(1H, d), 7.92 (1H, dd), 7.50 (1H, dd), 6.66 (1H, bd), 4.95-4.88 (dd), 4.20-3.87 (m, 3H), 3.65 (1H, bs), 3.40 (1H, d), 1.94-1.57 (m, 4H), 1.45-1.38 (m, 6H), 1.14 (3H, dd), 0.94 (6H, dd); Electrospray mass spec: M+H⁺=499.0 k. (S)-2-Amino-4-methyl-pentanoic acid ((3S,4S,7R)-1-(2-pyridine)-sulfonyl-3-hydroxy-7-methyl-azepan-4-yl)-amide and (S)-2-Amino-4-methyl-pentanoic acid ((3R,4R,7S)-1-(2-pyridine)-sulfonyl-3-hydroxy-7-methyl-azepan-4-yl)-amide HCl in dioxane (4.0 M, 15 ml) was added to a stirred solution of [(S)-1-((3S,4S,7R)-1-benzenesulfonyl-3-hydroxy-7-methyl-azepan-4-ylcarbamoyl)-3-methyl-butyl]-carbamic acid tert-butyl ester and [(S)-1-((3R,4R,7S)-1-benzenesulfonyl-3-hydroxy-7-methyl-azepan-4-ylcarbamoyl)-3-methyl-butyl]-carbamic acid tert-butyl ester (0.9 g, 1.8 mmol) in MeOH (15 ml). The reaction mixture was stirred for 2 h at RT, then was concentrated in vacuo by rotary evaporation and was used in the next reaction without further purification (0.85 g).

l. Benzofuran-2-carboxylic acid {(S)-1-[(3S,4S,7R)-3-hydroxy-7-methyl-1-(pyridine-2-sulfonyl)-azepan-4-ylcarbamoyl]-3-methyl-butyl}-amide and benzofuran-2-carboxylic acid {(S)-1-[(3R,4R,7S)-3-hydroxy-7-methyl-1-(pyridine-2-sulfonyl)-azepan-4-ylcarbamoyl]-3-methyl-butyl}-amide 1-(3-Dimethylaminopropyl)-3-ethylcarbodiimide (0.35 g, 1.85 mmol) was added to a solution of 2-benzofuran-carboxylic acid (0.3 g, 1.85 mmol), (S)-2-amino-4-methyl-pentanoic acid ((3S,4S,7R)-1-(2-pyridine)-sulfonyl-3-hydroxy-7-methyl-azepan-4-yl)-amide and (S)-2-amino-4methyl-pentanoic acid ((3R,4R,7S)-1-(2-pyridine)-sulfonyl-3-hydroxy-7-methyl-azepan-4-yl)-amide (0.85 g, 1.8 mmol), diisopropylethylamine (0.48 g, 0.65 ml, 3.7 mmol), hydroxybenztriazole (0.25 g, 1.85 mmol) in DMF (10 ml) and was stirred at RT overnight. The reaction mixture was then warmed to RT and was stirred overnight. The reaction mixture was diluted with EtOAc (100 ml), washed with H₂O, brine, dried with magnesium sulfate, filtered, concentrated in vacuo by rotary evaporation, and chromatographed (silica gel, 2.5% MeOH/CH₂Cl₂) to yield the title compound (0.8 g, 82%): 1H NMR: 8.65 (m, 1H), 8.05 (m, 1H), 7.87 (dd, 1H), 7.62 (dd, 1H), 7.50-7.35 (m, 3H), 7.28-7.20 (m, 1H), 7.07 (m, 1H), 6.92 (1H, bd), 6.80 (bd, 1H), 4.65-4.48 (m, 1H), 4.20-3.87 (m, 3H), 3.65 (1H, bd), 3.40 (1H, dd), 1.94-1.57 (m, 4H), 1.45-1.38 (m, 6H), 1.14 (3H, dd), 0.94 (6H, m); Electrospray mass spec: M+H⁺=542.98 m. Benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide and Benzofuran-2-carboxylic acid {(S)-3-methyl-1-[(4R,7S)-7-methyl-3-oxo-1-(pyridine-2-sulfonyl)-azepan-4-ylcarbamoyl]-butyl}-amide Dess-Martin periodinane (1.0 g, 2.36 mmol) was added to a solution of benzofuran-2-carboxylic acid {(S)-1-[(3S,4S,7R)-3-hydroxy-7-methyl-1-(pyridine-2-sulfonyl)-azepan-4-ylcarbamoyl]-3-methyl-butyl}-amide and benzofuran-2-carboxylic acid {(S)-1-[(3R,4R,7S)-3-hydroxy-7-methyl-1-(pyridine-2-sulfonyl)-azepan-4-ylcarbamoyl]-3-methyl-butyl}-amide (0.8 g, 1.48 mmol) in CH₂Cl₂ (20 ml) and was stirred at RT for 45 minutes. The solution was washed with 10% NaHCO₃ and brine. Purification by column chromatography (60% ethyl acetate/hexanes) gave the title compound as a mixture of diasteromers (0.75 g, 94%); The diastereomers were separated by HPLC. Diastereomer 1:1H NMR: 8.72 (m, 1H), 8.0 (d, 1H), 8.92 (dd, 1H), 7.65 (d, 1H), 7.56 (d, 1H), 7.45 (s, 1H), 7.42 (dd, 2H), 7.28 (d, 1H), 7.10 (d, 1H), 5.15 (m, 1H), 4.77 (d, 1H), 4.68 (m, 1H), 4.40 (m, 1H), 3.86 (d, 1H), 2.20-2.08 (m, 2H), 1.78-1.50 (m, 5H), 1.22 (dd, 3H), 0.98 (m, 6H); Electrospray mass spec: M+H⁺=541.2; Diastereomer 2:1H NMR: 8.68 (m, 1H), 8.04 (d, 1H), 8.92 (dd, 1H), 7.68 (d, 1H), 7.58 (d, 2H), 7.52 (s, 1H), 7.42 (dd, 1H), 7.29 (d, 1H), 7.05 (m, 2H), 5.12 (m, 1H), 4.75-4.68 (m, 1H), 4.43 (m, 1H), 3.83 (d, 1H), 2.25-2.12 (m, 2H), 1.88-1.50 (m, 5H), 0.98 (m, 9H); Electrospray mass spec: M+H⁺=541.2

Example 6

Preparation of Single Diasteromer

Benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide

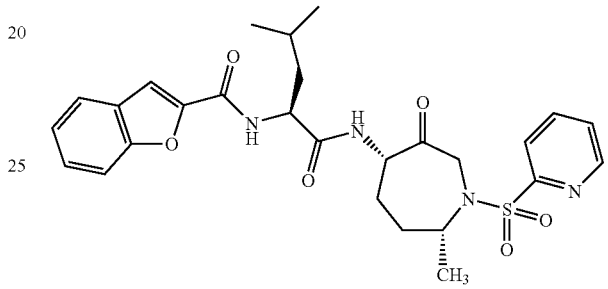

a. ((R)-2-Iodo-1-methyl-ethyl)-carbamic acid benzyl ester

Triphenylphospine (24 g, 91.8 mmol) was added to a solution of imidazole (12.5 g, 184 mmol) in CH₂Cl₂ (231 ml), then was cooled to 0 degrees C. Iodine (23.3 g, 91.8 mmol) was added to the suspension. The reaction mixture turned yellow, then faintly brown. After 5 minutes ((R)-2-hydroxy-1-methyl-ethyl)-carbamic acid benzyl ester (9.59 g, 45.9 mmol) was added and the reaction mixture was warmed to RT then stirred for 3 h. Then, H₂O (7 ml) was added and the reaction mixture was partitioned between CH₂Cl₂ (300 ml) and H₂O (600 ml). The aqueous layer was extracted again with CH₂Cl₂ (200 ml). The combined organic layer was then washed with a solution of 1:9 aq. saturated Na₂S₂O₃: H₂O (140 ml), then brine (400 ml). The combined organics were dried with MgSO₄, filtered, concentrated in vacuo, then filtered through a plug of silica gel washing with 15% EtOAc/hexanes (1.5 liter). The solution was concentrated in vacuo, then the solid was washed with hexane and the resultant white solid was used in the next reaction without further purification (11 g, 75%).

b. ((R)-1-Methyl-pent-4-enyl)-carbamic acid benzyl ester

Copper (I) bromide-dimethyl sulfide (1.93 g, 9.4 mmol) was dissolved in distilled THF (24 ml), then was cooled to −78 degrees C. A solution of allyl magnesium chloride (9.4 ml, 2M in THF, Aldrich) was added dropwise, then the solution was stirred for 30 minutes. ((R)-2-Iodo-1-methyl-ethyl)-carbamic acid benzyl ester (1.5 g, 4.7 mmol) in distilled THF (3 ml) was added dropwise, then the reaction was warmed to −40 degrees C. and was stirred for 2.5 h. The reaction mixture was quenched with aq. sat. NH₄Cl (4 ml) at −40 degrees C., warmed to RT and the gray reaction mixture turned sky blue. THF was removed in vacuo. Then, Et₂O was added and the reaction mixture was filtered to remove precipitated solids. The solids were washed with additional Et₂O. The combined organics were extracted with 10% NH₄OH (3×), then brine.

The combined organics were dried with MgSO₄, filtered, concentrated in vacuo, then filtered through a plug of silica gel washing with 20% EtOAc/hexanes (100 ml). The solution was concentrated in vacuo, then the resultant colorless oil was used in the next reaction without further purification (0.8 g, 73%).

c. Allyl-((R)-1-methyl-pent-4-enyl)-carbamic acid benzyl ester ((R)-1-Methyl-pent-4-enyl)-carbamic acid benzyl ester (790 mg, 3.39 mmol) was dissolved in DMF (8 ml) and was cooled to 0 degrees C. Sodium hydride (60% dispersion, 271 mg, 6.78 mmol) was added and the reaction was stirred for 15 minutes. Allyl bromide (1.23 g, 0.88 ml, 10.17 mmol) was added and the reaction mixture was stirred for 3 h at 0 degrees C. H₂O (10 ml) was added, then 2N HCl was added dropwise adjusting the pH to 1. The reaction mixture was extracted with Et₂O (2×50 ml). The combined organics were washed with aq. 2N HCl, then aq. NaHCO₃, then brine. The combined organics were dried with MgSO₄, filtered, concentrated in vacuo, then chromatographed on silica gel (5% EtOAc/hexanes) to yield the title compound as a colorless oil (883 mg, 95%).

d. 2-Methyl-2,3,4,7-tetrahydro-azepine-1-carboxylic acid benzyl ester

Allyl-(1-methyl-pent-4-enyl)-carbamic acid benzyl ester (0.872 g, 3.19 mmol) was dissolved in CH₂Cl₂ (10 ml) and a stream of argon gas was bubbled into the reaction mixture for 10 minutes. Then bis(tricyclohexylphosphine)benzylidine ruthenium(IV) dichloride (Strem Chemicals, Grubbs' catalyst, 19 mg, 0.0227 mmol) was added and the reaction mixture was refluxed for 2 h. Additional bis(tricyclohexylphosphine)benzylidine ruthenium(IV) dichloride (mg, 0.0108 mmol) was added and the reaction mixture was refluxed for an additional 1.5 hours. The reaction was cooled to RT under argon overnight, then was concentrated in vacuo by rotary evaporation, then was chromatographed (silica gel, 5% EtOAc/hexanes) to give the title compound (0.72 g, 92%): 1H NMR: 7.35-7.20 (m, 5H), 5.65 (1H, m), 5.13 (2H, AB), 4.45-4.05 (m, 2H), 3.56 (1H, d), 2.25-2.10 (m, 2H), 1.90-1.60 (m, 2H), 1.12 (3H, d); Liquid Chromatgraphy/Electrospray mass spec: M+H⁺=246.2.

e. (1S,4R,7R)-4-Methyl-8-oxa-3-aza-bicyclo[5.1.0]octane-3-carboxylic acid benzyl ester m-Chloro-perbenzoic acid (1.10 g, 57-86% pure) was added to a solution of 2-methyl-2,3,4,7-tetrahydro-azepine-1-carboxylic acid benzyl ester (0.72 g, 2.94 mmol) in CH₂Cl₂ at 0 degrees C. The reaction mixture was stirred for half an hour, then was warmed to RT. Additional m-chloro-perbenzoic acid (0.660 g, 57-86% pure) was added and the reaction was stirred 2 h. The reaction mixture was concentrated in vacuo by rotary evaporation, then 80 ml of 9:1 hexanes/EtOAc was added and the reaction mixture was filtered. The filtrate was concentrated in vacuo by rotary evaporation, then was chromatographed (silica gel, 20% EtOAc:hexanes) to give (1S,4R,7S)₄-methyl-8-oxa-3-aza-bicyclo[5.1.0]octane-3-carboxylic acid benzyl ester (0.450 g, 75%) and the title compound (0.15 g, 25% yield): 1H NMR: 7.42-7.22 (m, 5H), 5.13 (2H, s), 4.50-4.15 (m, 2H), 3.27 (1H, d), 3.12-2.95 (1H, m), 2.15-1.70 (m, 2H), 1.47 (m, 2H), 1.12 (3H, d); Liquid Chromatgraphy/Electrospray mass spec: M+H⁺=262.0.

f. (2R,5S,6S)-5-Azido-6-hydroxy-2-methyl-azepane-1-carboxylic acid benzyl ester

Sodium azide (0.139 g, 2.14 mmol) was added to a solution of (1S,4R,7R)-4-methyl-8-oxa-3-aza-bicyclo[5.1.0]octane-3-carboxylic acid benzyl ester (0.186 g, 0.71 mmol) and ammonium chloride (0.114 g, 2.14 mmol) in MeOH (1.5 ml) and H₂O (0.15 ml), then was refluxed for 6 h. The reaction mixture was concentrated in vacuo by rotary evaporation, then was diluted with water (5 ml) and extracted with EtOAc (10 ml). The organic layer was then extracted with water, brine, dried with MgSO₄, filtered, concentrated in vacuo by rotary evaporation, and chromatographed (silica gel, 20% EtOAc/hexanes) to yield the title compound (0.192 g, 89%): 7.39-7.30 (m, 5H), 5.15 (2H, s), 4.10-3.67 (m, 2H), 3.10 (1H, d), 1.85-1.53 (m, 4H), 1.09 (3H, d); Liquid Chromatgraphy/Electrospray mass spec: M+H⁺=305.2.

g. (2R,5S,6S)-5-Amino-6-hydroxy-2-methyl-azepane-1-carboxylic acid benzyl ester

Triphenylphosphine (0.25 g, 0.952 mmol) was added to a solution of (2R,5S,6S)-5-azido-6-hydroxy-2-methyl-azepane-1-carboxylic acid benzyl ester (0.193 g, 0.635 mmol) in THF (10 ml) and H₂O (0.04 ml), then was heated to 45 degrees C. overnight. The reaction mixture was then diluted with toluene (100 ml×2) and was azeotroped in vacuo by rotary evaporation twice. The resulting oil was dissolved in MeOH and HCl in Et₂O and the resulting salt was collected following filtration and was used in the next reaction without further purification (0.27 g, 90%).

h. (2R,5S,6S)-5-((S)-2-tert-Butoxycarbonylamino-4-methyl-pentanoylamino)-6-hydroxy-2-methyl-azepane-1-carboxylic acid benzyl ester 1-(3-Dimethylaminopropyl)-3-ethylcarbodiimide (0.164 g, 0.22 mmol) was added to a solution of Boc-Leucine-hydrate (0.190 g, 0.76 mmol), diisopropylethylamine (0.164 g, 0.22 ml, 1.27 mmol), hydroxybenztriazole (0.114 g, 0.83 mmol), and racemic (2R,5S,6S)-5-Amino-6-hydroxy-2-methyl-azepane-1-carboxylic acid benzyl ester (0.27 g, 0.57 mmol) in DMF (3.2 ml). The reaction was stirred overnight at RT, then was diluted with EtOAc (100 ml), washed with H₂O (3×50 ml), brine (50 ml), dried with magnesium sulfate, filtered, concentrated in vacuo by rotary evaporation, and chromatographed (silica gel, 50% EtOAc/hexanes) to yield the title compound (0.218 g, 72%): 1H NMR: 7.40-7.29 (m, 5H), 6.75 (1H, bd), 5.12 (2H, AB), 5.0 (1H, bs), 4.15-3.72 (m, 2H), 3.06 (1H, d), 1.60-1.30 (m, 2H), 1.60-1.30 (m, 5H), 1.12 (3H, d), 0.97-0.87(6H, dd); Electrospray mass spec: M+H⁺=492.0 i. [(S)-1-((3S,4S,7R)-3-Hydroxy-7-methyl-azepan-4-ylcarbamoyl)-3-methyl-butyl]-carbamic acid tert-butyl ester (2R,5S,6S)-5-((S)-2-tert-Butoxycarbonylamino-4-methyl-pentanoylamino)-6-hydroxy-2-methyl-azepane-1-carboxylic acid benzyl ester (0.169 g, 0.344 mmol) was dissolved in EtOAc (3 ml), MeOH (1 ml). Then 10% Pd/C (0.183 g, 0.172 mmol) was added and the reaction was stirred overnight under a balloon filled with hydrogen gas. The reaction mixture was filtered through Celite, concentrated in vacuo by rotary evaporation and was used in the next reaction without further purification (0.126 g): Electrospray mass spec: M+H⁺=358.11.

j. [(S)-1-((3S,4S,7R)-2-Pyridinesulfonyl-3-hydroxy-7-methyl-azepan-4-ylcarbamoyl)-3-methyl-butyl]-carbamic acid tert-butyl ester 2-Pyridine sulfonyl chloride (0.71 g, 0.4 mmol) was added to a solution of [(S)-1-((3S,4S,7R)-3-hydroxy-7-methyl-azepan-4-ylcarbamoyl)-3-methyl-butyl]-carbamic acid tert-butyl ester (0.126 g, 0.344 mmol), sodium bicarbonate (0.87 g, 1.03 mmol) in CH₂Cl₂ (3 ml) and H₂O (2 ml) and was stirred at RT for 30 minutes. The reaction mixture was diluted with EtOAc (100 ml), washed with H₂O, brine, dried with magnesium sulfate, filtered, concentrated in vacuo by rotary evaporation, and chromatographed (silica gel, 3% MeOH/

CH₂Cl₂) to yield the title compound (0.180 g, 70%): 1H NMR: 8.68 (m, 1H), 8.05 (1H, d), 7.92 (1H, dd), 7.50 (1H, dd), 6.66 (1H, bd), 4.95-4.88 (dd), 4.20-3.87 (m, 3H), 3.65 (1H, bs), 3.40 (1H, d), 1.94-1.57 (m, 4H), 1.45-1.38 (m, 6H), 1.14 (3H, dd), 0.94 (6H, dd); Electrospray mass spec: M+H⁺=499.0 k. (S)-2-Amino-4-methyl-pentanoic acid ((3S,4S,7R)-1-(2-pyridine)-sulfonyl-3-hydroxy-7-methyl-azepan-4-yl)-amide HCl in dioxane (4.0 M, 1.5 ml) was added to a stirred solution of [(S)-1-((3S,4S,7R)-2-pyridinesulfonyl-3-hydroxy-7-methyl-azepan-4-ylcarbamoyl)-3-methyl-butyl]-carbamic acid tert-butyl ester (0.090 g, 0.18 mmol) in MeOH (1.5 ml). The reaction mixture was stirred for 2 h at RT, then was concentrated in vacuo by rotary evaporation and was used in the next reaction without further purification (0.072 g).

l. Benzofuran-2-carboxylic acid {(S)-1-[(3S,4S,7R)-3-hydroxy-7-methyl-1-(pyridine-2-sulfonyl)-azepan-4-ylcarbamoyl]-3-methyl-butyl}-amide 1-(3-Dimethylaminopropyl)-3-ethylcarbodiimide (0.046 g, 0.36 mmol) was added to a solution of 2-benzofurancarboxylic acid (0.032 g, 0.198 mmol), (S)-2-Amino-4-methyl-pentanoic acid ((3S,4S,7R)-1-(2-pyridine)-sulfonyl-3-hydroxy-7-methyl-azepan-4-yl)-amide (0.072 g, 0.18 mmol), diisopropylethylamine (0.046 g, 0.06 ml, 0.36 mmol), hydroxybenztriazole (0.029 g, 0.36 mmol) in DMF (2 ml) and was stirred at RT overnight. The reaction mixture was then warmed to RT and was stirred overnight. The reaction mixture was diluted with EtOAc (10 ml), washed with H₂O, brine, dried with magnesium sulfate, filtered, concentrated in vacuo by rotary evaporation, and chromatographed (silica gel, 2.5% MeOH/CH₂Cl₂) to yield the title compound (0.092 g, 94%): 1H NMR: 8.65 (m, 1H), 8.05 (m, 1H), 7.87 (dd, 1H), 7.62 (dd, 1H), 7.50-7.35 (m, 3H), 7.28-7.20 (m, 1H), 7.07 (m, 1H), 6.92 (1H, bd), 6.80 (bd, 1H), 4.65-4.48 (m, 1H), 4.20-3.87 (m, 3H), 3.65 (1H, bd), 3.40 (1H, dd), 1.94-1.57 (m, 4H), 1.45-1.38 (m, 6H), 1.14 (3H, dd), 0.94 (6H, m); Electrospray mass spec: M+H⁺=542.98 m. Benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide Dess-Martin periodinane (0.077 g, 0.182 mmol) was added to a solution of Benzofuran-2-carboxylic acid {(S)-1-[(3S, 4S,7R)-3-hydroxy-7-methyl-1-(pyridine-2-sulfonyl)-azepan-4-ylcarbamoyl]-3-methyl-butyl}-amide (0.058 g, 0.107 mmol) in CH₂Cl₂ (10 ml) and was stirred at RT for 1 h. The solution was washed with 10% aq. Na₂S₂O₃, then aq. sat. NaHCO₃, then brine. Purification by column chromatography (50% to 80% ethyl acetate/hexanes) gave the title compound (0.056 g, 97%): 1H NMR: 8.72 (m, 1H), 8.0 (d, 1H), 8.92 (dd, 1H), 7.65 (d, 1H), 7.56 (d, 1H), 7.45 (s, 1H), 7.42 (dd, 2H), 7.28 (d, 1H), 7.10 (d, 1H), 5.15 (m, 1H), 4.77 (d, 1H), 4.68 (m, 1H), 4.40 (m, 1H), 3.86 (d, 1H), 2.20-2.08 (m, 2H), 1.78-1.50 (m, 5H), 1.22 (dd, 3H), 0.98 (m, 6H); Electrospray mass spec: M+H⁺=541.2.

Example 7

2,2,4-Trideutero-benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide Benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide is dissolved in d4-methanol (CD₃OD) and D₂O (10:1), then triethyl amine is added and the reaction mixture is stirred for 3 days. Azeotroping with toluene by concentrating in vacuo provides the title compound.

Example 8

Furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide

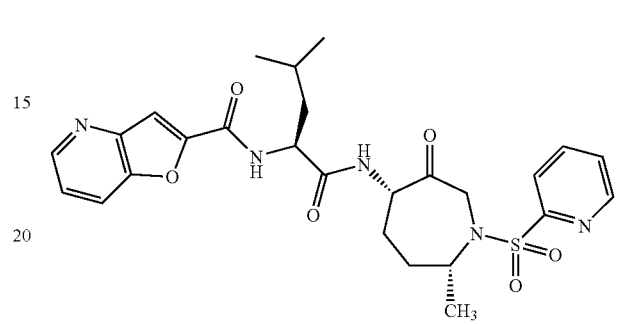

a. ((R)-2-Iodo-1-methyl-ethyl)-carbamic acid benzyl ester

Triphenylphospine (24 g, 91.8 mmol) was added to a solution of imidazole (12.5 g, 184 mmol) in CH₂Cl₂ (231 ml), then was cooled to 0 degrees C. Iodine (23.3 g, 91.8 mmol) was added to the suspension. The reaction mixture turned yellow, then faintly brown. After 5 minutes ((R)-2-hydroxy-1-methyl-ethyl)-carbamic acid benzyl ester (9.59 g, 45.9 mmol) was added and the reaction mixture was warmed to RT then stirred for 3 h. Then, H₂O (7 ml) was added and the reaction mixture was partitioned between CH₂Cl₂ (300 ml) and H₂O (600 ml). The aqueous layer was extracted again with CH₂Cl₂ (200 ml). The combined organic layer was then washed with a solution of 1:9 aq. saturated Na₂S₂O₃: H₂O (140 ml), then brine (400 ml). The combined organics were dried with MgSO₄, filtered, concentrated in vacuo, then filtered through a plug of silica gel washing with 15% EtOAc/hexanes (1.5 liter). The solution was concentrated in vacuo, then the solid was washed with hexane and the resultant white solid was used in the next reaction without further purification (11 g, 75%).

b. ((R)-1-Methyl-pent-4-enyl)-carbamic acid benzyl ester

Copper (I) bromide-dimethyl sulfide (1.93 g, 9.4 mmol) was dissolved in distilled THF (24 ml), then was cooled to −78 degrees C. A solution of allyl magnesium chloride (9.4 ml, 2M in THF, Aldrich) was added dropwise, then the solution was stirred for 30 minutes. ((R)-2-Iodo-1-methyl-ethyl)-carbamic acid benzyl ester (1.5 g, 4.7 mmol) in distilled THF (3 ml) was added dropwise, then the reaction was warmed to −40 degrees C. and was stirred for 2.5 h. The reaction mixture was quenched with aq. sat. NH₄Cl (4 ml) at −40 degrees C., warmed to RT and the gray reaction mixture turned sky blue. THF was removed in vacuo. Then, Et₂O was added and the reaction mixture was filtered to remove precipitated solids. The solids were washed with additional Et₂O. The combined organics were extracted with 10% NH₄OH (3×), then brine. The combined organics were dried with MgSO₄, filtered, concentrated in vacuo, then filtered through a plug of silica gel washing with 20% EtOAc/hexanes (100 ml). The solution was concentrated in vacuo, then the resultant colorless oil was used in the next reaction without further purification (0.8 g, 73%).

c. Allyl-((R)-1-methyl-pent-4-enyl)-carbamic acid benzyl ester ((R)-1-Methyl-pent-4-enyl)-carbamic acid benzyl ester (790 mg, 3.39 mmol) was dissolved in DMF (8 ml) and was cooled to 0 degrees C. Sodium hydride (60% dispersion, 271 mg, 6.78 mmol) was added and the reaction was stirred for 15 minutes. Allyl bromide (1.23 g, 0.88 ml, 10.17 mmol) was added and the reaction mixture was stirred for 3 h at 0 degrees C. $H_2O$ (10 ml) was added, then 2N HCl was added dropwise adjusting the pH to 1. The reaction mixture was extracted with $Et_2O$ (2×50 ml). The combined organics were washed with aq. 2N HCl, then aq. $NaHCO_3$, then brine. The combined organics were dried with $MgSO_4$, filtered, concentrated in vacuo, then chromatographed on silica gel (5% EtOAc/hexanes) to yield the title compound as a colorless oil (883 mg, 95%).

d. 2-Methyl-2,3,4,7-tetrahydro-azepine-1-carboxylic acid benzyl ester

Allyl-(1-methyl-pent-4-enyl)-carbamic acid benzyl ester (0.872 g, 3.19 mmol) was dissolved in $CH_2Cl_2$ (10 ml) and a stream of argon gas was bubbled into the reaction mixture for 10 minutes. Then bis(tricyclohexylphosphine)benzylidine ruthenium(IV) dichloride (Strem Chemicals, Grubbs' catalyst, 19 mg, 0.0227 mmol) was added and the reaction mixture was refluxed for 2 h. Additional bis(tricyclohexylphosphine)benzylidine ruthenium(IV) dichloride (mg, 0.0108 mmol) was added and the reaction mixture was refluxed for an additional 1.5 hours. The reaction was cooled to RT under argon overnight, then was concentrated in vacuo by rotary evaporation, then was chromatographed (silica gel, 5% EtOAc/hexanes) to give the title compound (0.72 g, 92%): 1H NMR: 7.35-7.20 (m, 5H), 5.65 (1H, m), 5.13 (2H, AB), 4.45-4.05 (m, 2H), 3.56 (1H, d), 2.25-2.10 (m, 2H), 1.90-1.60 (m, 2H), 1.12 (3H, d); Liquid Chromatgraphy/Electrospray mass spec: $M+H^+$=246.2.

e. (1S,4R,7R)-4-Methyl-8-oxa-3-aza-bicyclo[5.1.0]octane-3-carboxylic acid benzyl ester m-Chloro-perbenzoic acid (1.10 g, 57-86% pure) was added to a solution of 2-methyl-2,3,4,7-tetrahydro-azepine-1-carboxylic acid benzyl ester (0.72 g, 2.94 mmol) in $CH_2Cl_2$ at 0 degrees C. The reaction mixture was stirred for half an hour, then was warmed to RT. Additional m-chloro-perbenzoic acid (0.660 g, 57-86% pure) was added and the reaction was stirred 2 h. The reaction mixture was concentrated in vacuo by rotary evaporation, then 80 ml of 9:1 hexanes/EtOAc was added and the reaction mixture was filtered. The filtrate was concentrated in vacuo by rotary evaporation, then was chromatographed (silica gel, 20% EtOAc:hexanes) to give (1S,4R,7S)$_4$-methyl-8-oxa-3-aza-bicyclo[5.1.0]octane-3-carboxylic acid benzyl ester (0.450 g, 75%) and the title compound (0.15 g, 25% yield): 1H NMR: 7.42-7.22 (m, 5H), 5.13 (2H, s), 4.50-4.15 (m, 2H), 3.27 (1H, d), 3.12-2.95 (1H, m), 2.15-1.70 (m, 2H), 1.47 (m, 2H), 1.12 (3H, d); Liquid Chromatgraphy/Electrospray mass spec: $M+H^+$=262.0.

f. (2R,5S,6S)-5-Azido-6-hydroxy-2-methyl-azepane-1-carboxylic acid benzyl ester

Sodium azide (0.139 g, 2.14 mmol) was added to a solution of (1S,4R,7R)-4-methyl-8-oxa-3-aza-bicyclo[5.1.0]octane-3-carboxylic acid benzyl ester (0.186 g, 0.71 mmol) and ammonium chloride (0.114 g, 2.14 mmol) in MeOH (1.5 ml) and $H_2O$ (0.15 ml), then was refluxed for 6 h. The reaction mixture was concentrated in vacuo by rotary evaporation, then was diluted with water (5 ml) and extracted with EtOAc (10 ml). The organic layer was then extracted with water, brine, dried with $MgSO_4$, filtered, concentrated in vacuo by rotary evaporation, and chromatographed (silica gel, 20% EtOAc/hexanes) to yield the title compound (0.192 g, 89%): 7.39-7.30 (m, 5H), 5.15 (2H, s), 4.10-3.67 (m, 2H), 3.10 (1H, d), 1.85-1.53 (m, 4H), 1.09 (3H, d); Liquid Chromatgraphy/Electrospray mass spec: $M+H^+$=305.2.

g. (2R,5S,6S)-5-Amino-6-hydroxy-2-methyl-azepane-1-carboxylic acid benzyl ester

Triphenylphosphine (0.25 g, 0.952 mmol) was added to a solution of (2R,5S,6S)-5-azido-6-hydroxy-2-methyl-azepane-1-carboxylic acid benzyl ester (0.193 g, 0.635 mmol) in THF (10 ml) and $H_2O$ (0.04 ml), then was heated to 45 degrees C. overnight. The reaction mixture was then diluted with toluene (100 ml×2) and was azeotroped in vacuo by rotary evaporation twice. The resulting oil was dissolved in MeOH and HCl in $Et_2O$ and the resulting salt was collected following filtration and was used in the next reaction without further purification (0.27 g, 90%).

h. (2R,5S,6S)-5-((S)-2-tert-Butoxycarbonylamino-4-methyl-pentanoylamino)-6-hydroxy-2-methyl-azepane-1-carboxylic acid benzyl ester 1-(3-Dimethylaminopropyl)-3-ethylcarbodiimide (0.164 g, 0.22 mmol) was added to a solution of Boc-Leucine-hydrate (0.190 g, 0.76 mmol), diisopropylethylamine (0.164 g, 0.22 ml, 1.27 mmol), hydroxybenztriazole (0.114 g, 0.83 mmol), and racemic (2R,5S,6S)-5-Amino-6-hydroxy-2-methyl-azepane-1-carboxylic acid benzyl ester (0.27 g, 0.57 mmol) in DMF (3.2 ml). The reaction was stirred overnight at RT, then was diluted with EtOAc (100 ml), washed with $H_2O$ (3×50 ml), brine (50 ml), dried with magnesium sulfate, filtered, concentrated in vacuo by rotary evaporation, and chromatographed (silica gel, 50% EtOAc/hexanes) to yield the title compound (0.218 g, 72%): 1H NMR: 7.40-7.29 (m, 5H), 6.75 (1H, bd), 5.12 (2H, AB), 5.0 (1H, bs), 4.15-3.72 (m, 2H), 3.06 (1H, d), 1.60-1.30 (m, 2H), 1.60-1.30 (m, 5H), 1.12 (3H, d), 0.97-0.87(6H, dd); Electrospray mass spec: $M+H^+$=492.0 i. [(S)-1-((3S,4S,7R)-3-Hydroxy-7-methyl-azepan-4-ylcarbamoyl)-3-methyl-butyl]-carbamic acid tert-butyl ester (2R,5S,6S)-5-((S)-2-tert-Butoxycarbonylamino-4-methyl-pentanoylamino)-6-hydroxy-2-methyl-azepane-1-carboxylic acid benzyl ester (0.169 g, 0.344 mmol) was dissolved in EtOAc (3 ml), MeOH (1 ml). Then 10% Pd/C (0.183 g, 0.172 mmol) was added and the reaction was stirred overnight under a balloon filled with hydrogen gas. The reaction mixture was filtered through Celite, concentrated in vacuo by rotary evaporation and was used in the next reaction without further purification (0.126 g): Electrospray mass spec: $M+H^+$=358.11.

j. [(S)-1-((3S,4S,7R)-2-Pyridinesulfonyl-3-hydroxy-7-methyl-azepan-4-ylcarbamoyl)-3-methyl-butyl]-carbamic acid tert-butyl ester 2-Pyridine sulfonyl chloride (0.71 g, 0.4 mmol) was added to a solution of. [(S)-1-((3S,4S,7R)-3-Hydroxy-7-methyl-azepan-4-ylcarbamoyl)-3-methyl-butyl]-carbamic acid tert-butyl ester (0.126 g, 0.344 mmol), sodium bicarbonate (0.87 g, 1.03 mmol) in $CH_2Cl_2$ (3 ml) and $H_2O$ (2 ml) and was stirred at RT for 30 minutes. The reaction mixture was diluted with EtOAc (100 ml), washed with $H_2O$, brine, dried with magnesium sulfate, filtered, concentrated in vacuo by rotary evaporation, and chromatographed (silica gel, 3% MeOH/$CH_2Cl_2$) to yield the title compound (0.180 g, 70%): 1H NMR: 8.68 (m, 1H), 8.05 (1H, d), 7.92 (1H, dd), 7.50 (1H, dd), 6.66 (1H, bd), 4.95-4.88 (dd), 4.20-3.87 (m, 3H), 3.65 (1H, bs), 3.40 (1H, d), 1.94-1.57 (m, 4H), 1.45-1.38 (m, 6H), 1.14 (3H, dd), 0.94 (6H, dd); Electrospray mass spec: $M+H^+$=499.0 k. (S)-2-Amino-4-methyl-pentanoic acid ((3S,4S,7R)-1-(2-pyridine)-sulfonyl-3-hydroxy-7-methyl-azepan-4-yl)-amide HCl in dioxane (4.0 M, 1.5 ml) was added to a stirred solution of [(S)-1-((3S,4S,7R)-2-pyridinesulfonyl-3-hydroxy-7-methyl-azepan-4-ylcarbamoyl)-3-methyl-butyl]-carbamic acid tert-butyl ester (0.090 g, 0.18 mmol) in MeOH (1.5 ml). The reaction mixture was stirred for 2 h at RT, then was concentrated in vacuo by rotary evaporation and was used in the next reaction without further purification (0.072 g).

l. Furo[3,2-b]pyridine-2-carboxylic acid {(S)-1-[(3S,4S,7R)-3-hydroxy-7-methyl-1-(pyridine-2-sulfonyl)-azepan-4-ylcarbamoyl]-3-methyl-butyl}-amide 1-(3-Dimethylaminopropyl)-3-ethylcarbodiimide (0.035 g, 0.185 mmol) was added to a solution of Furo[3,2-b]pyridine-2-carboxylic acid (0.034 g, 0.2 mmol, as described in Shiotani, Shunsaku; Morita, Hiroyuki *J. Heterocycl. Chem.* 1991, 28 (6), 1469-1480), (S)-2-Amino-4-methyl-pentanoic acid ((3S,4S,7R)-1-(2-pyridine)-sulfonyl-3-hydroxy-7-methyl-azepan-4-yl)-amide (0.077 g, 0.16 mmol), diisopropylethylamine (0.05 g, 0.07 ml, 0.4 mmol), hydroxybenztriazole (0.025 g, 0.185 mmol) in DMF (1.5 ml) and was stirred at RT overnight. The reaction mixture was then warmed to RT and was stirred overnight. The reaction mixture was diluted with EtOAc (20 ml), washed with H$_2$O, brine, dried with magnesium sulfate, filtered, concentrated in vacuo by rotary evaporation, and chromatographed (silica gel, 2.5% MeOH/CH$_2$Cl$_2$) to yield the title compound (0.056 g, 64%): 1H NMR: 8.68 (1H, d), 7.96 (1H, d), 7.87 (1H, d), 7.82 (1H, dd), 7.65 (1H, d), 7.61 (1H, s), 7.45 (1H, dd), 7.33 (1H, dd), 7.08 (d, 1H), 4.69 (q, 1H), 3.90-3.45 (m, 3H), 3.71 (q, 1H), 3.12-3.04 (m, 1H), 2.04-1.95 (m, 1H), 1.88-1.65 (m, 3H), 1.55-1.45 (m, 2H), 0.95 (m, 9H); Electrospray mass spec: M+H$^+$ =543.86 m. Furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide Sulfur trioxide-pyridine complex (0.050 g, 0.31 mmol) was added to a solution of Furo[3,2-b]pyridine-2-carboxylic acid {(S)-1-[(3S,4S,7R)-3-hydroxy-7-methyl-1-(pyridine-2-sulfonyl)-azepan-4-ylcarbamoyl]-3-methyl-butyl}-amide (0.056 g, 0.103 mmol) in DMSO (1.0 ml) and triethylamine (0.085 ml, 0.6 mmol) was stirred at RT for 1 h. The reaction was incomplete; therefore, additional triethyl amine (0.04 ml, 0.3 mmol) and sulfur trioxide-pyridine complex (0.0.025 g, 0.15 mmol) was added ant the reaction was stirred an additional hour. The reaction mixture was diluted with water, then was extracted with EtOAc. Then, the organic layer was was extracted with brine. The combined organics were dried with magnesium sulfate, filtered, concentrated in vacuo, and purified by column chromatography (50% to 80% ethyl acetate/hexanes) gave the title compound (12.5 mg, 22%): 1H NMR: 1H NMR: 8.72 (1H, d), 8.66 (1H, d), 8.02 (1H, d), 7.93 (1H, dd), 7.85 (1H, d), 7.53 (1H, dd), 7.40 (1H, dd), 7.25 (d, 1H), 6.95 (1H, d), 5.15 (m, 1H), 4.77 (m, 2H), 3.72 (q, 1H), 2.20-2.08 (m, 2H), 1.78-1.50 (m, 5H), 1.22 (dd, 3H), 0.98 (m, 6H); Electrospray mass spec: M+H$^+$=542.2

Example 9

Preparation of 2,2,4-Trideutero-furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide

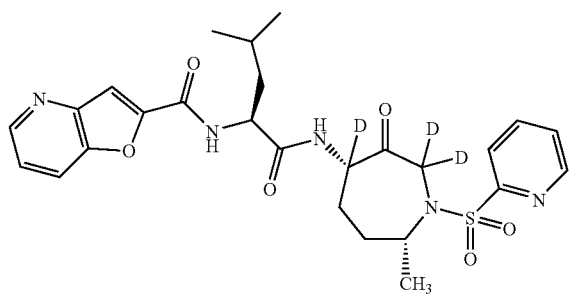

Furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide is dissolved in d4-methanol (CD$_3$OD) and D$_2$O (10:1), then triethyl amine is added and the reaction mixture is stirred for 3 days. Azeotroping with toluene by concentrating in vacuo provides the title compound.

Example 10

Preparation of 3-methyl-furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide

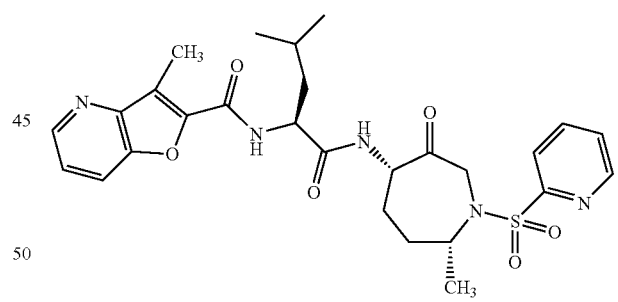

Following the procedure of Example 8 (a-m), except substituting "3-methyl-furo[3,2-b]pyridine-2-carboxylic acid (as described in Shiotani, Shunsaku; Morita, Hiroyuki *J. Heterocycl. Chem.* 1991, 28 (6), 1469-1480)" for "furo[3,2-b]pyridine-2-carboxylic acid" gave the title compound: MS (M+H+); 1H NMR: 8.72 (d, 1H), 8.66 (d, 1H), 8.02 (d, 1H), 7.93 (dd, 1H), 7.80 (d, 1H), 7.53 (dd, 1H), 7.39 (dd, 1H), 7.66 (d, 1H), 6.90 (d, 1H), 5.56-5.12 (m, 1H), 4.72 (q, 1H), 4.42 (q, 1H), 3.87 (d, 1H), 2.70 (s, 3H), 2.24-2.14 (m, 2H), 1.75 (m, 2H), 1.65-1.42 (m, 4H), 1.2-0.95 (m, 9H); Electrospray mass spec: M+H$^+$=556.2.

Example 11

Preparation of 2,2,4-Trideutero-3-methyl-furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide

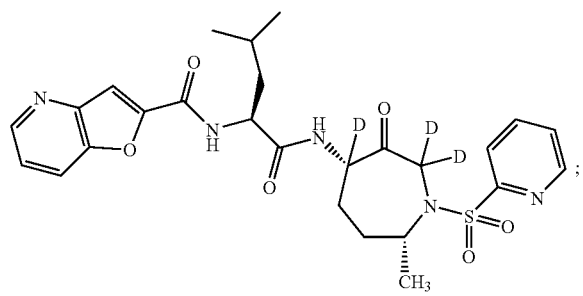

Following the procedure of Example 9, except substituting 3-methyl-furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide" for "furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide" gives the title compound.

Example 12

Preparation of Quinoline-6-carboxylic acid {(S)-3-methyl-1-[(4S,7R)-7-methyl-3-oxo-1-(pyridine-2-sulfonyl)-azepan-4-ylcarbamoyl]-butyl}-amide

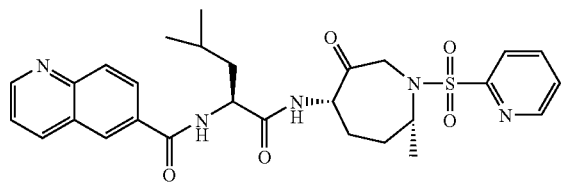

a. ((R)-2-Iodo-1-methyl-ethyl)-carbamic acid benzyl ester

Triphenylphospine (24 g, 91.8 mmol) was added to a solution of imidazole (12.5 g, 184 mmol) in $CH_2Cl_2$ (231 ml), then was cooled to 0 degrees C. Iodine (23.3 g, 91.8 mmol) was added to the suspension. The reaction mixture turned yellow, then faintly brown. After 5 minutes ((R)-2-hydroxy-1-methyl-ethyl)-carbamic acid benzyl ester (9.59 g, 45.9 mmol) was added and the reaction mixture was warmed to RT then stirred for 3 h. Then, $H_2O$ (7 ml) was added and the reaction mixture was partitioned between $CH_2Cl_2$ (300 ml) and $H_2O$ (600 ml). The aqueous layer was extracted again with $CH_2Cl_2$ (200 ml). The combined organic layer was then washed with a solution of 1:9 aq. saturated $Na_2S_2O_3$: $H_2O$ (140 ml), then brine (400 ml). The combined organics were dried with $MgSO_4$, filtered, concentrated in vacuo, then filtered through a plug of silica gel washing with 15% EtOAc/hexanes (1.5 liter). The solution was concentrated in vacuo, then the solid was washed with hexane and the resultant white solid was used in the next reaction without further purification (11 g, 75%).

b. ((R)-1-Methyl-pent-4-enyl)-carbamic acid benzyl ester

Copper (I) bromide-dimethyl sulfide (1.93 g, 9.4 mmol) was dissolved in distilled THF (24 ml), then was cooled to −78 degrees C. A solution of allyl magnesium chloride (9.4 ml, 2M in THF, Aldrich) was added dropwise, then the solution was stirred for 30 minutes. ((R)-2-Iodo-1-methyl-ethyl)-carbamic acid benzyl ester (1.5 g, 4.7 mmol) in distilled THF (3 ml) was added dropwise, then the reaction was warmed to −40 degrees C. and was stirred for 2.5 h. The reaction mixture was quenched with aq. sat. $NH_4Cl$ (4 ml) at −40 degrees C., warmed to RT and the gray reaction mixture turned sky blue. THF was removed in vacuo. Then, $Et_2O$ was added and the reaction mixture was filtered to remove precipitated solids. The solids were washed with additional $Et_2O$. The combined organics were extracted with 10% $NH_4OH$ (3×), then brine. The combined organics were dried with $MgSO_4$, filtered, concentrated in vacuo, then filtered through a plug of silica gel washing with 20% EtOAc/hexanes (100 ml). The solution was concentrated in vacuo, then the resultant colorless oil was used in the next reaction without further purification (0.8 g, 73%).

c. Allyl-((R)-1-methyl-pent-4-enyl)-carbamic acid benzyl ester ((R)-1-Methyl-pent-4-enyl)-carbamic acid benzyl ester (790 mg, 3.39 mmol) was dissolved in DMF (8 ml) and was cooled to 0 degrees C. Sodium hydride (60% dispersion, 271 mg, 6.78 mmol) was added and the reaction was stirred for 15 minutes. Allyl bromide (1.23 g, 0.88 ml, 10.17 mmol) was added and the reaction mixture was stirred for 3 h at 0 degrees C. $H_2O$ (10 ml) was added, then 2N HCl was added dropwise adjusting the pH to 1. The reaction mixture was extracted with $Et_2O$ (2×50 ml). The combined organics were washed with aq. 2N HCl, then aq. $NaHCO_3$, then brine. The combined organics were dried with $MgSO_4$, filtered, concentrated in vacuo, then chromatographed on silica gel (5% EtOAc/hexanes) to yield the title compound as a colorless oil (883 mg, 95%).

d. 2-Methyl-2,3,4,7-tetrahydro-azepine-1-carboxylic acid benzyl ester

Allyl-(1-methyl-pent-4-enyl)-carbamic acid benzyl ester (0.872 g, 3.19 mmol) was dissolved in $CH_2Cl_2$ (10 ml) and a stream of argon gas was bubbled into the reaction mixture for 10 minutes. Then bis(tricyclohexylphosphine)benzylidine ruthenium(IV) dichloride (Strem Chemicals, Grubbs' catalyst, 19 mg, 0.0227 mmol) was added and the reaction mixture was refluxed for 2 h. Additional bis(tricyclohexylphosphine)benzylidine ruthenium(IV) dichloride (mg, 0.0108 mmol) was added and the reaction mixture was refluxed for an additional 1.5 hours. The reaction was cooled to RT under argon overnight, then was concentrated in vacuo by rotary evaporation, then was chromatographed (silica gel, 5% EtOAc/hexanes) to give the title compound (0.72 g, 92%): 1H NMR: 7.35-7.20 (m, 5H), 5.65 (1H, m), 5.13 (2H, AB), 4.45-4.05 (m, 2H), 3.56 (1H, d), 2.25-2.10 (m, 2H), 1.90-1.60 (m, 2H), 1.12 (3H, d); Liquid Chromatgraphy/Electrospray mass spec: $M+H^+=246.2$.

e. (1S,4R,7R)-4-Methyl-8-oxa-3-aza-bicyclo[5.1.0]octane-3-carboxylic acid benzyl ester m-Chloro-perbenzoic acid (1.10 g, 57-86% pure) was added to a solution of 2-methyl-2,3,4,7-tetrahydro-azepine-1-carboxylic acid benzyl ester (0.72 g, 2.94 mmol) in $CH_2Cl_2$ at 0 degrees C. The reaction mixture was stirred for half an hour, then was warmed to RT. Additional m-chloro-perbenzoic acid (0.660 g, 57-86% pure) was added and the reaction was stirred 2 h. The reaction mixture was concentrated in vacuo by rotary evaporation, then 80 ml of 9:1 hexanes/EtOAc was added and the reaction mixture was filtered. The filtrate was concentrated in vacuo by rotary evaporation, then was chromatographed (silica gel, 20% EtOAc:hexanes) to give (1S,4R,7S)$_4$-methyl-8-oxa-3-aza-bicyclo[5.1.0]octane-3-carboxylic acid benzyl ester (0.450 g, 75%) and the title compound (0.15 g, 25% yield): 1H NMR: 7.42-7.22 (m, 5H), 5.13 (2H, s), 4.50-4.15 (m, 2H), 3.27 (1H, d), 3.12-2.95 (1H, m), 2.15-1.70 (m, 2H), 1.47 (m, 2H), 1.12 (3H, d); Liquid Chromatgraphy/Electrospray mass spec: M+H$^+$=262.0.

f. (2R,5S,6S)-5-Azido-6-hydroxy-2-methyl-azepane-1-carboxylic acid benzyl ester

Sodium azide (0.139 g, 2.14 mmol) was added to a solution of (1S,4R,7R)-4-methyl-8-oxa-3-aza-bicyclo[5.1.0]octane-3-carboxylic acid benzyl ester (0.186 g, 0.71 mmol) and ammonium chloride (0.114 g, 2.14 mmol) in MeOH (1.5 ml) and H$_2$O (0.15 ml), then was refluxed for 6 h. The reaction mixture was concentrated in vacuo by rotary evaporation, then was diluted with water (5 ml) and extracted with EtOAc (10 ml). The organic layer was then extracted with water, brine, dried with MgSO$_4$, filtered, concentrated in vacuo by rotary evaporation, and chromatographed (silica gel, 20% EtOAc/hexanes) to yield the title compound (0.192 g, 89%): 7.39-7.30 (m, 5H), 5.15 (2H, s), 4.10-3.67 (m, 2H), 3.10 (1H, d), 1.85-1.53 (m, 4H), 1.09 (3H, d); Liquid Chromatgraphy/Electrospray mass spec: M+H$^+$=305.2.

g. (2R,5S,6S)-5-Amino-6-hydroxy-2-methyl-azepane-1-carboxylic acid benzyl ester

Triphenylphosphine (0.25 g, 0.952 mmol) was added to a solution of (2R,5S,6S)-5-azido-6-hydroxy-2-methyl-azepane-1-carboxylic acid benzyl ester (0.193 g, 0.635 mmol) in THF (10 ml) and H$_2$O (0.04 ml), then was heated to 45 degrees C. overnight. The reaction mixture was then diluted with toluene (100 ml×2) and was azeotroped in vacuo by rotary evaporation twice. The resulting oil was dissolved in MeOH and HCl in Et$_2$O and the resulting salt was collected following filtration and was used in the next reaction without further purification (0.27 g, 90%).

h. (2R,5S,6S)-5-((S)-2-tert-Butoxycarbonylamino-4-methyl-pentanoylamino)-6-hydroxy-2-methyl-azepane-1-carboxylic acid benzyl ester 1-(3-Dimethylaminopropyl)-3-ethylcarbodiimide (0.164 g, 0.22 mmol) was added to a solution of Boc-Leucine-hydrate (0.190 g, 0.76 mmol), diisopropylethylamine (0.164 g, 0.22 ml, 1.27 mmol), hydroxybenztriazole (0.114 g, 0.83 mmol), and racemic (2R,5S,6S)-5-Amino-6-hydroxy-2-methyl-azepane-1-carboxylic acid benzyl ester (0.27 g, 0.57 mmol) in DMF (3.2 ml). The reaction was stirred overnight at RT, then was diluted with EtOAc (100 ml), washed with H$_2$O (3×50 ml), brine (50 ml), dried with magnesium sulfate, filtered, concentrated in vacuo by rotary evaporation, and chromatographed (silica gel, 50% EtOAc/hexanes) to yield the title compound (0.218 g, 72%): 1H NMR: 7.40-7.29 (m, 5H), 6.75 (1H, bd), 5.12 (2H, AB), 5.0 (1H, bs), 4.15-3.72 (m, 2H), 3.06 (1H, d), 1.60-1.30 (m, 2H), 1.60-1.30 (m, 5H), 1.12 (3H, d), 0.97-0.87(6H, dd); Electrospray mass spec: M+H$^+$=492.0 i. [(S)-1-((3S,4S,7R)-3-Hydroxy-7-methyl-azepan-4-ylcarbamoyl)-3-methyl-butyl]-carbamic acid tert-butyl ester (2R,5S,6S)-5-((S)-2-tert-Butoxycarbonylamino-4-methyl-pentanoylamino)-6-hydroxy-2-methyl-azepane-1-carboxylic acid benzyl ester (0.169 g, 0.344 mmol) was dissolved in EtOAc (3 ml), MeOH (1 ml). Then 10% Pd/C (0.183 g, 0.172 mmol) was added and the reaction was stirred overnight under a balloon filled with hydrogen gas. The reaction mixture was filtered through Celite, concentrated in vacuo by rotary evaporation and was used in the next reaction without further purification (0.126 g): Electrospray mass spec: M+H$^+$=358.11.

j. [(S)-1-((3S,4S,7R)-2-Pyridinesulfonyl-3-hydroxy-7-methyl-azepan-4-ylcarbamoyl)-3-methyl-butyl]-carbamic acid tert-butyl ester Pyridine-2-sulfonyl chloride (0.71 g, 0.4 mmol) was added to a solution of [(S)-1-((3S,4S,7R)-3-Hydroxy-7-methyl-azepan-4-ylcarbamoyl)-3-methyl-butyl]-carbamic acid tert-butyl ester (0.126 g, 0.344 mmol), sodium bicarbonate (0.87 g, 1.03 mmol) in CH$_2$Cl$_2$ (3 ml) and H$_2$O (2 ml) and was stirred at RT for 30 minutes. The reaction mixture was diluted with EtOAc (100 ml), washed with H$_2$O, brine, dried with magnesium sulfate, filtered, concentrated in vacuo by rotary evaporation, and chromatographed (silica gel, 3% MeOH/CH$_2$Cl$_2$) to yield the title compound (0.180 g, 70%): 1H NMR: 8.68 (m, 1H), 8.05 (1H, d), 7.92 (1H, dd), 7.50 (1H, dd), 6.66 (1H, bd), 4.95-4.88 (dd), 4.20-3.87 (m, 3H), 3.65 (1H, bs), 3.40 (1H, d), 1.94-1.57 (m, 4H), 1.45-1.38 (m, 6H), 1.14 (3H, dd), 0.94 (6H, dd); Electrospray mass spec: M+H$^+$=499.0 k. (S)-2-Amino-4-methyl-pentanoic acid ((3S,4S,7R)-1-(2-pyridine)-sulfonyl-3-hydroxy-7-methyl-azepan-4-yl)-amide HCl in dioxane (4.0 M, 1.5 ml) was added to a stirred solution of [(S)-1-((3S,4S,7R)-2-pyridinesulfonyl-3-hydroxy-7-methyl-azepan-4-ylcarbamoyl)-3-methyl-butyl]-carbamic acid tert-butyl ester (0.090 g, 0.18 mmol) in MeOH (1.5 ml). The reaction mixture was stirred for 2 h at RT, then was concentrated in vacuo by rotary evaporation and was used in the next reaction without further purification (0.072 g).

l. Quinoline-6-carboxylic acid {(S)-3-methyl-1-[(4S,7R)-7-methyl-3-hydroxy-1-(pyridine-2-sulfonyl)-azepan-4-ylcarbamoyl]-butyl}-amide 1-(3-Dimethylaminopropyl)-3-ethylcarbodiimide (76 mg, 0.4 mmol) was added to a solution of Quinoline-6-carboxylic acid (64 mg, 0.37 mmol), (S)-2-Amino-4-methyl-pentanoic acid ((3S,4S,7R)-1-(2-pyridine)-sulfonyl-3-hydroxy-7-methyl-azepan-4-yl)-amide (160 mg, 0.37 mmol), diisopropylethylamine (56 mg, 0.075 ml, 0.43 mmol), hydroxybenztriazole (50 mg, 0.37 mmol) in DMF (3 ml) and was stirred at RT overnight. The reaction mixture was then warmed to RT and was stirred overnight. The reaction mixture was diluted with EtOAc (20 ml), washed with H$_2$O, brine, dried with magnesium sulfate, filtered, concentrated in vacuo by rotary evaporation, and chromatographed (silica gel, 4.5% MeOH/CH$_2$Cl$_2$) to yield the title compound (138 mg, 69%): 1H NMR: 8.90 (s, 1), 8.60 (s, 1H), 8.30 (s, 1H), 7.95-8.10 (m, 4H), 7.85-7.95 (m, 1H), 7.70 (d, 1H), 7.35-7.50 (m, 3H), 4.75-4.85 (m, 1H), 4.10 (d, 1H), 4.0 (bs, 1H), 3.85 (bs, 1H), 3.80 (s, 1H), 3.45 (d, 1H), 1.60-1.75 (m, 3H), 1.40-1.50 (m, 1H), 0.90-1.0 (m, 9H); Electrospray mass spec: M+H$^+$=554.28 (M+H$^+$); 1107.38 (2M+H$^+$).

m. Quinoline-6-carboxylic acid {(S)-3-methyl-1-[(4S,7R)-7-methyl-3-oxo-1-(pyridine-2-sulfonyl)-azepan-4-ylcarbamoyl]-butyl}-amide Sulfur trioxide-pyridine complex (11 mg, 0.7 mmol) was added to a solution of quinoline-6-carboxylic acid {(S)-3-methyl-1-[(4S,7R)-7-methyl-3-hydroxy-1-(pyridine-2-sulfonyl)-azepan-4-ylcarbamoyl]-butyl}-amide (130 mg, 0.235 mmol) in DMSO (2.0 ml) and triethylamine (0.2 ml, 1.4 mmol) was stirred at RT for 1 h. The reaction was incomplete; therefore, additional triethyl amine (0.2 ml, 1.4 mmol) and sulfur trioxide-pyridine complex (11 mg, 0.7 mmol) was added and the reaction was stirred an additional hour. The reaction mixture was diluted with water, then was extracted with EtOAc. Then, the organic layer was was extracted with brine. The combined organics were dried with magnesium sulfate, filtered, concentrated in vacuo, and purified by column chromatography (3% MeOH/CH$_2$Cl$_2$) gave the title compound (100 mg, 77%): 1H NMR:9.0 (sm 1H), 8.70 (s, 1H), 7.90-8.30 (m, 6H), 7.50-7.55 (m, 2H), 7.10 (d, 1H), 7.0 (d, 1H), 5.10-5.15 (m, 1H), 4.70-4.80 (m, 2H), 4.35-4.40 (m, 1H), 3.85 (d, 1H), 2.0-2.25 (m, 3H), 1.70-1.80 (m, 2H), 1.60-1.70 (m, 2H), 0.90-1.10 (m, 9H); Electrospray mass spec: M+H$^+$=552.4

Example 13

Preparation of Quinoline-3-carboxylic acid {(S)-3-methyl-1-[(4S,7R)-7-methyl-3-oxo-1-(pyridine-2-sulfonyl)-azepan-4-ylcarbamoyl]-butyl}-amide

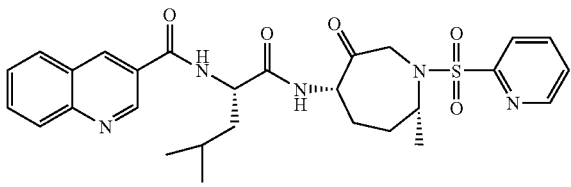

Following the procedure of Example 12 (a-m), except substituting "quinoline-3-carboxylic acid" for "quinoline-6-carboxylic acid" gave the title compound: 1H NMR: 9.30 (s, 1H), 8.70 (s, 1H), 8.60 (s, 1H), 8.20 (d, 1H), 7.80-8.0 (m, 4H), 7.65 (t, 1H), 7.50 9d, 1H), 7.20 (d, 1H), 7.10 (d, 1H), 5.70-5.85 (m, 2H), 5.10-5.20 (m, 1H), 4.35-4.45 (m, 1H), 3.85 (d, 1H), 2.10-2.25 (m, 2H), 1.70-1.80 (m, 3H), 1.45-1.65 (m, 2H), 0.90-1.10 (m, 9H); Electrospray mass spec: M+H$^+$=552.4.

Example 14

Preparation of 5-Methoxy-benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide

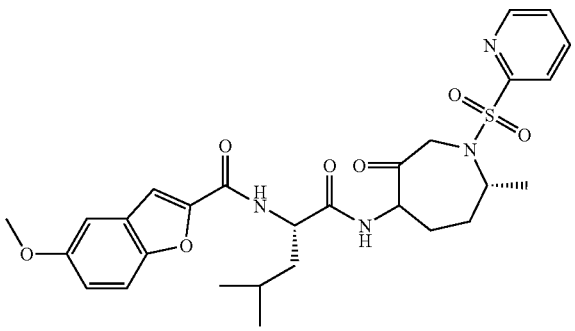

Following the procedure of Example 12 (a-m), except substituting "5-methoxy-benzofuran-2-carboxylic acid" for "quinoline-6-carboxylic acid" gave the title compound: 1H NMR: 8.73 (d,1H), 7.95(m,2H), 7.55(m,1H), 7.43(m,2H), 7.09 (m,3H), 6.93(d,1H), 5.15(m,1H), 4.78(d,1H), 4.71(m, 1H), 4.43(m,1H), 3.89(d,1H), 3.86(s,3H), 2.18(m,2H), 1.56-1.77(m,5H), 0.95(m,9H). Electrospray mass spec: M+H$^+$=571.4 (M+H)$^+$.

Example 15

Preparation of 3-Methyl-benzofuran-2-carboxylic acid {(S)-3-methyl-1-[(4S,7R)-7-methyl-3-oxo-1-(pyridine-2-sulfonyl)-azepan-4-ylcarbamoyl]-butyl}-amide

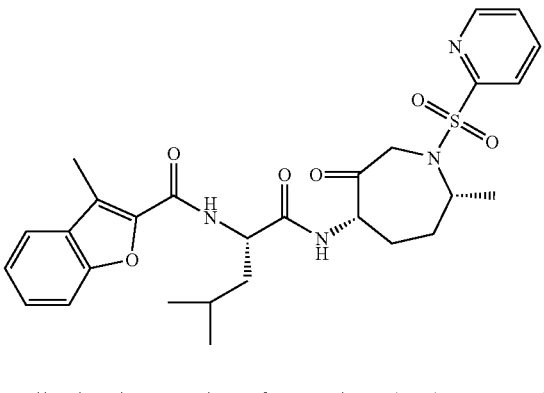

Following the procedure of Example 12 (a-m), except substituting "3-methyl-benzofuran-2-carboxylic acid" for "quinoline-6-carboxylic acid" gave the title compound: 1H NMR: 8.74(d,1H), 8.02(d,1H), 7.95(m, 1H), 7.62(d,1H), 7.54(m,3H), 7.05(d,1H), 6.93(d,1H), 5.14(m,1H), 4.78(d, 1H), 4.71(m,1H), 4.43(m,1H), 3.87(d,1H), 2.64(s,3H), 2.19 (m,2H), 1.5-1.76(m,5H), 1.0(m, 10H); Electrospray mass spec: M+H$^+$=555.2 (M+1)$^+$.

Example 16

Preparation of Thieno[3,2-b]thiophene-2-carboxylic acid {(S)-3-methyl-1-[(4S,7R)-7-methyl-3-oxo-1-(pyridine-2-sulfonyl)-azepan-4-ylcarbamoyl]-butyl}-amide

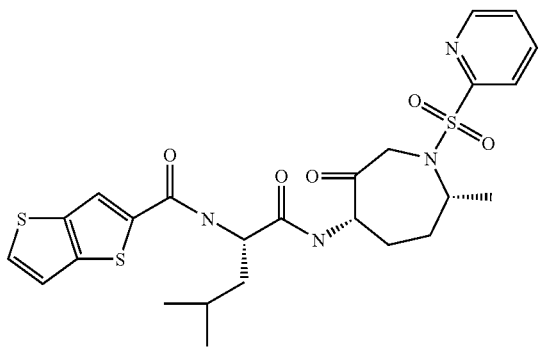

Following the procedure of Example 12 (a-m), except substituting "thieno[3,2-b]thiophene-2-carboxylic acid" for "quinoline-6-carboxylic acid" gave the title compound: 1H NMR: 8.74(d,1H), 8.02(d,1H), 7.95(m,1H), 7.78(s,1H), 7.54 (m,2H), 6.90(d,1H), 6.59(d,1H), 5.15(m,1H), 4.78(d,1H), 4.70(m,1H), 4.43(m,1H), 3.88(d,1H), 2.19(m,2H), 1.50-1.72 (m.5H), 1.00(m, 10H); Electrospray mass spec: M+H$^+$=563.2 (M+1)$^+$.

Example 17

Preparation of Quinoxaline-2-carboxylic acid {(S)-3-methyl-1-[(4S,7R)-7-methyl-3-oxo-1-(pyridine-2-sulfonyl)-azepan-4-ylcarbamoyl]-butyl}-aide

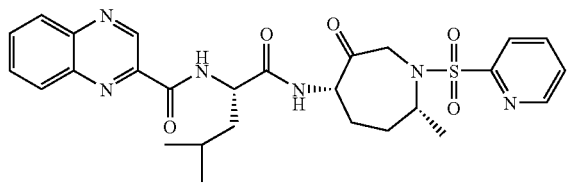

Following the procedure of Example 12 (a-m), except substituting "quinoxaline-2-carboxylic acid" for "quinoline-6-carboxylic acid" gave the title compound: 1H NMR: 9.70 (s, 1H), 8.70 (s, 1H), 8.40 (d, 1H), 8.20 (d, 2H), 7.85-8.0 (m, 1H), 7.50 (d, 1H), 7.0 (d, 1H), 5.10-5.15 (m, 1H), 4.70-4.80 (m, 2H), 4.40-4.50 (m, 1H), 3.90 (d, 1H), 2.10-2.20 (m, 2H), 1.70-1.90 (m, 3H), 1.40-1.70 (m, 2H), 0.90-1.05 (m, 9H); Electrospray mass spec: M+H$^+$=553.4.

Example 18

Preparation of Thieno[3,2-b]thiophene-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

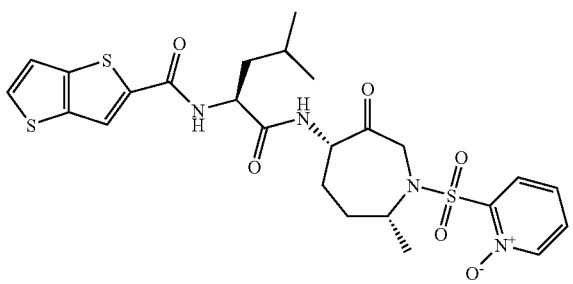

Following the procedure of Example 12 (a-m), except substituting "1-oxy-pyridine-2-sulfonyl chloride" for "pyridine-2-sulfonyl chloride" and "Thieno[3,2-b]thiophene-2-carboxylic acid" for "quinoline-6-carboxylic acid" gave the title compound: 1H NMR: 8.27 (d, 1H), 8.13 (dd, 1H), 7.55-7.41 (m, 3H), 7.28 (m, 2H), 6.95 (m, 1H), 6.65 (m, 1H), 5.03 (m, 1H), 4.89 (d, 1H), 4.68 (m, 1H), 4.36 (m, 1H), 3.98 (d, 1H), 2.30-2.12 (m, 2H), 1.74 (m, 5H), 1.06 (d, 3H), 1.00 (m, 6H); Electrospray mass spec: M+H$^+$=579.2.

Example 19

Preparation of 3-Methyl-benzofuran-2-carboxylicacid {(S)-3-methyl-1-[(4S,7R)-7-methyl-3-oxo-1-(1-oxy-pyridine-2-sulfonyl)-azepan-4-ylcarbamoyl]-butyl}-amide

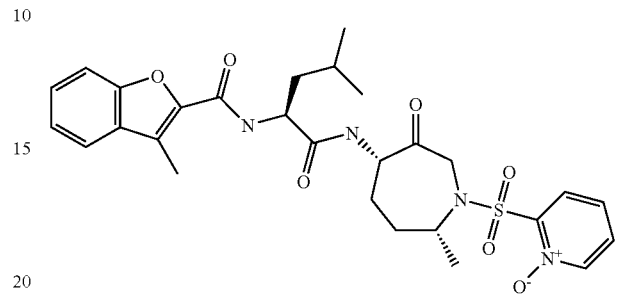

Following the procedure of Example 12 (a-m), except substituting "1-oxy-pyridine-2-sulfonyl chloride" for "pyridine-2-sulfonyl chloride" and "3-methyl-benzofuran-2-carboxylic acid" for "quinoline-6-carboxylic acid" gave the title compound: 1H NMR: 8.25 (d, 1H), 8.12 (dd, 1H), 7.61 (d, 1H), 7.50-7.39 (m, 3H), 7.30 (m, 1H), 7.05 (d, 1H), 6.95 (d, 1H), 5.03 (m, 1H), 4.89 (d, 1H), 4.71 (m, 1H), 4.36 (m, 1H), 3.98 (d, 1H), 2.62 (s, 3H), 2.25-2.12 (m, 2H), 1.89 (m, 2H), 1.75 (m, 2H), 1.63 (m, 1H), 1.53 (m, 1H), 1.05 (d, 3H), 1.00 (m, 6H); Electrospray mass spec: M+H$^+$=571.4.

Example 20

Preparation of Benzofuran-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

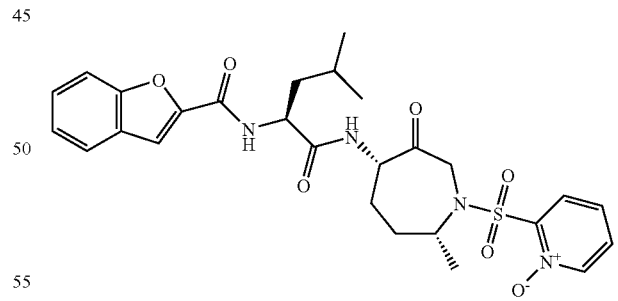

Following the procedure of Example 12 (a-m), except substituting "1-oxy-pyridine-2-sulfonyl chloride" for "pyridine-2-sulfonyl chloride" and "benzofuran-2-carboxylic acid" for "quinoline-6-carboxylic acid" gave the title compound: 1H NMR: 8.23 (d, 1H), 8.12 (dd, 1H), 7.67 (d, 1H), 7.52 (d, 1H), 7.48-7.39 (m, 3H), 7.31 (m, 1H), 7.08 (d, 1H), 6.93 (d, 1H), 5.05 (m, 1H), 4.91 (d, 1H), 4.71 (m, 1H), 4.37 (m, 1H), 3.99 (d, 1H), 2.30-2.10 (m, 2H), 1.75-1.50 (m, 6H), 1.05 (d, 3H), 1.01 (m, 6H); Electrospray mass spec: M+H$^+$=557.2.

Example 21

Preparation of Quinoline-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

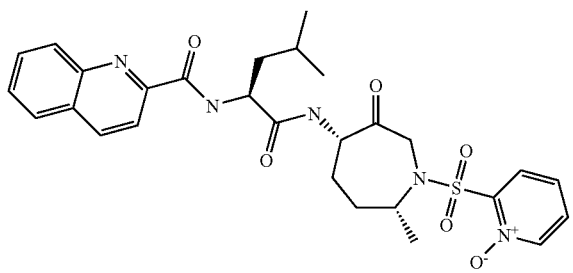

Following the procedure of Example 12 (a-m), except substituting "1-oxy-pyridine-2-sulfonyl chloride" for "pyridine-2-sulfonyl chloride" and "quinoline-2-carboxylic acid" for "quinoline-6-carboxylic acid" gave the title compound: 1H NMR: 8.65 (m, 2H), 8.49 (d, 1H), 8.23 (d, 1H), 8.11 (d, 1H), 8.05-7.95 (m, 2H), 7.80 (t, 1H), 7.46 (t, 1H), 7.39 (t, 1H), 5.02 (m, 1H), 4.85 (d, 1H), 4.75 (m, 1H), 4.39 (m, 1H), 3.93 (d, 1H), 2.30-2.08 (m, 3H), 1.97-1.80 (m, 4H), 1.70-1.52 (m, 2H), 1.07-0.99 (m, 9H); Electrospray mass spec: $M+H^+=568.2$.

Example 22

Preparation of 5,6-Difluoro-benzofuran-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

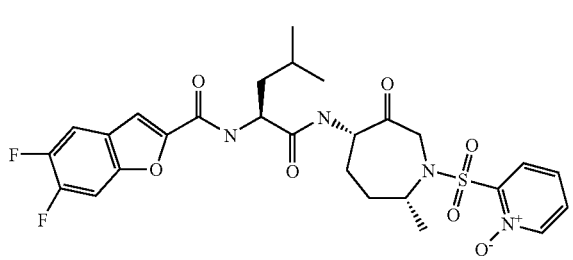

Following the procedure of Example 12 (a-m), except substituting "1-oxy-pyridine-2-sulfonyl chloride" for "pyridine-2-sulfonyl chloride" and "5,6-Difluoro-benzofuran-2-carboxylic acid" for "quinoline-6-carboxylic acid" gave the title compound: 1H NMR: 8.16 (1H, d), 8.04 (1H,d), 7.26-7.40 (m, 4H), 7.02 (1H, d), 6.89 (1H,d), 4.96 (m, 1H), 4.63 (m, 1H), 4.28 (m,1H), 2.10-2.25 (m, 2H), 1.44-1.65 (m, 3H), 1.17-1.20 (m, 3H), 0.93-0.97 (m, 9H); Liquid/Chromatgraphy/Electrospray mass spec: $M+H^+=593.23$

Example 23

Preparation of 5-Fluoro-3-methyl-benzofuran-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

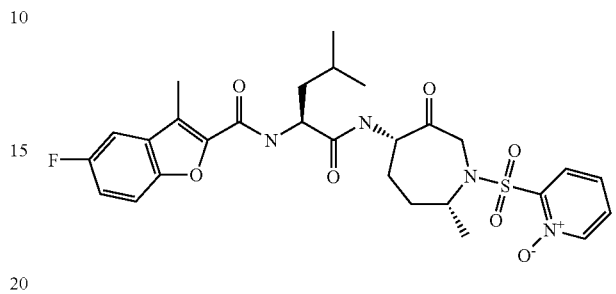

Following the procedure of Example 12 (a-m), except substituting "1-oxy-pyridine-2-sulfonyl chloride" for "pyridine-2-sulfonyl chloride" and "5-Fluoro-3-methyl-benzofuran-2-carboxylic acid" for "quinoline-6-carboxylic acid" gave the title compound: 1H NMR: 8.15 (1H, d), 8.03 (1H, d), 7.31-7.39(m, 3H), 7.18 (m, 1H), 7.17 (m, 1H), 7.07 (d, 1H), 7.06 (d, 1H), 4.85 (m, 1H), 4.62 (m, 1H), 4.31 (m, 1H), 2.05-2.22 (m, 3H), 1.44-1.66 (m, 4H), 0.92-0.99 (m, 12H); Liquid/Chromatgraphy/Electrospray mass spec: $M+H^+=589.21$

Example 24

Preparation of 5-Fluoro-benzofuran-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

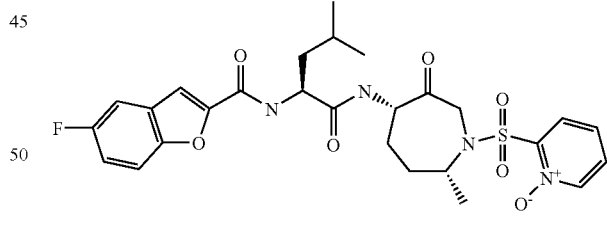

Following the procedure of Example 12 (a-m), except substituting "1-oxy-pyridine-2-sulfonyl chloride" for "pyridine-2-sulfonyl chloride" and "5-Fluoro-benzofuran-2-carboxylic acid" for "quinoline-6-carboxylic acid" gave the title compound: 1H NMR: 8.22 (1H, d), 8.12 (1H, d), 7.32-7.46 (m, 7H), 7.13 (m, 1H), 6.98 (m, 1H), 5.05 (m, 1H), 4.76 (m, 1H), 4.36 (m, 1H), 2.11-2.28 (m, 2H), 1.51-1.78 (m, 3H), 0.99-1.02 (m, 12H); Liquid/Chromatgraphy/Electrospray mass spec: $M+H^+=575.16$

Example 25

Preparation of 3-Methyl-furo[3,2-b]]pyridine-2-carboxylic acid {(S)-3-methyl-1-[(4S,7R)-7-methyl-3-oxo-1-(1-oxy-pyridine-2-sulfonyl)-azepan-4-ylcarbamoyl]-butyl}-amide

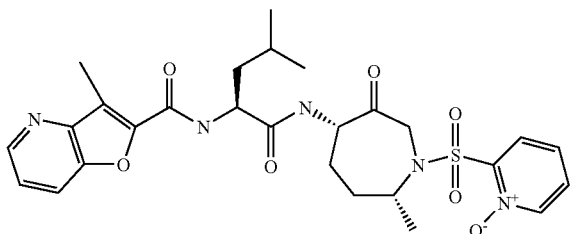

Following the procedure of Example 12 (a-m), except substituting "1-oxy-pyridine-2-sulfonyl chloride" for "pyridine-2-sulfonyl chloride" and "3-Methyl-furo[3,2-b]]pyridine-2-carboxylic acid" for "quinoline-6-carboxylic acid" gave the title compound: 1H NMR: 8.56 (1H, d), 8.16 (1H, d), 8.03 (d, 1H), 7.73 (d, 1H), 7.38 (m, 1H), 7.29-7.34 (m, 2H), 7.13 (d, 1H), 6.93 (d, 1H), 4.97 (m, 1H), 4.66 (m, 1H), 4.26 (m, 1H), 2.05-2.13 (m, 2H), 1.46-1.67 (m, 3H), 1.11-1.16 (m, 3H), 0.92-0.97 (m, 9H); Liquid/Chromatgraphy/Electrospray mass spec: M+H$^+$=572.23

Example 26

Preparation of Cyclohexanecarboxylic acid {(S)-3-methyl-1-[(4S,7R)-7-methyl-3-oxo-1-(1-oxy-pyridine-2-sulfonyl)-azepan-4-ylcarbamoyl]-butyl}-amide

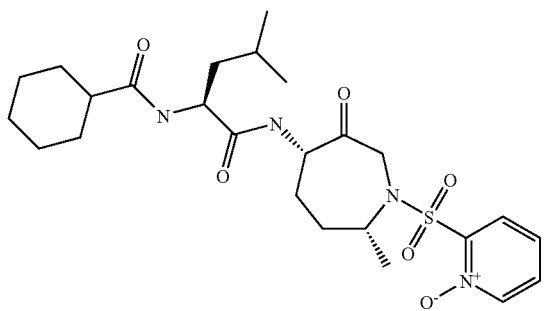

Following the procedure of Example 12 (a-m), except substituting "1-oxy-pyridine-2-sulfonyl chloride" for "pyridine-2-sulfonyl chloride" and "Cyclohexanecarboxylic acid" for "quinoline-6-carboxylic acid" gave the title compound: 1H NMR: 8.23 (d, 1H), 8.11 (dd, 1H), 7.46 (m, 1H), 7.39 (t, 1H), 6.90 (m, 1H), 5.91 (m, 1H), 4.98 (m, 1H), 4.87 (d, 1H), 4.48 (m, 1H), 4.36 (m, 1H), 3.96 (d, 1H), 2.24-2.08 (m, 2H), 1.90-1.62 (m, 10H), 1.54-1.39 (m, 3H), 1.33-1.21 (m, 3H), 1.05 (d, 3H), 0.95 (m, 6H); Electrospray mass spec: M+H$^+$=523.4.

Example 27

Preparation of (S)-2-(2-Cyclohexyl-ethanoylamino)-4-methyl-pentanoic acid [(4S,7R)-7-methyl-3-oxo-1-(1-oxy-pyridine-2-sulfonyl)-azepan-4-yl]-amide

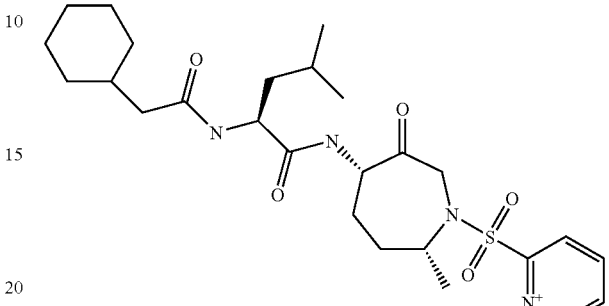

Following the procedure of Example 12 (a-m), except substituting "1-oxy-pyridine-2-sulfonyl chloride" for "pyridine-2-sulfonyl chloride" and "Cyclohexyl-acetic acid" for "quinoline-6-carboxylic acid" gave the title compound: 1H NMR: 8.23 (d, 1H), 8.11 (dd, 1H), 7.45 (t, 1H), 7.39 (t, 1H), 6.95 (m, 1H), 5.95 (m, 1H), 4.99 (m, 1H), 4.87 (d, 1H), 4.48 (m, 1H), 4.36 (m, 1H), 3.96 (d, 1H), 2.18 (m, 2H), 2.07 (m, 2H), 1.91 (m, 2H), 1.74-1.58 (m, 10H), 1.53 (m, 2H), 1.34-1.12 (m, 3H), 1.05 (d, 3H), 0.95 (m, 6H); Electrospray mass spec: M+H$^+$=537.4.

Example 28

Preparation of (S)-2-(3-Cyclohexyl-propanoylamino)-4-methyl-pentanoic acid [(4S,7R)-7-methyl-3-oxo-1-(1-oxy-pyridine-2-sulfonyl)-azepan-4-yl]-amide

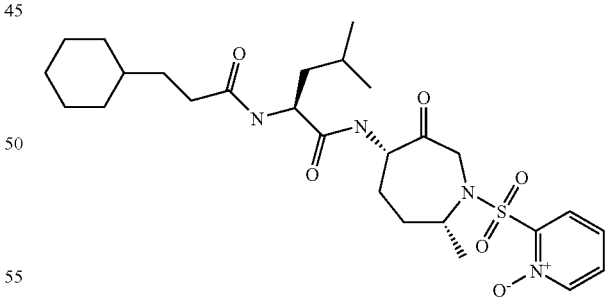

Following the procedure of Example 12 (a-m), except substituting "1-oxy-pyridine-2-sulfonyl chloride" for "pyridine-2-sulfonyl chloride" and "3-cyclohexyl-propionic acid" for "quinoline-6-carboxylic acid" gave the title compound: 1H NMR: 8.23 (d, 1H), 8.11 (dd, 1H), 7.45 (t, 1H), 7.39 (t, 1H), 6.90 (m, 1H), 5.93 (m, 1H), 4.99 (m, 1H), 4.87 (d, 1H), 4.48 (m, 1H), 4.38 (m, 1H), 3.97 (d, 1H), 2.25-2.19 (m, 4H), 1.80 (m, 2H), 1.71-1.50 (m, 12H), 1.28-1.15 (m, 4H), 1.05 (d, 3H), 0.95 (m, 6H); Electrospray mass spec: M+H$^+$=551.4.

Example 29

Preparation of (S)-2-(4-Cyclohexyl-butanoylamino)-4-methyl-pentanoic acid [(4S,7R)-7-methyl-3-oxo-1-(1-oxy-pyridine-2-sulfonyl)-azepan-4-yl]-amide

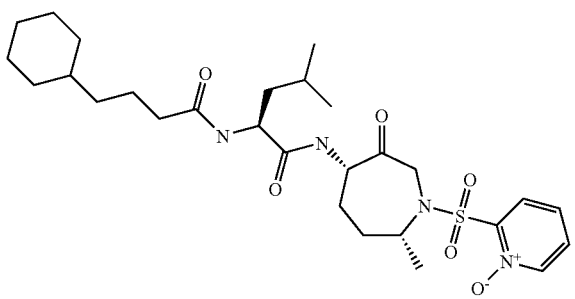

Following the procedure of Example 12 (a-m), except substituting "1-oxy-pyridine-2-sulfonyl chloride" for "pyridine-2-sulfonyl chloride" and "4-cyclohexyl-butyric acid" for "quinoline-6-carboxylic acid" gave the title compound: 1H NMR: 8.22 (d, 1H), 8.11 (dd, 1H), 7.44 (m, 1H), 7.39 (t, 1H), 6.86 (d, 1H), 5.87 (d, 1H), 5.00 (m, 1H), 4.87 (d, 1H), 4.50 (m, 1H), 4.39 (m, 1H), 3.97 (d, 1H), 2.18 (m, 4H), 1.74-1.50 (m, 12H), 1.28-1.12 (m, 6H), 1.05 (d, 3H), 0.95 (m, 6H), 0.91-0.86 (m, 2H); Electrospray mass spec: M+H$^+$=565.4.

Example 30

Preparation of (S)-2-(5-Cyclohexyl-pentanoylamino)-4-methyl-pentanoic acid [(4S,7R)-7-methyl-3-oxo-1-(1-oxy-pyridine-2-sulfonyl)-azepan-4-yl]-amide

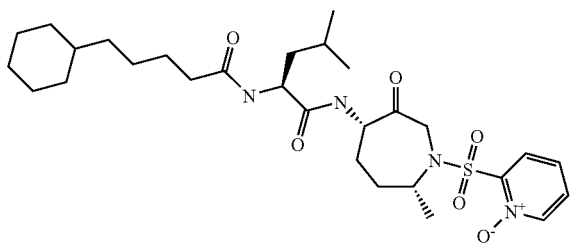

Following the procedure of Example 12 (a-m), except substituting "1-oxy-pyridine-2-sulfonyl chloride" for "pyridine-2-sulfonyl chloride" and "5-cyclohexyl-pentanoic acid" for "quinoline-6-carboxylic acid" gave the title compound: 1H NMR: 8.23 (d, 1H), 8.11 (d, 1H), 7.46 (m, 1H), 7.39 (t, 1H), 6.88 (d, 1H), 5.88 (m, 1H), 5.01 (m, 1H), 4.88 (d, 1H), 4.50 (m, 1H), 4.38 (m, 1H), 3.97 (d, 1H), 2.20 (m, 4H), 1.71-1.50 (m, 12H), 1.34 (m, 2H), 1.26-1.13 (m, 6H), 1.05 (d, 3H), 0.95 (m, 6H), 0.91-0.85 (m, 2H); Electrospray mass spec: M+H$^+$=579.4.

Example 31

Preparation of Benzofuran-2-carboxylic acid {(S)-3-methyl-1-[(4S,7R)-7-methyl-3-oxo-1-(5-trifluoromethyl-pyridine-2-sulfonyl)-azepan-4-ylcarbamoyl]-butyl}-amide

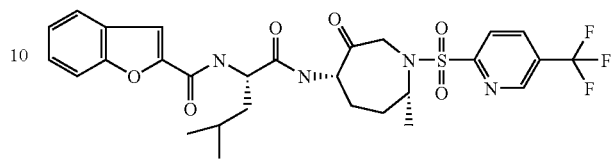

Following the procedure of Example 12 (a-m), except substituting "5-trifluoromethyl-pyridine-2-sulfonyl chloride" for "pyridine-2-sulfonyl chloride" and "benzofuran-2-carboxylic acid" for "quinoline-6-carboxylic acid" gave the title compound: 1H NMR: 8.95 (s, 1H), 8.10-8.20 (m, 2H), 7.65 (d, 1H), 7.30-7.60 (m, 3H), 7.20-7.30 (m, 1H), 7.10 (d, 1H), 6.90 (d, 1H), 5.05-5.15 (m, 1H), 4.70-4.80 (m, 2H), 4.30-4.45 (m, 1H), 3.80 (d, 1H), 2.10-2.20 (m, 2H), 1.40-1.80 (m, 5H), 0.90-1.10 (m, 9H); Electrospray mass spec: M+H$^+$=609.2.

Example 32

Preparation of 5-Fluoro-benzofuran-2-carboxylic acid {(S)-3-methyl-1-[(4S,7R)-7-methyl-3-oxo-1-(5-trifluoromethyl-pyridine-2-sulfonyl)-azepan-4-ylcarbamoyl]-butyl}-amide

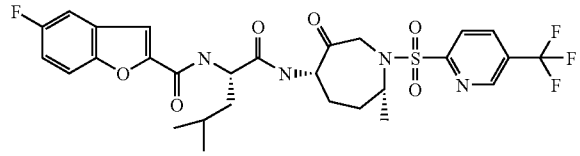

Following the procedure of Example 12 (a-m), except substituting "5-trifluoromethyl-pyridine-2-sulfonyl chloride" for "pyridine-2-sulfonyl chloride" and "5-fluoro-benzofuran-2-carboxylic acid" for "quinoline-6-carboxylic acid" gave the title compound: 1H NMR: 9.0 (s, 1H), 8.20 (d, 1H), 8.12 (d, 1H), 7.40-7.50 (m, 2H), 7.30 (d, 1H), 7.20 (d, 1H), 6.90 (d, 1H), 5.05-5.15 (m, 1H), 4.65-5.75 (m, 2H), 4.40-4.50 (m, 1H), 3.90 (d, 1H), 2.00-2.30 (m, 2H), 1.50-1.80 (m, 5H), 0.95-1.10 (m, 9H); Electrospray mass spec: M+H$^+$=627.2.

Example 33

Preparation of Thieno[3,2-b]thiophene-2-carboxylic acid {(S)-3-methyl-1-[(4S,7R)-7-methyl-3-oxo-1-(5-trifluoromethyl-pyridine-2-sulfonyl)-azepan-4-ylcarbamoyl]-butyl}-amide

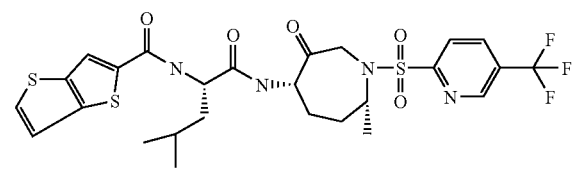

Following the procedure of Example 12 (a-m), except substituting "5-trifluoromethyl-pyridine-2-sulfonyl chloride" for "pyridine-2-sulfonyl chloride" and "thieno[3,2-b]

thiophene-2-carboxylic acid" for "quinoline-6-carboxylic acid" gave the title compound: 1H NMR: 9.0 (s, 1H), 8.10-8.20 (m, 2H), 7.80 (s, 1H), 7.50 (s, 1H), 7.25 (s, 1H), 7.0 (d, 1H), 6.80 (d, 1H), 5.0-5.10 (m, 1H), 4.60-4.80 (m, 2H), 4.40-4.50 (m, 1H), 3.90 (d, 1H), 2.10-2.20 (m, 2H), 1.50-1.80 (m, 5H), 0.9-1.0 (m, 9H); Electrospray mass spec: M+H$^+$=631.2.

Example 34

Preparation of Benzofuran-2-carboxylic acid {1-[(4S,7R)-7-methyl-3-oxo-1-(pyridine-2-sulfonyl)-azepan-4-ylcarbamoyl]-cyclohexyl}-amide

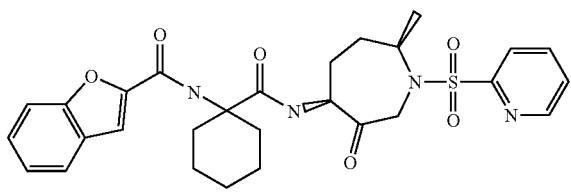

Following the procedure of Example 12 (a-m), except substituting "N-Boc-amino-cyclohexane carboxylic acid" for "Boc-L-leucine" and "benzofuran-2-carboxylic acid" for "quinoline-6-carboxylic acid" gave the title compound: 1H NMR: 8.74-8.73 (s, 1H), 8.02-7.91(m, 2H), 7.71-7.69(d, 1H), 7.58-7.28(m, 6H), 6.73(s, 1H) 5.10-5.08(m, 1H), 4.78-4.73 (d,1H), 4.44-4.13(m, 1H), 3.86-3.81(d, 1H), 2.33-2.01 (m, 6H), 1.98-1.40(m,8H), 0.99-0.97(d, 3H); Electrospray mass spec: M+H$^+$=553.4.

Example 35

Preparation of Thiophene-3-carboxylic acid {(S)-3,3-dimethyl-1-[(4S,7R)-7-methyl-3-oxo-1-(pyridine-2-sulfonyl)-azepan-4-ylcarbamoyl]-butyl}-amide

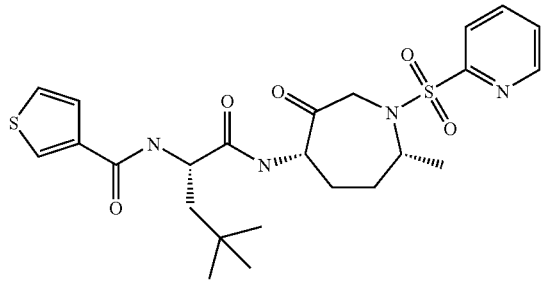

Following the procedure of Example 12 (a-m), except substituting "N-Boc-tert-butylalanine" for "Boc-L-leucine" and "thiophene-3-carboxylic acid" for "quinoline-6-carboxylic acid" gave the title compound: 1H NMR: 8.72(m, 1H), 7.96 (m, 2H), 7.48(m, 2H), 7.00(m, 3H), 6.60(m, 2H), 5.18(m, 1H), 4.67(m, 2H), 4.42(m, 1H), 3.88(m, 1H), 2.87(m, 2H), 2.22(m, 2H), 1.95(m, 1H), 1.70(m, 2H), 1.01(m, 12H); Electrospray mass spec: M+H$^+$=521.4.

Example 36

Preparation of Furan-2-carboxylic acid {(S)-3,3-dimethyl-1-[(4S,7R)-7-methyl-3-oxo-1-(pyridine-2-sulfonyl)-azepan-4-ylcarbamoyl]-butyl}-amide

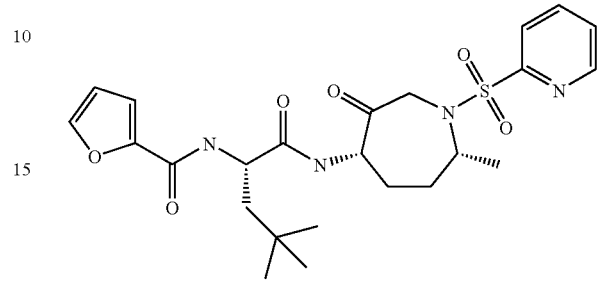

Following the procedure of Example 12 (a-m), except substituting "N-Boc-tert-butylalanine" for "Boc-L-leucine" and "furan-2-carboxylic acid" for "quinoline-6-carboxylic acid" gave the title compound: 1H NMR: 8.73(d, 1H), 7.95(m, 3H), 7.54(m,1H), 7.41(m, 1H), 7.32(m, 1H), 7.26(s, 1H), 7.01(d, 1H), 6.56(d, 1H), 5.08(m, 1H), 4.73(m, 2H), 4.43(m, 1H), 3.88(d, 1H), 2.18(m, 2H), 1.70(m, 3H), 1.04(s, 9H), 0.98(d, 3H); Electrospray mass spec: M+H$^+$=505.4.

Example 37

Preparation of Thieno[3,2-b]thiophene-2-carboxylic acid {(S)-3,3-dimethyl-1-[(4S,7R)-7-methyl-3-oxo-1-(pyridine-2-sulfonyl)-azepan-4-ylcarbamoyl]-butyl}-amide

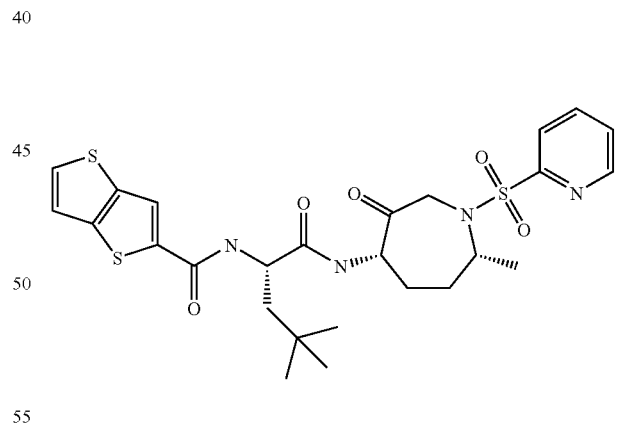

Following the procedure of Example 12 (a-m), except substituting "N-Boc-tert-butylalanine" for "Boc-L-leucine" and "thieno[3,2-b]thiophene-2-carboxylic acid" for "quinoline-6-carboxylic acid" gave the title compound: 1H NMR: 8.73 (d, 1H), 7.92(m, 3H), 7.52(m, 2H), 7.27(m, 1H), 7.09(br, 1H), 6.80(br, 1H), 5.10(m,1H), 4.77(m, 2H), 4.40(m,1H), 3.87(d, 1H), 1.90(m, 5H), 1.05(s, 9H), 0.95(d, 3H); Electrospray mass spec: M+H$^+$=577.2.

Example 38

Preparation of Benzofuran-2-carboxylic acid {(S)-2-cyclohexyl-1-[(4S,7R)-7-methyl-3-oxo-1-(pyridine-2-sulfonyl)-azepan-4-ylcarbamoyl]-ethyl}-amide

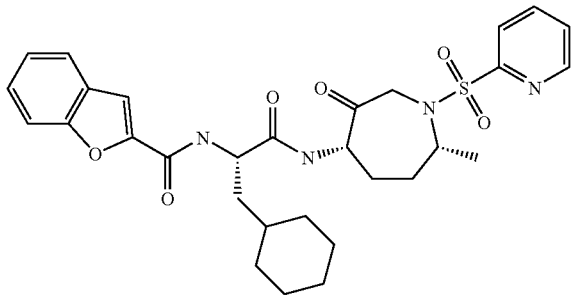

Following the procedure of Example 12 (a-m), except substituting "N-Boc-L-cyclohexylalanine" for "Boc-L-leucine" and "benzofuran-2-carboxylic acid" for "quinoline-6-carboxylic acid" gave the title compound: 1H NMR: 8.74(d, 1H), 7.96(m, 3H), 7.55(m, 1H), 7.42(m, 2H), 7.28(m, 2H), 6.77(d, 1H), 6.51(m, 1H), 5.14(m, 1H), 4.77(d, 1H), 4.69(m, 1H), 4.43(m, 1H), 3.85(d, 1H), 2.18(m, 2H), 1.85-0.98(m, 18H); Electrospray mass spec: $M+H^+=581.3$.

Example 39

Preparation of Furan-2-carboxylic acid {(S)-2-cyclohexyl-1-[(4S,7R)-7-methyl-3-oxo-1-(pyridine-2-sulfonyl)-azepan-4-ylcarbamoyl]-ethyl}-amide

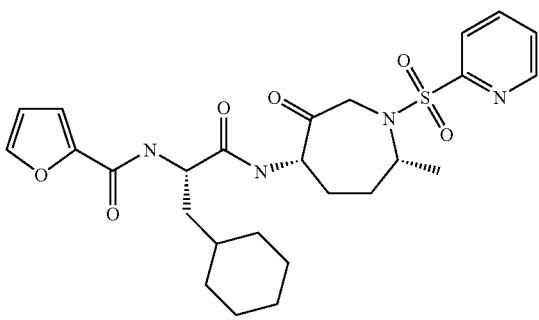

Following the procedure of Example 12 (a-m), except substituting "N-Boc-L-cyclohexylalanine" for "Boc-L-leucine" and "furan-2-carboxylic acid" for "quinoline-6-carboxylic acid" gave the title compound: 1H NMR: 8.73(d, 1H), 7.62(m, 2H), 7.53(m, 2H), 7.13(s, 1H), 6.94(d, 1H), 6.77(d, 1H), 6.51(m, 1H), 5.18(m, 1H), 4.77(d, 1H), 4.63(m,1H), 4.25(m, 1H), 3.86(d, 1H), 2.10(m, 2H), 1.87-0.93(m, 18H); Electrospray mass spec: $M+H^+=531.2$.

Example 40

Preparation of Thiophene-3-carboxylic acid {(S)-2-cyclohexyl-1-[(4S,7R)-7-methyl-3-oxo-1-(pyridine-2-sulfonyl)-azepan-4-ylcarbamoyl]-ethyl}-amide

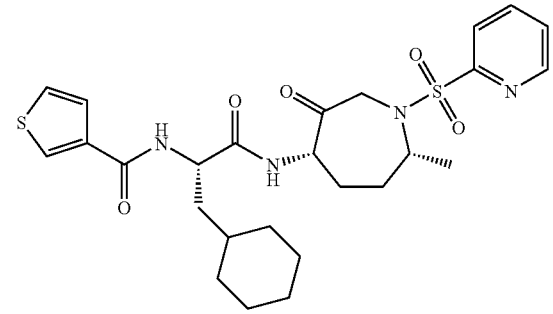

Following the procedure of Example 12 (a-m), except substituting "N-Boc-L-cyclohexylalanine" for "Boc-L-leucine" and "thiophene-3-carboxylic acid" for "quinoline-6-carboxylic acid" gave the title compound: 1H NMR: 8.74(d, 1H), 8.00(m, 2H), 7.66(d,1H), 7.46(m, 3H), 7.28(d, 1H), 6.90(d, 1H), 5.14(m, 1H), 4.43(m, 1H), 3.82(d,1H), 2.16(m, 2H), 1.90-0.96(m, 18H); Electrospray mass spec: $M+H^+=547.2$.

Example 41

Preparation of 3-Methyl-furo[3,2-b]-pyridine-2-carboxylic acid {(S)-2-cyclohexyl-1-[(4S,7R)-7-methyl-3-oxo-1-(pyridine-2-sulfonyl)-azepan-4-ylcarbamoyl]-ethyl}-amide

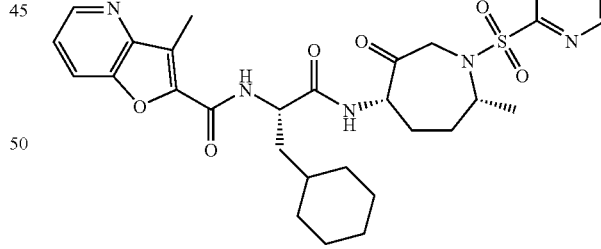

Following the procedure of Example 12 (a-m), except substituting "N-Boc-L-cyclohexylalanine" for "Boc-L-leucine" and "3-Methyl-furo[3,2-b]-pyridine-2-carboxylic acid" for "quinoline-6-carboxylic acid" gave the title compound: 1H NMR: 8.75(d, 1H), 7.98(m, 2H), 7.55(m, 1H), 7.40(m, 2H), 7.33(m, 1H), 6.75(d, 1H), 6.50(m, 1H), 5.09(m,1H), 4.79(d, 1H), 4.68(m, 1H), 4.47(m, 1H), 3.87(d, 1H), 2.55(s,3H), 2.17(m, 1H), 1.93-0.93(m, 19H); Electrospray mass spec: $M+H^+=596.4$.

Example 42

Preparation of (2R,4aR,8aR)-Octahydro-benzo[1,4]dioxine-2-carboxylic acid [(S)-1-((4S,7R)-1-methanesulfonyl-7-methyl-3-oxo-azepan-4-ylcarbamoyl)-3-methyl-butyl]-amide

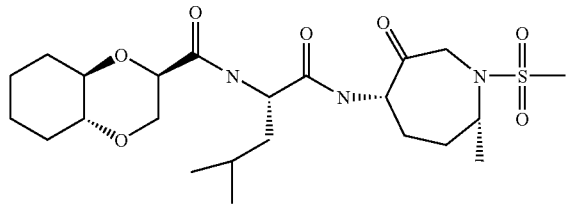

Following the procedure of Example 12 (a-m), except substituting "methyl sulfonylchloride" for "pyridine-2-sulfonyl chloride" and "(2R,4aR,8aR)-Octahydro-benzo[1,4]dioxine-2-carboxylic acid" for "quinoline-6-carboxylic acid" gave the title compound: 1H NMR: 7.65 (d, 1H), 5.0 (d, 1H), 4.45-4.50 (m, 1H), 4.30-4.35 (m, 1H), 4.25 (d, 1H), 4.0 (d, 1H), 3.80 (d, 1H), 3.50 (t, 1H), 3.30 (s, 2H), 3.15-3.2 (m, 1H), 3.30 (s, 1H), 1.3-2.2 (m, 15H), 1.20 (d, 3H), 0.0 (t, 6H); Electrospray mass spec: M+H$^+$=502.4.

Example 43

Preparation of Furan-2-carboxylic acid [(S)-2-cyclohexyl-1-((4S,7R)-7-methyl-3-oxo-1-propyl-azepan-4-ylcarbamoyl)-ethyl]-amide

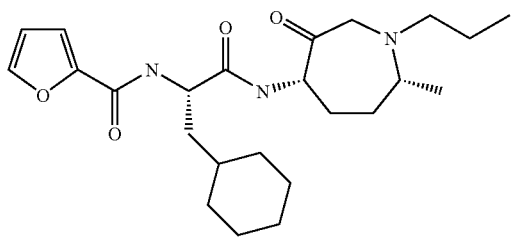

a. [(S)-2-Cyclohexyl-1-((3S,4S,7R)-3-hydroxy-7-methyl-1-propyl-azepan-4-ylcarbamoyl)-ethyl]-carbamic acid tert-butyl ester

[(S)-2-Cyclohexyl-1-((3S,4S,7R)-3-hydroxy-7-methyl-azepan-4-ylcarbamoyl)-ethyl]-carbamic acid-tert-butyl ester (Example 12 a-e, except substituting "Boc-L-cyclohexylalanine" for "Boc-L-leucine", 1.5 g, 3.78 mmol) was dissolved in CH$_2$Cl$_2$(30 mL), then propionaldehyde (0.41 mL, 5.67 mmol) was added. Then, sodium borohydride (1.6 g, 7.56 mmol) was added and the reaction mixture was stirred at RT for 1 h. The reaction mixture was concentrated in vacuo by rotary evaporation, then the filtrate (silica gel, 14% MeOH/CH$_2$Cl$_2$) to yield the title compound as a white solid (84%, 1.4 g): Electrospray mass spec: M+H$^+$=440.4.

b. (S)-2-Amino-3-cyclohexyl-N-((3S,4S,7R)-3-hydroxy-7-methyl-1-propyl-azepan-4-yl)-propionamide HCl in dioxane (4.0 M, 15 ml) was added to a stirred solution of [(S)-2-Cyclohexyl-1-((3S,4S,7R)-3-hydroxy-7-methyl-1-propyl-azepan-4-ylcarbamoyl)-ethyb.1]-carbamic acid tert-butyl ester (1.4 g, 3.0 mmol) in MeOH (5 ml). The reaction mixture was stirred for 2 h at RT, then was concentrated in vacuo by rotary evaporation and was used in the next reaction without further purification (1.4 g).

c. Furan-2-carboxylic acid [(S)-2-cyclohexyl-1-((3S,4S,7R)-3-hydroxy-7-methyl-1-propyl-azepan-4-ylcarbamoyl)-ethyl]-amide 1-(3-Dimethylaminopropyl)-3-ethylcarbodiimide (0.10 g, 0.53 mmol) was added to a solution of furan-2-carboxylic acid (0.059 g, 0.53 mmol), (S)-2-Amino-3-cyclohexyl-N-((3S,4S,7R)-3-hydroxy-7-methyl-1-propyl-azepan-4-yl)-propionamide (0.15 g, 0.36 mmol), 4-methylmorpholine (0.14 g, 0.16 ml, 1.44 mmol), hydroxybenztriazole (0.071 g, 0.53 mmol) in DMF (2.0 ml) and was stirred at RT overnight. The reaction mixture was then warmed to RT and was stirred overnight. The reaction mixture was diluted with EtOAc (30 ml), washed with H$_2$O, brine, dried with magnesium sulfate, filtered, concentrated in vacuo by rotary evaporation, and chromatographed (silica gel, 2.5% MeOH/CH$_2$Cl$_2$) to yield the title compound (0.12 g, 76%): Electrospray mass spec: M+H$^+$=434.2.

d. Furan-2-carboxylic acid [(S)-2-cyclohexyl-1-((4S,7R)-7-methyl-3-oxo-1-propyl-azepan-4-ylcarbamoyl)-ethyl]-amide Sulfur trioxide-pyridine complex (0.0.35 g, 2.2 mmol) was added to a solution of Furan-2-carboxylic acid [(S)-2-cyclohexyl-1-((3S,4S,7R)-3-hydroxy-7-methyl-1-propyl-azepan-4-ylcarbamoyl)-ethyl]-amide (0.19 g, 0.44 mmol) in DMSO (4.0 ml) and triethylamine (0.61 ml, 4.4 mmol) was stirred at RT for 1 h. The reaction mixture was diluted with water, then was extracted with EtOAc. Then, the organic layer was was extracted with brine. The combined organics were dried with magnesium sulfate, filtered, concentrated in vacuo, and purified by column chromatography (3% methanol/methylene chloride) gave the title compound (0.15 mg, 79%): 1H NMR: 7.44(s, 1H), 7.11(d, 1H), 7.04(d, 1H), 6.92(d, 1H), 6.49(d, 1H), 5.29(m, 1H), 4.69(m, 1H), 3.40(d, 1H), 3.08(m, 2H), 2.51(m, 2H), 1.88-0.81(m, 29H); Electrospray mass spec: M+H$^+$=432.2.

Example 44

Preparation of Thiophene-3-carboxylic acid [(S)-2-cyclohexyl-1-((4S,7R)-7-methyl-3-oxo-1-propyl-azepan-4-ylcarbamoyl)-ethyl]-amide

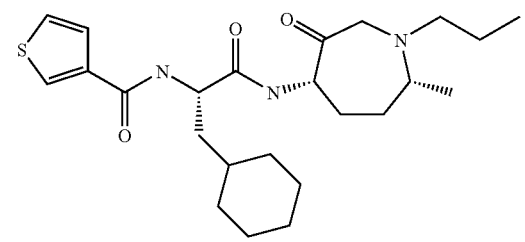

Following the procedure of Example 43 (a-d), except substituting "thiophene-3-carboxylic acid" for "furan-2-carboxylic acid" gave the title compound: 1H NMR: 7.62(d, 1H), 7.40(d, 1H), 7.04(d, 1H), 6.80(d, 1H), 6.45(d,1H), 5.27(m, 1H), 4.66(m,1H), 3.44(d, 1H), 3.09(m, 2H), 2.54(m, 2H), 1.87-0.87(m, 29H); Electrospray mass spec: M+H⁺=448.4.

Example 45

Preparation of Benzofuran-2-carboxylic acid [(S)-2-cyclohexyl-1-((4S,7R)-7-methyl-3-oxo-1-propyl-azepan-4-ylcarbamoyl)-ethyl]-amide

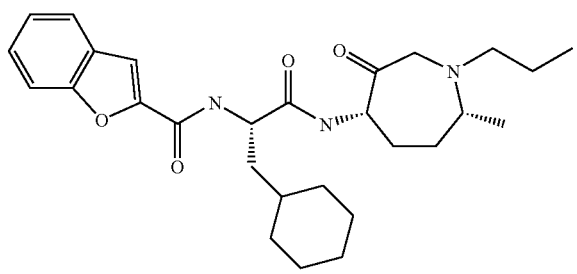

Following the procedure of Example 43 (a-d), except substituting "benzofuran-2-carboxylic acid" for "furan-2-carboxylic acid" gave the title compound: 1H NMR: 7.98(d, 1H), 7.45(m, 2H), 7.27(s, 2H), 6.90(d, 1H), 6.50(d, 1H), 5.28(m, 1H), 4.67(m, 1H), 3.40(d, 1H), 3.06(m, 2H), 2.56(m, 2H), 1.88-0.80(m, 29H); Electrospray mass spec: M+H⁺=482.4.

Example 46

Preparation of 1-(3-Cyclohexyl-propanoylamino)-cyclohexanecarboxylic acid ((4S,7R)-1-cyclohexyl-methyl-7-methyl-3-oxo-azepan-4-yl)-amide

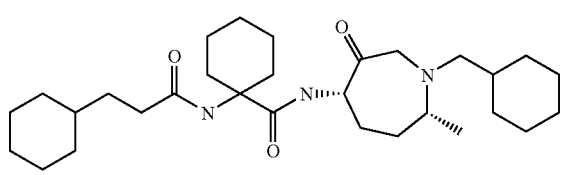

Following the procedure of Example 43 (a-d), except substituting "N-Boc-amino-cyclohexane carboxylic acid" for "Boc-L-cyclohexylalanine" and "cyclohexanecarbaldehyde" for "propionaldehyde" and "cyclohexyl-3-propionic acid" for "furan-2-carboxylic acid" gave the title compound: 1H NMR: 7.40 (d, 1H), 7.15 (d, 1H), 5.10-5.20 (m, 1H), 3.40 (d, 1H), 3.00-3.10 (m, 2H), 0.80-2.40 (m, 45H); Electrospray mass spec: M+H⁺=502.4.

Example 47

Preparation of Benzofuran-2-carboxylic acid [1-((4S, 7R)-1-cyclohexylmethyl-7-methyl-3-oxo-azepan-4-ylcarbamoyl)-cyclohexyl]-amide

Following the procedure of Example 43 (a-d), except substituting "N-Boc-amino-cyclohexane carboxylic acid" for "Boc-L-cyclohexylalanine" and "cyclohexanecarbaldehyde" for "propionaldehyde" and "benzofuran-2-carboxylic acid" for "furan-2-carboxylic acid" gave the title compound: 1H NMR: 7.60 (d, 1H), 7.30-7.50 (m, 3H), 7.15-7.25 (m, 2H), 6.60 (s, 1H), 5.00-5.10 (m, 1H), 3.35 (d, 1H), 2.90-3.05 (m, 3H), 1.05-2.40 (m, 26H), 0.80 (d, 3H); Electrospray mass spec: M+H⁺=508.4.

Example 48

Preparation of Benzofuran-2-carboxylic acid [(S)-3-methyl-1-((4S,7R)-7-methyl-3-oxo-1-propyl-azepan-4-ylcarbamoyl)-butyl]-amide

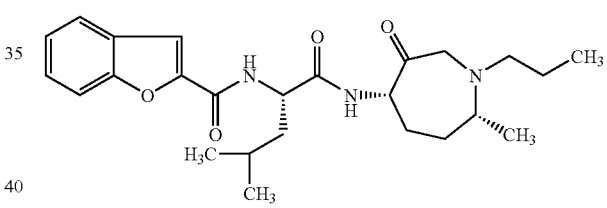

Following the procedure of Example 43 (a-d), except substituting "N-Boc-L-leucine" for "Boc-L-cyclohexylalanine" and "benzofuran-2-carboxylic acid" for "furan-2-carboxylic acid" gave the title compound: Electrospray mass spec: M+H⁺=442.05 (M+H).

Example 49

Preparation of (2R,5S)-5-((S)-2-tert-Butoxycarbonylamino-4-methyl-pentanoylamino)-2-methyl-6-oxo-azepane-1-carboxylic acid benzyl ester

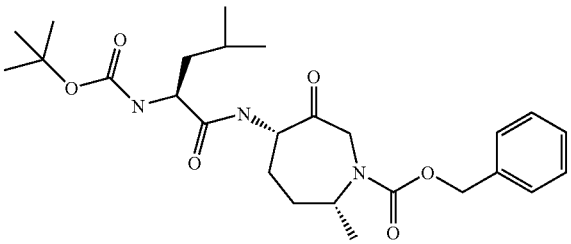

Following the procedure of Example 12 (m), except substituting "(2R,5S)-5-((S)-2-tert-Butoxycarbonylamino-4-methyl-pentanoylamino)-2-methyl-6-hydroxy-azepane-1-carboxylic acid benzyl ester" for "quinoline-6-carboxylic acid {(S)-3-methyl-1-[(4S,7R)-7-methyl-3-hydroxy-1-(pyridine-2-sulfonyl)-azepan-4-ylcarbamoyl]-butyl}-amide gave the title compound: 1H NMR: 7.40-7.35 (m, 5H), 5.26 (m, 1H), 5.13 (dd, 1H), 4.91-4.78 (m, 2H), 4.47 (m, 1H), 4.12 (m, 1H), 3.64 (dd, 1H), 2.32 (m, 1H), 2.10 (m, 1H), 1.70-1.52 (m, 5H), 1.45 (s, 9H), 1.12 (d, 3H), 0.96 (s, 3H), 0.94 (s, 3H); Electrospray mass spec: M+H$^+$=512.2.

Example 50

Preparation of Benzofuran-2-carboxylic acid {(S)-3-methyl-1-[(4S,7R)-7-methyl-1-(1-morpholin-4-yl-methanoyl)-3-oxo-azepan-4-ylcarbamoyl]-butyl}-amide

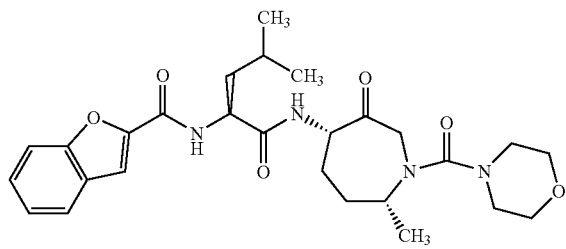

Following the procedure of Example 12 (a-m), except "morpholine-4-carbonyl chloride" for "pyridine-2-sulfonyl chloride" and "benzofuran-2-carboxylic acid" for "quinoline-6-carboxylic acid" gave the title compound: 1H NMR: 7.62 (d, 1H), 7.51 (d, 1H), 7.38 (m, 1H), 7.22 (m, 1H), 7.11 (d, 1H), 4.69 (m, 1H), 3.87 (m, 1H), 3.51 (m, 2H), 3.21 (m, 2H), 3.07 (m, 1H), 2.14 (m, 1H), 1.66-1.85 (m, 3H), 1.26 (m, 3H), 1.17 (m, 3H), 0.94 (m, 6H); Liquid/Chromatgraphy/Electrospray mass spec: M+H$^+$=513.21

Example 51

Preparation of (S)-2-(3-Cyclohexyl-propanoylamino)-4-methyl-pentanoic acid [(4S,7R)-7-methyl-1-(1-morpholin-4-yl-methanoyl)-3-oxo-azepan-4-yl]-amide

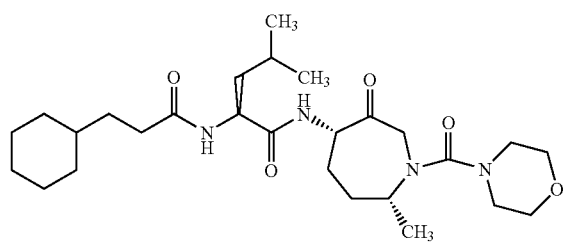

Following the procedure of Example 12 (a-m), except "morpholine-4-carbonyl chloride" for "pyridine-2-sulfonyl chloride" and "cyclohexyl-3-propionic acid" for "quinoline-6-carboxylic acid" gave the title compound: 1H NMR: 6.94 (d, 1H), 5.85 (m, 1H), 4.59 (m, 1H), 4.40 (m, 1H), 3.61 (m, 4H), 3.19 (m, 2H), 3.10 (m, 2H), 2.02-2.28 (m, 4H), 1.77 (m, 1H), 1.50-1.69 (m, 6H), 1.32-1.46 (m, 4H), 1.25 (d, 2H), 1.01-1.19 (m, 4H), 0.87 (m, 6H); Liquid/Chromatgraphy/Electrospray mass spec: M+H$^+$=507.27.

Example 52

Preparation of (2R,5S)-5-{(S)-2-[(1-Benzofuran-2-yl-methanoyl)-amino]-4-methyl-pentanoylamino}-2-methyl-6-oxo-azepane-1-carboxylic acid (tetrahydro-pyran-4-yl)-amide

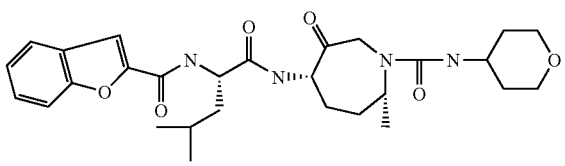

Following the procedure of Example 12 (a-m), except "tetrahydro-pyran-4-amino-carbonyl chloride" for "pyridine-2-sulfonyl chloride" and "benzofuran-2-carboxylic acid" for "quinoline-6-carboxylic acid" gave the title compound: 1H NMR: 7.65 (d, 1H), 7.40-7.50 (m, 3H), 7.20-7.30 (m, 1H), 7.05 (d, 1H), 6.90 (d, 1H), 5.00 (d, 1H), 4.80-4.90 (m, 1H), 4.65-4.80 (m, 1H), 4.50 (d, 1H), 3.85-4.00 (m, 4H), 3.40-3.50 (m, 5H), 2.30-2.40 (m, 1H), 1.90-2.05 (m, 3H), 1.40-1.75 (m, 5H), 1.20 (d, 3H), 1.00 (d, 6H); Electrospray mass spec: M+H$^+$=527.4.

Example 53

Preparation of (S)-2-{[1-((2R,5S)-5-{(S)-2-[(1-Benzofuran-2-yl-methanoyl)-amino]-4-methyl-pentanoylamino}-2-methyl-6-oxo-azepan-1-yl)-methanoyl]-amino}-4-methyl-pentanoic acid methyl ester

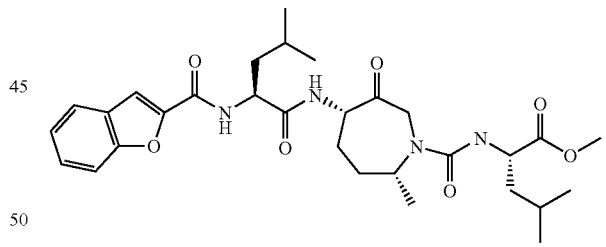

a. (S)-2-({1-[(2R,5S)-5-((S)-2-tert-Butoxycarbonylamino-4-methyl-pentanoylamino)-2-methyl-6-hydroxy-azepan-1-yl]-methanoyl}-amino)-4-methyl-pentanoic acid methyl ester

[(S)-3-Methyl-1-((4S,7R)-7-methyl-3-hydroxy-azepan-4-ylcarbamoyl)-butyl]-carbamic acid tert-butyl ester (Example 12a-i, 500 mg, 1.4 mmol) was dissolved in THF (7 ml), then (S)-(−)-2-isocyanato-4-methylvaleric acid methyl ester (180 mg, 1.05 mmol) was added and the reaction mixture was stirred at RT for 2 h. The reaction mixture was concentrated in vacuo by rotary evaporation, and chromatographed (silica gel, 1% to 2% MeOH/CH$_2$Cl$_2$) to yield the title compound as a white solid (91%, 506 mg): LC/Electrospray mass spec: M+H$^+$=529.4.

b. (S)-2-({1-[(2R,S)-5-((S)-2-Amino-4-methyl-pentanoylamino)-2-methyl-6-hydroxy-azepan-1-yl]-methanoyl}-amino)-4-methyl-pentanoic acid methyl ester 4.0 M HCl in dioxane (8 ml) was added to a stirred solution (S)-2-({1-[(2R,5S)-5-((S)-2-tert-Butoxycarbonylamino-4-methyl-pentanoylamino)-2-methyl-6-hydroxy-azepan-1-yl]-methanoyl}-amino)-4-methyl-pentanoic acid methyl ester (490 mg, 0.93 mmol) in MeOH (8 ml). The reaction mixture was stirred for 2.5 h at RT, then was concentrated in vacuo by rotary evaporation and was used in the next reaction without further purification (430 mg).

c. (S)-2-{[1-((2R,5S,6S)-5-{(S)-2-[(1-Benzofuran-2-yl-methanoyl)-amino]-4-methyl-pentanoylamino}-6-hydroxy-2-methyl-azepan-1-yl)-methanoyl]-amino}-4-methyl-pentanoic acid methyl ester 1-(3-Dimethylaminopropyl)-3-ethylcarbodiimide (214 g, 1.12 mmol) was added to a solution of benzofuran-2-carboxylic acid (166 g, 1.02 mmol), (S)-2-({1-[(2R,5S)-5-((S)-2-Amino-4-methyl-pentanoylamino)-2-methyl-6-hydroxy-azepan-1-yl]-methanoyl}-amino)-4-methyl-pentanoic acid methyl ester (430 mg, 0.93 mmol), diisopropylethylamine (240 mg, 0.32 ml, 1.86 mmol), hydroxybenztriazole (151 mg, 1.12 mmol) in DMF (5 ml) and was stirred at RT overnight. The reaction mixture was stirred overnight. The reaction mixture was diluted with EtOAc (30 ml), washed with cold aq. 1N HCl, aq. sat. NaHCO₃, and brine, and then dried with magnesium sulfate, filtered, concentrated in vacuo by rotary evaporation, and chromatographed (silica gel, 2% to 3% MeOH/CH₂Cl₂) to yield the title compound (478 mg, 84% for two steps): electrospray MS: 572.4 d. (S)-2-{[1-((2R,5S,6S)-5-{(S)-2-[(1-Benzofuran-2-yl-methanoyl)-amino]-4-methyl- -6-oxo-2-methyl-azepan-1-yl)-methanoyl]-amino}-4-methyl-pentanoic acid methyl ester Dess-Martin periodinane (500 mg, 1.18 mmol) was added to a solution of (S)-2-{[1-((2R,5S,6S)-5-{(S)-2-[(1-Benzofuran-2-yl-methanoyl)-amino]-4-methyl-pentanoylamino}-6-hydroxy-2-methyl-azepan-1-yl)-methanoyl]-amino}-4-methyl-pentanoic acid methyl ester (450 mg, 0.79 mmol) in CH₂Cl₂ (16 ml) and was stirred at RT for 3 h. The solution was washed with 10% aq. Na₂S₂O₃, aq. sat. NaHCO₃, and brine. Purification by column chromatography (silica gel, 1% to 2% MeOH/CH₂Cl₂) gave the title compound (405 mg, 90%): 1H NMR (400 MHz, CDCl3): δ 7.69 (d, 1H), 7.54 (d, 1H), 7.49 (s, 1H), 7.44 (t, 1H), 7.31(t, 1H), 7.08 (d, 1H), 6.91 (d, 1H), 5.03-4.95 (m, 2H), 4.84 (q, 1H), 4.71-4.62 (m, 1H), 4.57 (q, 1H), 4.10-4.02 (m, 1H), 3.77 (s, 3H), 3.57 (d, 1H), 2.46-2.36 (m, 1H), 2.07-1.99(m, 1H), 1.82-1.41 (m, 8H), 1.25 (d, 3H), 1.02 (d, 12H); Electrospray mass spec: M+H⁺=571.4.

Example 54

Preparation of (S)-2-{[1-((2R,5S)-5-{(S)-2-[(1-Benzofuran-2-yl-methanoyl)-amino]-4-methyl-pentanoylamino}-2-methyl-6-oxo-azepan-1-yl)-methanoyl]-amino}-4-methyl-pentanoic acid

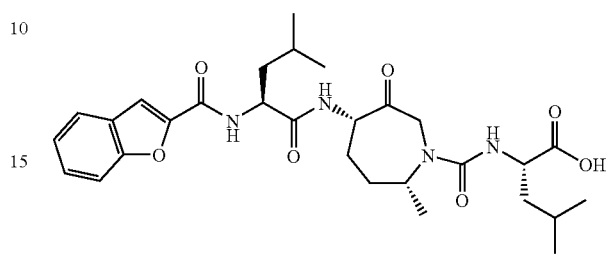

a. (S)-2-{[1-((2R,5S,6S)-5-((S)-2-[(1-Benzofuran-2-yl-methanoyl)-amino]-4-methyl-pentanoylamino}-6-oxo-2-methyl-azepan-1-yl)-methanoyl]-amino}-4-methyl-pentanoic acid methyl ester (58 mg, 0.1 mmol) was dissolved in MeOH (1.0 ml) and H₂O (0.5 ml), then potassium carbonate (28 mg, 0.2 mmol) was added and the reaction mixture was stirred at RT for 20 h. The reaction mixture was acidified with cold aq. 1N HCl, extracted with CH₂Cl₂, washed with brine, and then dried with magnesium sulfate. Following filtration, concentration by rotary evaporation, and purification by column chromatography (silica gel, 2% MeOH/CH₂Cl₂ to 5% MeOH/CH₂Cl₂), the title compound (28 mg, 50%) was obtained as a white solid: 1H NMR (400 MHz, DMSO-d₆): δ 8.65 (d, 1H), 8.11 (d, 1H), 7.79 (d, 1H), 7.69 (d, 1H), 7.63(s, 1H), 7.48 (t, 1H), 7.35 (t, 1H), 6.60 (br s, 1H), 4.67-4.48 (m, 3H), 4.24 (m, 1H), 4.11 (m, 1H), 3.62-3.49 (m, 2H), 2.01-1.09 (m, 10H), 1.09 (d, 3H), 0.93-0.81 (m, 12H); Electrospray mass spec: M+H⁺=557.4.

Example 55

Preparation of (S)-2-{[1-(4-{(S)-2-[(1-Benzofuran-2-yl-methanoyl)-amino]-4-methyl-pentanoylamino}-3-oxo-azepan-1-yl)-methanoyl]-amino}-4-methyl-pentanoicacid methyl ester

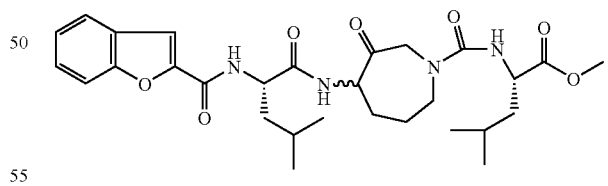

Following the procedure of Example 53 (a-d), except substituting "(3S,4S)-4-Amino-3-hydroxy-azepane-1-carboxylic acid benzyl ester (Marquis, R. J. Med. Chem., 2001)" for "(2R,5S,6S)-5-Amino-6-hydroxy-2-methyl-azepane-1-carboxylic acid benzyl ester" the title compound was obtained: 1H NMR (400 MHz, CDCl₃): δ7.69 (d, 1H), 7.54 (d, 1H), 7.49 (s, 1H), 7.44 (t, 1H), 7.31 (t, 1H), 7.08 (d, 1H), 6.96 (d, 1H), 5.06-4.97 (m, 2H), 4.77-4.64 (m, 1H), 4.55 (m, 1H), 3.93 (d, 1H), 3.77 (s, 3H), 3.61 (d, 1H), 2.93 (t, 1H), 2.28 (m, 1H), 2.09 (m, 1H), 1.88 (m, 1H), 1.81-1.24 (m, 7H), 1.01 (d, 12H); Electrospray mass spec: M+H⁺=557.4.

Example 56

Preparation of (S)-2-([1-(4-{(S)-2-[(1-Benzofuran-2-yl-methanoyl)-amino]-4-methyl-pentanoylamino}-3-oxo-azepan-1-yl)-methanoyl]-amino}-4-methyl-pentanoic acid

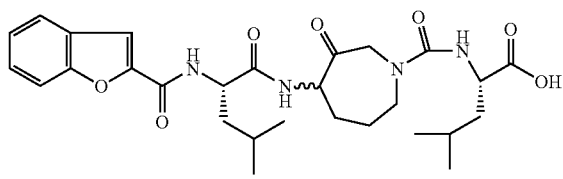

Following the procedure of Example 54 (a), except substituting "(S)-2-{[1-(4-{(S)-2-[(1-Benzofuran-2-yl-methanoyl)-amino]-4-methyl-pentanoylamino}-3-oxo-azepan-1-yl)-methanoyl]-amino}-4-methyl-pentanoic acid methyl ester" for (S)-2-{[1-((2R,5S,6S)-5-{(S)-2-[(1-Benzofuran-2-yl-methanoyl)-amino]-4-methyl-pentanoylamino}-6-oxo-2-methyl-azepan-1-yl)-methanoyl]-amino}-4-methyl-pentanoic acid methyl ester" the title compound was obtained: 1H NMR (400 MHz, CDCl$_3$): δ7.69 (d, 1H), 7.58-7.37 (m, 3H), 7.32 (t, 1H), 7.06 (br s, 1H), 5.00 (br s, 1H), 4.79-4.63 (m, 2H), 4.58-4.46 (m, 1H), 4.35-4.22 (m, 1H), 3.61-3.22 (m, 2H), 2.21-0.69 (m, 24H); Electrospray mass spec: M+H$^+$ =543.4.

Example 57

Preparation of (S)-4-Methyl-2-{[1-((2R,5S)-2-methyl-5-{(S)-4-methyl-2-[(1-quinolin-8-yl-methanoyl)-amino]-pentanoylamino}-6-oxo-azepan-1-yl)-methanoyl]-amino}-pentanoic acid methyl ester

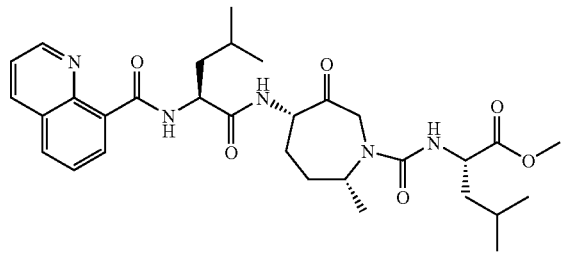

Following the procedure of Example 53 (a-d), except substituting "Quinoline-8-carboxylic acid" for "Benzofuran-2-carboxylic acid" the title compound was obtained: 1H NMR (400 MHz, CDCl$_3$): δ11.70 (d, 1H), 8.98 (d, 1H), 8.87 (d, 1H), 8.32 (d, 1H), 8.01 (d, 1H), 7.71 (t, 1H), 7.53 (dd, 1H), 7.34 (d, 1H), 5.05-4.74 (m, 4H), 4.61-4.52 (m, 1H), 4.12-4.01 (m, 1H), 3.76 (s, 3H), 3.54 (d, 1H), 2.50-2.33 (m, 1H), 2.09-1.97 (m, 1H), 1.93-1.39 (m, 8H), 1.22 (d, 3H), 1.05-0.92 (m, 12H); Electrospray mass spec: M+H$^+$=582.4.

Example 58

Preparation of (S)-4-Methyl-2-{[1-((2R,5S)-2-methyl-5-{(S)-4-methyl-2-[(1-quinolin-8-yl-methanoyl)-amino]-pentanoylamino}-6-oxo-azepan-1-yl)-methanoyl]-amino}-pentanoic acid

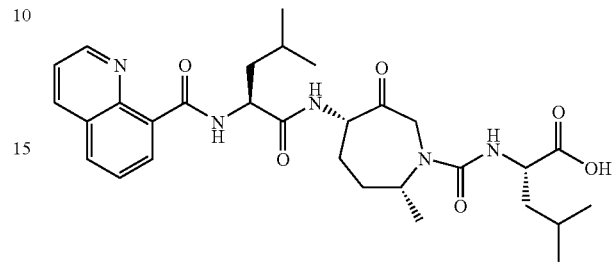

Following the procedure of Example 54 (a), except substituting "(S)-4-Methyl-2-{[1-((2R,5S)-2-methyl-5-{(S)-4-methyl-2-[(1-quinolin-8-yl-methanoyl)-amino]-pentanoylamino}-6-oxo-azepan-1-yl)-methanoyl]-amino}-pentanoic acid methyl ester" for (S)-2-{[1-((2R,5S,6S)-5-{(S)-2-[(1-Benzofuran-2-yl-methanoyl)-amino]-4-methyl-pentanoylamino}-6-oxo-2-methyl-azepan-1-yl)-methanoyl]-amino}-4-methyl-pentanoic acid methyl ester" the title compound was obtained: 1H NMR (400 MHz, CDCl$_3$): δ11.78 (d, 1H), 8.93 (d, 1H), 8.86 (d, 1H), 8.32 (d, 1H), 8.01 (d, 1H), 7.70 (t, 1H), 7.53 (dd, 1H), 7.29 (d, 1H), 4.94-4.12 (m, 5H), 3.96-3.48 (m, 2H), 2.48-0.78 (m, 25H); Electrospray mass spec: M+H$^+$ =568.2.

Example 59

Preparation of (R)-2-{[1-(4-((S)-2-[(1-Benzofuran-2-yl-methanoyl)-amino]-4-methyl-pentanoylamino}-3-oxo-azepan-1-yl)-methanoyl]-amino}-4-methyl-pentanoic acid methyl ester

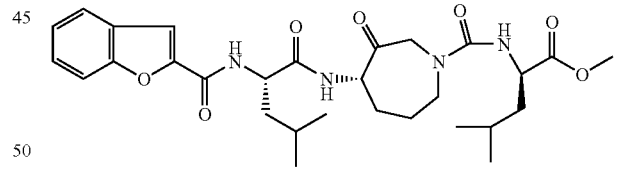

Following the procedure of Example 53 (a-d), except substituting "(3S,4S)-4-Amino-3-hydroxy-azepane-1-carboxylic acid benzyl ester" for "(2R,5S,6S)-5-Amino-6-hydroxy-2-methyl-azepane-1-carboxylic acid benzyl ester" and "(R)-(+)-2-isocyanato-4-methylvaleric acid methyl ester" for "(S)-(−)-2-isocyanato-4-methylvaleric acid methyl ester" the title compound was obtained: 1H NMR of a 1:1 mixture of diastereomers (400 MHz, CDCl$_3$): δ7.69 (d, two 1H), 7.57-7.41 (m, two 3H), 7.37-7.30 (m, two 1H), 7.16-7.08 (m, two 1H), 7.00 and 6.93 (two d, two 1H), 5.11-4.89 (m, two 2H), 4.78-4.49 (m, two 3H), 3.97-3.88 (m, two 1H), 3.81-3.75 (two s, two 3H), 3.62 and 3.60 (two d, two 1H), 2.97-2.85 (m, two 1H), 2.33-2.02 (m, two 2H), 1.88-1.24 (m, two 8H), 1.01 and 0.99 (two d, two 12H); Electrospray mass spec: M+H$^+$=571.4.

Example 60

Preparation of (R)-2-{[1-(4-{(S)-2-[(1-Benzofuran-2-yl-methanoyl)-amino]-4-methyl-pentanoylamino}-3-oxo-azepan-1-yl)-methanoyl]-amino}-4-methyl-pentanoic acid

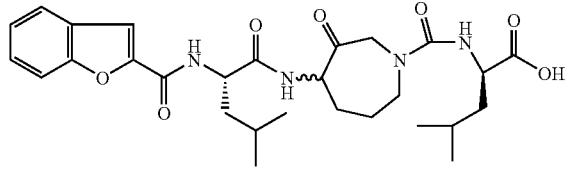

Following the procedure of Example 54 (a), except substituting (R)-2-{[1-(4-{(S)-2-[(1-Benzofuran-2-yl-methanoyl)-amino]-4-methyl-pentanoylamino}-3-oxo-azepan-1-yl)-methanoyl]-amino}-4-methyl-pentanoic acid methyl ester" for (S)-2-{[1-((2R,5S,6S)-5-{(S)-2-[(1-Benzofuran-2-yl-methanoyl)-amino]-4-methyl-pentanoylamino}-6-oxo-2-methyl-azepan-1-yl)-methanoyl]-amino}-4-methyl-pentanoic acid methyl ester" the title compound was obtained: 1H NMR (400 MHz, CDCl$_3$): δ7.68 (d, 1H), 7.56-7.27 (m, 4H), 7.15-7.05 (m, 2H), 5.55 (d, 1H), 5.06 (d, 1H), 4.84 (m, 1H), 4.70 (m, 1H), 4.53 (m, 1H), 3.97 (d, 1H), 3.53 (d, 1H), 2.83 (t, 1H), 2.41-2.26 (m, 1H), 2.22-2.10 (m, 1H), 1.83-1.38 (m, 8H), 1.07-0.82 (m, 12H); Electrospray mass spec: M+H$^+$ =543.4.

Example 61

Preparation of 4,5(R,S)-Benzofuran-2-carboxylic acid {(S)-3-methyl-1-[5-methyl-3-oxo-1-(pyridine-2-sulfonyl)-azepan-4-ylcarbamoyl]-butyl}amide

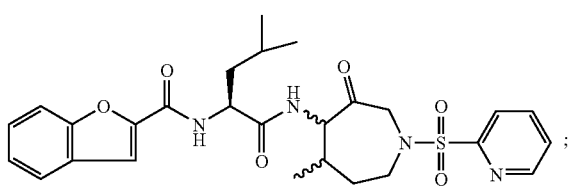

a. 3-Methyl-4-nitro-butyric acid ethyl ester

Ethyl 2-crotonate (10 g, 87 mmol) dissolved in nitromethane (23 mL, 438 mmol) was added 1,1,3,3,-tetramethylguanidine (2 g, 17 mmol). The solution was stirred at RT for 24 h. Ether was added (500 mL) and the organic phase was washed with 1N HCl (100 mL) and dried over sodium sulfate. The solution was filtered, concentrated and product purified on a silica gel column to yield 14 g of the tile compound: $^1$H NMR (400 MHz, CDCl$_3$) δ 4.6 (2H), 4.2 (q, 2H), 2.9 (m, 1H), 2.4 (2H), 1.3 (m, 3H), 1.01(d, 3H). MS (ESI) 174.0 (M+H)$^+$.

b. 3-Methyl-4-nitro-butyaldehyde

To a solution of 3-methyl-4-nitro-butyric acid ethyl ester of Example 61a (1.0 g, 5.71 mmol) in dry toluene at −78° C. was slowly added a cold solution Dibal-H (4 mL, of a 1.5 M solution) so as to maintain the internal temperature below −65° C. The reaction was stirred for an additional 2 h. The reaction was then quenched by slowly adding cold (−78° C.) MeOH. again by keeping the internal temperature below −65° C. The resulting white emulsion was slowly poured into ice-cold 1 N HCl with swirling over 15 minutes and the aqueous mixture was then extracted with EtOAc (3 times). The combined organic layers were washed with brine, dried over sodium sulfate and concentrated to give the crude product which was then purified on a silica gel column to give the pure product as a pale yellow oil. 0.73 g: $^1$H NMR (400 MHz, CDCl$_3$) δ 9.9 (s, 1H), 4.5 (dq, 2H), 2.9 (m, 2H), 2.6 (dq, 1H), 1.1(d, 3H).

c. 2-[Benzyl-(3-methyl-4-nitro-butyl)-amino]-ethanol

To a solution of 3-methyl-4-nitro-butyaldehyde (0.73 g, 5.57 mmol) of Example 61b in methylene chloride (6.0 ml) was added sodium triacetoxyborohydride (1.57 g, 7.4 mmol) and N-Benzyl ethanolamine (0.55 g, 3.67 mmol). The reaction was stirred for 16 h whereupon it was quenched with water, diluted with EtOAc, washed with NaHCO$_3$ and brine. The organic layer was dried over sodium sulfate, concentrated and used directly in the following reaction: $^1$H NMR (400 MHz, CDCl$_3$) δ 7.4 (m, 6H), 4.2 (dq, 2H), 3.6 (m, 4H), 2.3-2.8 (m, 4H), 1.5 (dm, 4H), 1.01(d, 3H). MS (ESI) 265.3 (M+H)$^+$.

d. 3,4,5-(R,S)-1-Benzyl-5-methyl-4-nitro-azepan-3-ol

To a stirring solution of oxalyl chloride (2M in CH$_2$Cl$_2$) (3.38 mL) in methylene chloride at −78 was added DMSO (1.25 mL, 17.6 mmol) slowly. After a 15 min stirring, the alcohol (0.60 g, 2.25 mmol) dissolved in methylene chloride was added slowly. The reaction was continued for a further 1 h at −78. Triethylamine (4.7 mL, 33.8 mmol) was added and the reaction mixture bought to RT, quenched with water and the product extracted into methylene chloride. The organic layer was dried over sodium sulfate, filtered and concentrated. To the crude product in THF was added triethyl amine and the mixture stirred for 16 h to give title compound. The crude product was purified on a silica gel column: $^1$H NMR (400 MHz, CDCl$_3$) δ 7.4 (m, 5H), 4.2 (d, 1H), 3.8 (s, 1H), 1.4-3 (m, 4H), 1.1 (d, 3H), MS (ESI) 265.24 (M+H)$^+$.

e. 3,4,5-(R,S)-4-Amino-1-benzyl-5-methyl-azepan-3-ol

To a 10:1 solution of methanol (56 mL) and 12N HCl (5.60 mL) was slowly added Zn dust (0.43 g, 6.47 mmol). The compound of Example 61d (171 mg, 0.65 mmol) was added and the reaction was heated to reflux for 18 h whereupon it was concentrated in vacuo to remove the methanol. The residue was diluted with ethyl acetate and water and made basic with solid KOH. The mixture was washed with brine, dried over sodium sulfate, filtered and concentrated to give 120 mg of the title compound: MS (ESI) 235.2 (M+H)$^+$.

f. [(S)-1-(1-Benzyl-3-hydroxy-5-methyl-azepan-4-ylcarbamoyl)-3-methyl-butyl]-carbamic acid tert-butyl ester To a solution of the compound from Example 61e (1.12 g, 4.76 mmol) in methylene chloride was added Boc-leucine (1.3 g, 4.76 mmol), EDC (1 g, 4.76 mmol) and HOBt (0.13 g, 0.96 mmol). This mixture was stirred at room temperature for 3 hours whereupon it was diluted with ethyl acetate and washed with an aqueous solution of sodium bicarbonate, the organic layer was dried over sodium sulfate, filtered and concentrated. The crude product was purified on a silica gel column to yield the title compound: $^1$H NMR (400 MHz, CDCl$_3$) δ 8.1 (d, 2H), 7.3 (m, 3H), 1.5 (d, 9H), 1.1 (m, 3H), MS (ESI) 448.4 (M+H)$^+$.

g. [(S)-1-(3-hydroxy-5-methyl-azepan-4-ylcarbamoyl)-3-methyl-butyl]-carbamic acid tert-butyl ester To a solution of the compound of Example 61f in methanol: EtOAc, 1:3 was added 10% Pd/C. This mixture was shaken for 16 h on a Parr Hydrogenation apparatus at 45 psi of hydrogen gas. The reaction mixture was filtered through a pad of celite and concentrated to give the title compound: MS (ESI) 358.4 (M+H)⁺.

h. {(S)-1-[3-Hydroxy-5-methyl-1-(pyridine-2-sulfonyl)-azepan-4-ylcarbamoyl]-3-methyl-butyl}-carbamic acid tert-butyl ester To a solution of Example 61g (6 g, 16.8 mmol) in methylene chloride was added 2-pyridinesulfonyl chloride (3 g, 16.9 mmol) and triethylamine (3 mL, 22.5 mmol). The reaction was allowed to stir at room temperature for 16 h whereupon it was washed with NaHCO₃. The organic layer was dried over sodium sulfate, filtered, concentrated and purified on a silica gel column to yield 5.36 g of the title compound: $^1$H NMR (400 MHz, CDCl₃), δ: 8.7 (d, 1H), 7.9 (m, 2H), 7.4 (m, 1H), 1.7-4.4 (m, 19H), 1.4 (d, 9H), 1.01(d, 6H); MS (ESI) 499.1 (M+H)⁺.

i. (S)-2-Amino-4-methyl-pentanoic acid [3-hydroxy-5-methyl-1-(pyridine-2-sulfonyl)-azepan-4-yl]-amide To a solution of the compound of Example 61 h (5.36 g, 11.57 mmol) in MeOH (2 mL) was added 4M HCl/dioxane (25 mL) and stirred for 2 h. Excess HCl was removed in vacuo and the residue was azeotropically dried with toluene (2×'s) to yield the title compound as the hydrochloride salt 5.37 g: MS (ESI) 399.2 (M+H)⁺.

j. 3,4,5 (R,S)-Benzofuran-2-carboxylic acid {(S)-3-methyl-1-[5-methyl-3-hydroxy-1-(pyridine-2-sulfonyl)-azepan-4-ylcarbamoyl]-butyl}amide To a solution of the compound of Example 61i (0.66 g, 1.26 mmol.) in methylene chlorode was added 2-benzofuran carboxylic acid (0.24 g, 1.51 mmol), EDC (0.29 g, 1.51 mmol), HOBt (0.04 g, 0.29 mmol), Et₃N (1 mL). The reaction was stirred at room temperature for 3 hours whereupon it was washed with an aqueous solution of sodium bicarbonate. The organic layer was dried over sodium sulfate, filtered and concentrated. The crude product was purified on a silica gel column to yield the title compound: $^1$H NMR (400 MHz, CDCl₃), δ: 8.7 (d, 1H), 7.1-7.9 (m, 8H), 1.74.4 (m, 11H), 0.9-1.5 (m, 13H). MS (ESI) 565.08 (M+Na)⁺.

k. 4,5 (R,S) Benzofuran-2-carboxylic acid {(S)-3-methyl-1-[5-methyl-3-oxo-1-(pyridine-2-sulfonyl)-azepan-4-ylcarbamoyl]-butyl}amide To a solution of the compound of Example 61j (0.15 g, 0.27 mmol) in methylene chloride was added Dess-Martin reagent (0.17 g, 0.41 mmol). The reaction was stirred at room temperature for 1 hour, diluted with methylene chloride then washed with sodium thiosulfate, sodium bicarbonate and brine. The organic layer was washed dried over sodium sulfate, filtered, concentrated and purified on a silica gel column to provide (0.1 g) of the title compound as a mixture of four diastereomers: $^1$H NMR (400 MHz, CDCl₃), δ: 8.7 (d, 1H), 7.1-7.9 (m, 8H), 1.74.4 (m, 10H), 0.9-1.5 (m, 13H). MS (ESI) 540.08 (M+H).

This mixture was separated by HPLC to provide the 4 individual diastereomers as white powders.

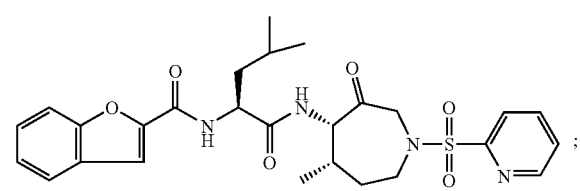

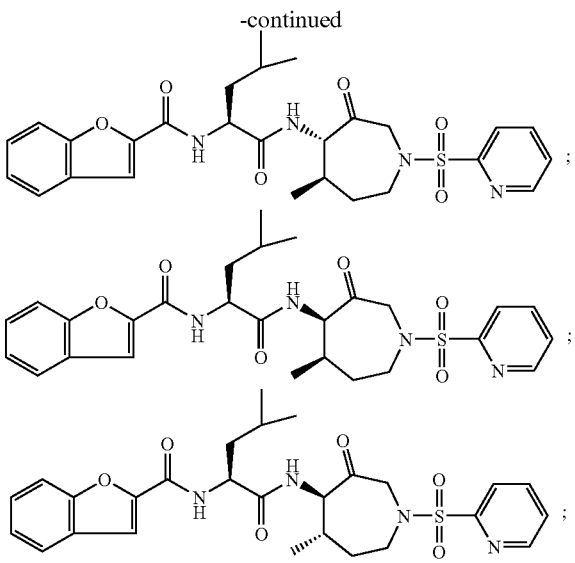

Example 62

Preparation of (R)-2-Biphenyl-3-yl-4-methyl-pentanoic acid [(4S,7R)-7-methyl-3-oxo-1-(pyridine-2-sulfonyl)-azepan-4-yl]-amide

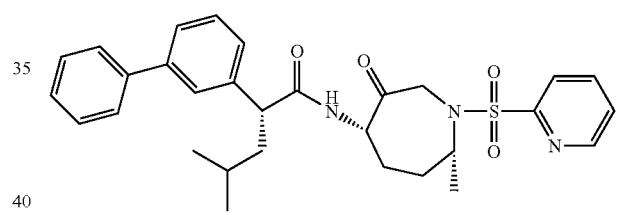

a. (2R,5R,6R)-5-Azido-6-hydroxy-2-methyl-azepane-1-carboxylic acid benzyl ester

Sodium azide (1.8 g, 27.7 mmol) was added to a (1R,4R,7S)-4-Methyl-8-oxa-3-aza-bicyclo[5.1.0]octane-3-carboxylic acid benzyl ester (2.4 g, 9.2 mmol, Example 1e) and ammonium chloride (1.48 g, 27.7 mmol) in MeOH (16 ml) and H₂O (1.6 ml), then was refluxed overnight. The reaction mixture was concentrated in vacuo by rotary evaporation, then was diluted with water (5 ml) and extracted with EtOAc (10 ml). The organic layer was then extracted with water, brine, dried with MgSO₄, filtered, concentrated in vacuo by rotary evaporation, and chromatographed (silica gel, 25% EtOAc/hexanes) to yield the title compound (1.76 g, 63%); Liquid chromatgraphy/Electrospray mass spec: M+H⁺=305.2.

b. (2R,5R,6R)-5-Amino-6-hydroxy-2-methyl-azepane-1-carboxylic acid benzyl ester

Triphenylphosphine (2.13 g, 8.14 mmol) was added to a solution (2R,5R,6R)-5-Azido-6-hydroxy-2-methyl-azepane-1-carboxylic acid benzyl ester (1.65 g, 5.43 mmol) in THF (200 ml) and H₂O (0.8 ml), then was heated to 45 degrees C. overnight. The reaction mixture was then diluted with toluene (100 ml×2) and was azeotroped in vacuo by rotary evaporation twice. The resulting oil was dissolved in MeOH and HCl in Et$_2$O and the resulting salt was collected following filtration and was used in the next reaction without further purification (1.7 g, quantitative).

c. (2R,5R,6R)-5-tert-Butoxycarbonylamino-6-hydroxy-2-methyl-azepane-1-carboxylic acid benzyl ester Boc anhydride (0.9 g, 4.13 mmol) was added to a solution of (2R,5R,6R)-5-Amino-6-hydroxy-2-methyl-azepane-1-carboxylic acid benzyl ester (1.0 g, 3.18 mmol), triethylamine (0.38 g, 0.53 ml, 3.82 mmol) in THF (5 ml) and H$_2$O (5 ml) and was stirred at RT for 1H. The THF and excess triethylamine were removed in vacuo, then the reaction mixture was diluted with H$_2$O (10 ml), extracted with EtOAc (3×20 ml), then the combined organics were extracted with H$_2$O (30 ml), brine (30 ml), dried with MgSO4, filtered through silica gel, concentrated, then used in the next reaction without further purification (1.0 g, 83%): Electrospray mass spec: M+H$^+$=379.2.

d. ((3R,4R,7R)-3-Hydroxy-7-methyl-azepan-4-yl)-carbamic acid tert-butyl ester (2R,5R,6R)-5-tert-Butoxycarbonylamino-6-hydroxy-2-methyl-azepane-1-carboxylic acid benzyl ester (0.9 g, 2.4 mmol) was dissolved in EtOAc (40 ml), then 10% Pd/C (0.45 g) was added and the reaction mixture was degasses by bubbling argon for 5 minutes. Then, the reaction was stirred overnight under a balloon filled with hydrogen gas. The reaction mixture was filtered through Celite, concentrated in vacuo by rotary evaporation and was azeotroped with toluene (20 ml), then was used in the next reaction without further purification (0.58 g, quantitative): Electrospray mass spec: M+H$^+$=245.2.

e. [(3R,4R,7R)-3-Hydroxy-7-methyl-1-(pyridine-2-sulfonyl)-azepan-4-yl]-carbamic acid tert-butyl ester Pyridine-2-sulfonyl chloride (0.55 g, 3.1 mmol) was added to a solution ((3R,4R,7R)-3-Hydroxy-7-methyl-azepan-4-yl)-carbamic acid tert-butyl ester (0.58 g, 0.2.4 mmol), sodium bicarbonate (0.84 g, 10 mmol) in CH$_2$Cl$_2$ (10 ml) and H$_2$O (3 ml) and was stirred at RT for 30 minutes. The reaction mixture was diluted with EtOAc (100 ml), washed with H$_2$O, brine, dried with magnesium sulfate, filtered, concentrated in vacuo by rotary evaporation, and chromatographed (silica gel, 45:55 EtOAC/hexanes) to yield the title compound (0.6 g, 65%): Electrospray mass spec: M+H$^+$=386.27.

f. (3R,4R,7R)-4-Amino-7-methyl-1-(pyridine-2-sulfonyl)-azepan-3-ol

HCl in dioxane (4.0 M, 10 ml) was added to a stirred solution. [(3R,4R,7R)-3-Hydroxy-7-methyl-1-(pyridine-2-sulfonyl)-azepan-4-yl]-carbamic acid tert-butyl ester (0.6 g, 1.55 mmol) in MeOH (10 ml). The reaction mixture was stirred for 1 h at RT, then was diluted with toluene (20 ml), concentrated in vacuo by rotary evaporation and was used in the next reaction without further purification (0.5 g, quantitative): Electrospray mass spec: M+H$^+$=286.2.

g. 2-Biphenyl-3-yl-4-methyl-pentanoic acid [(3R,4R,7R)-7-methyl-3-hydroxy-1-(pyridine-2-sulfonyl)-azepan-4-yl]-amide 2-Biphenyl-3-yl-4-methyl-pentanoic acid (270 mg, 1.0 mmol, preparation described in *J. Am. Chem. Soc.* 1997, 120, 9114), and (3R,4R,7R)-4-Amino-7-methyl-1-(pyridine-2-sulfonyl)-azepan-3-ol (320 mg, 1.0 mmol, Example 1k), EDCI (190 mg, 1.0 mmol), HOBT (135 mg, 1.0 mmol) and diisopropylethylamine (1.7 g, 0.23 ml, 1.3 mmol) in DMF (5 ml) were stirred at RT for 4 h. The reaction mixture was diluted with EtOAc (20 ml), washed with H$_2$O, brine, dried with magnesium sulfate, filtered, concentrated in vacuo by rotary evaporation, and chromatographed (silica gel, 40% EtOAc/hexanes) to yield the title compound (330 mg, 62%): $^1$H NMR (400 MHz, CDCl$_3$): δ 8.55-8.60 (m, 1H), 8.00 (t, 1H), 7.80-7.90 (m, 1H), 7.65 (d, 2H), 7.25-7.55 (m, 8H), 5.50-5.60 (m, 1H), 4.00-4.10 (m, 1H), 3.70-3.85 (m, 1H), 3.50-3.70 (m, 2H), 2.90-3.05 (m, 1H), 2.00-2.10 (m, 2H), 1.30-1.85 (m, 5H), 0.90-0.95 (d, 9H); ESMS: 536.4 (M+H$^+$)

h. (R)-2-Biphenyl-3-yl-4-methyl-pentanoic acid [(4S,7R)-7-methyl-3-oxo-1-(pyridine-2-sulfonyl)-azepan-4-yl]-amide Dess-Martin periodinane (400 mg, 0.93 mmol) was added to a solution 2-Biphenyl-3-yl-4-methyl-pentanoic acid [(3R,4R,7R)-7-methyl-3-hydroxy-1-(pyridine-2-sulfonyl)-azepan-4-yl]-amide (330 mg, 0.62 mmol) in CH$_2$Cl$_2$ (15 ml) and was stirred at RT for 4 h. The solution was washed with 10% aq. Na$_2$S$_2$O$_3$, aq. sat. NaHCO$_3$, and brine, then concentrated in vacuo, then chromatographed (silica gel, 50% EtOAc/hexanes) to provide a mixture of diasteromers (260 mg, 60%), which was then dissolved in MeOH (12 ml) and triethylamine (0.44 g, 0.6 ml, 4.4 mmol), and was stirred at RT for 3 days. The reaction mixture was concentrated in vacuo, then chromatographed to yield a mixture of primarily (R)- and (S)-2-Biphenyl-3-yl-4-methyl-pentanoic acid [(4S,7R)-7-methyl-3-oxo-1-(pyridine-2-sulfonyl)-azepan-4-yl]-amides (200 mg, 77%). The diastereomers were separated using HPLC (R,R-Whelk-O preparative column, 40% EtOH/hexanes): Diastereomer 1 (retention time 13 min): $^1$H NMR (400 MHz, CDCl$_3$): δ 8.70 (d, 1H), 8.00 (d, 1H), 7.90 (t, 1H), 7.60 (d, 2H), 7.25-7.55 (m, 8H), 6.52 (d, 1H), 5.05-5.15 (m, 1H), 4.75 (d, 1H), 4.35-4.45 (m, 1H), 3.82 (d, 1H), 3.50 (t, 1H), 2.00-2.20 (m, 3H), 1.70-1.80 (m, 1H), 1.40-1.65 (m, 2H), 1.25-1.40 (m, 1H), 0.9-1.0 (m, 9H); ESMS: 534.2 (M+H$^+$);

Diastereomer 2 (retention time 21 min): $^1$H NMR (400 MHz, CDCl$_3$): δ 8.65 (d, 1H), 8.00 (d, 1H), 7.90 (t, 1H), 7.60 (d, 2H), 7.25-7.60 (m, 8H), 6.60 (d, 1H), 4.95-5.02 (m, 1H), 4.70 (d, 1H), 4.40-4.50 (m, 1H), 3.85 (d, 1H), 3.50 (t, 1H), 2.12-2.30 (m, 2H), 2.00-2.10 (m, 1H), 1.70-1.80 (m, 1H), 1.60-1.70 (m, 1H), 1.40-1.60 (m, 2H), 1.00 (d, 3H), 0.95 (d, 6H); ESMS: 534.2 (M+H$^+$)

Example 63

Preparation of 3-Methyl-furo[3,2-b]-pyridine-2-carboxylic acid {1-[(4S,7R)-7-methyl-3-oxo-1-(pyridine-2-sulfonyl)-azepan-4-ylcarbamoyl]-cyclohexyl}-amide

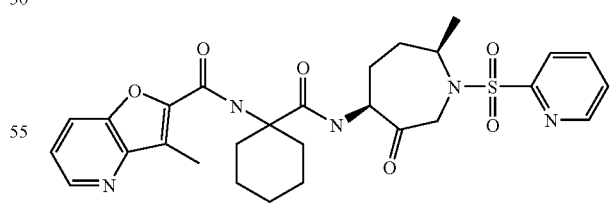

Following the procedure of Example 12 (a-m), except substituting "N-Boc-amino-cyclohexane carboxylic acid" for "Boc-L-leucine" and "3-Methyl-furo[3,2-b]-pyridine-2-carboxylic acid" for "quinoline-6-carboxylic acid" gave the title compound: 1H NMR: 8.72(d, 1H), 8.65(d, 1H), 7.98(m, 1H), 7.90(m, 1H), 7.80(d, 1H), 5.11(m, 1H), 4.76(d, 1H), 4.43(m, 1H), 3.81(d, 1H), 2.82(s, 3H), 2.32-1.35(m, 14H), 0.95(d, 3H);

Electrospray mass spec: M+H$^+$=568.2.

Example 64

Preparation of 1-(3-Cyclohexyl-propanoylamino)-cyclohexanecarboxylic acid [(4S,7R)-7-methyl-3-oxo-1-(pyridine-2-sulfonyl)-azepan-4-yl]-amide

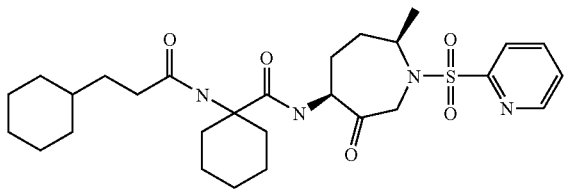

Following the procedure of Example 12 (a-m), except substituting "N-Boc-amino-cyclohexane carboxylic acid" for "Boc-L-leucine" and "3-Cyclohexyl-propananoic acid" for "quinoline-6-carboxylic acid" gave the title compound: 1H NMR: 8.71(d, 1H), 7.97(m, 2H), 7.72(m, 3H), 6.60(s, 1H), 5.04(m, 1H), 4.71(d, 1H), 4.42(m, 1H), 3.81(d, 1H), 2.27-0.73(m, 31H); Electrospray mass spec: M+specification and Examples fully disclose how to make and use the compounds of the present invention H$^+$=544.4.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound which is 3-methyl-furo[3,2-b]pyridine-2-carboxylic acid {(S)-3-methyl-1-[(4S,7R)-7-methyl-3-oxo-1-(pyridine-2-sulfonyl)-azepan-4-ylcarbamoyl]-butyl}-amide; or a pharmaceutically acceptable salt thereof.

2. A pharmaceutical composition comprising a compound according to claim 1 and a pharmaceutically acceptable carrier, diluent or excipient.

3. A method of treating osteoporosis by administering to a patient in need thereof an effective amount of a compound according to claim 1.

4. A method of treating periodontitis by administering to a patient in need thereof an effective amount of a compound according to claim 1.

5. A method of treating gingivitis by administering to a patient in need thereof an effective amount of a compound according to claim 1.

6. A method of treating osteoarthritis by administering to a patient in need thereof an effective amount of a compound according to claim 1.

7. A method of treating rheumatoid arthritis by administering to a patient in need thereof an effective amount of a compound according to claim 1.

* * * * *